(12) United States Patent
Tada et al.

(10) Patent No.: US 7,767,739 B2
(45) Date of Patent: Aug. 3, 2010

(54) CYANATO GROUP-CONTAINING CYCLIC PHOSPHAZENE COMPOUND AND METHOD FOR PRODUCING THE SAME

(75) Inventors: Yuji Tada, Marugame (JP); Takashi Inoue, Marugame (JP)

(73) Assignee: Fushimi Pharmaceutical Co., Ltd., Kagawa (JP)

( * ) Notice: Subject to any disclaimer, the term of this patent is extended or adjusted under 35 U.S.C. 154(b) by 91 days.

(21) Appl. No.: 12/087,585

(22) PCT Filed: Jan. 9, 2007

(86) PCT No.: PCT/JP2007/050378

§ 371 (c)(1),
(2), (4) Date: Nov. 7, 2008

(87) PCT Pub. No.: WO2007/080998

PCT Pub. Date: Jul. 19, 2007

(65) Prior Publication Data

US 2009/0170983 A1    Jul. 2, 2009

(30) Foreign Application Priority Data

Jan. 13, 2006    (JP) .............................. 2006-005657

(51) Int. Cl.
*C08K 5/5399* (2006.01)
*C07F 9/547* (2006.01)

(52) U.S. Cl. .................... 524/95; 524/116; 558/157; 564/13

(58) Field of Classification Search ................ 524/95, 524/116; 564/13; 558/157
See application file for complete search history.

(56) References Cited

U.S. PATENT DOCUMENTS

| 5,840,471 | A | * | 11/1998 | Fukuwatari et al. | ......... | 430/399 |
| 5,994,497 | A | | 11/1999 | Raith et al. | | |
| 6,518,336 | B1 | * | 2/2003 | Yabuhara et al. | ............ | 524/116 |
| 2003/0220515 | A1 | * | 11/2003 | Yoshifumi et al. | .......... | 558/157 |

FOREIGN PATENT DOCUMENTS

| EP | 0921432 | * | 6/1999 |
| JP | 6-247989 | A | 9/1994 |
| JP | 10-168428 | A | 6/1998 |
| JP | 10-259292 | A | 9/1998 |
| JP | 2000-103939 | A | 4/2000 |
| JP | 2002-62614 | A | 2/2002 |
| JP | 2003-302751 | A | 10/2003 |
| JP | 2003-342339 | A | 12/2003 |
| JP | 2004-83671 | A | 3/2004 |
| JP | 2004-143465 | A | 5/2004 |
| JP | 2004-210849 | A | 7/2004 |
| JP | 2005-248134 | A | 9/2005 |
| JP | 2005-8835 | A | 1/2008 |
| WO | PCT/JP2007/050378 | | 7/2008 |

OTHER PUBLICATIONS

Allcock, H.R. et al. "Phosphorus Nitrogen Compounds", Academic Press, 1972. p. 5-7, 151.
Gleria, Mario et al. "Phosphazenes A Worldwide Insight", Nova Science Publishers, Inc, 2004. p. 35-37.
Greene, Theodora W., et al. "Protective Groups in Organic Synthesis, Protection For Phenols and Catechols" John Wiley and Sons Inc. 1999. pp. 246-287, 749-779.
Robertson, Jeremy et al. "Protecting Group Chemistry" Oxford University Press Inc.., New York. pp. 16-17, Circa 2000.
Hamerton, I. "Chemistry and Technology of Cyanateester Resins", Blackie Academic & Professional, 1994. pp. 9-18.
Jensen, K.A. et al. "The Cehmistry of cyanates and their thio derivatives, Synthesis and preparative applications of cyanates (esters of cyanic acid)" The Hebrew University, Jerusalem, 1977.pp. 569-576.
Medici, Alessandro et al. "Macromolecules" vol. 25, No. 10, May 11, 1992. pp. 2570-2574.

* cited by examiner

*Primary Examiner*—Milton I Cano
*Assistant Examiner*—John Uselding
(74) *Attorney, Agent, or Firm*—Birch, Stewart, Kolasch & Birch, LLP

(57) ABSTRACT

A phosphazene compound, which can effectively enhance flame retardancy without deteriorating mechanical properties of a resin molded product, and is also less likely to deteriorate thermal reliability and dielectric properties, is represented by the formula (1) shown below. n represents an integer of 3 to 15.

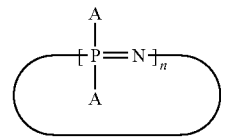

(1)

wherein A represents a group selected from the group consisting of an alkoxy group, an aryloxy group and a group having a cyanato group, and at least one is a group having a cyanato group, and an example of A is a cyanatophenyl-substituted phenyloxy group represented by the formula (4) shown below, and Y in the formula (4) represents O, S, $SO_2$, $CH_2$, $CHCH_3$, $C(CH_3)_2$, $C(CF_3)_2$, $C(CH_3)CH_2CH_3$ or CO.

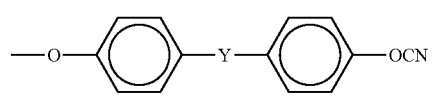

(4)

14 Claims, No Drawings

CYANATO GROUP-CONTAINING CYCLIC PHOSPHAZENE COMPOUND AND METHOD FOR PRODUCING THE SAME

This is a national phase application of International Application PCT/JP2007/050378 filed Jan. 9, 2007, which claims the benefit of Japan 2006-005657 filed Jan. 1, 2006.

TECHNICAL FIELD

The present invention relates to a cyclic phosphazene compound and a method for producing the same, and particularly to a cyanato group-containing cyclic phosphazene compound and a method for producing the same.

BACKGROUND ART

In the fields of industrial/consumer equipments and electric appliances, synthetic resins are widely used as they are excellent in processability, chemical resistance, weatherability, electrical properties and mechanical strength as compared with other materials, and also the amount of synthetic resins used has been increasing. However, since synthetic resins have flammability, it is required to impart flame retardancy and the required performances have gradually enhanced recently. Therefore, a halogen-containing compound or a mixture of a halogen-containing compound and an antimony compound such as antimony oxide, as a conventional flame retardant, is added to a resin composition, for example, an epoxy resin composition used in an encapsulant and a substrate of electronic components such as LSI (Large Scale Integration) so as to impart flame retardancy. However, the resin composition containing such a flame retardant may generate a halogen-based gas which may cause environmental pollution upon combustion or molding. Also, the halogen-based gas may inhibit electrical properties and mechanical properties of electronic components. Thus, as a flame retardant for synthetic resin, non-halogen-based flame retardants which are less likely to generate a halogen-based gas upon combustion or molding, for example, metal hydrate-type flame retardants such as aluminum hydroxide and magnesium hydroxide, and phosphorous-type flame retardants such as phosphate-type flame retardants, condensed phosphate-type flame retardants, phosphoric amide-type flame retardants, ammonium polyphosphate-type flame retardants and phosphazene-type flame retardants, are widely used.

Among these flame retardants, metal hydrate-type flame retardants must be used in a large amount to a resin composition so as to enhance the flame-retardancy, although they exert the flame-retardant effect by that an endothermic reaction of dehydration thermolysis and release of water thereby occur in the same temperature range as that of thermolysis or combustion initiation of the synthetic resin. Therefore, a molded article of a resin composition containing this kind of a flame retardant has a drawback that a mechanical strength decreases. Meanwhile, among phosphorous-type flame retardants, phosphate-type flame retardants and condensed phosphate-type flame retardants have drawbacks that the mechanical strength of the resin molded article decreases when a large amount of flame retardants are added to the resin composition so as to enhance flame retardancy because they have a plasticizing effect. As for phosphate-type flame retardants, phosphoric amide-type flame retardants and ammonium polyphosphate-type flame retardants, it is substantially difficult to use them in materials for production of resin molded articles to which long-term mechanical and electrical reliability is required as they are likely to be hydrolyzed. In contrast, phosphazene-type flame retardants have widely been used as an effective flame retardant for the synthetic resin, as described in the documents 1 to 5 below, since they exert less plasticizing effect and has less hydrolyzability as compared with other phosphorous-type flame retardants, and thus the amount of them to be added to the resin composition can increase. However, when the amount of the phosphazene-type flame retardants to be added to the resin composition is increased, reliability of the resin molded article at high temperature may deteriorate. Specifically, in the case of a thermoplastic resin-type resin composition, phosphazene-type flame retardants are likely to bleed out (leak out) from the resin molded article at high temperature. In the case of a thermosetting resin-type resin composition, deformation such as blister of the resin molded article may occur at high temperature and a short-circuit may be caused thereby when the resin molded article is used as a laminated substrate or the like in electronic and electric fields.

Document 1
  Japanese Unexamined Patent Publication (Kokai) No. 2000-103939

Document 2
  Japanese Unexamined Patent Publication (Kokai) No. 2004-83671

Document 3
  Japanese-Unexamined Patent Publication (Kokai) No. 2004-210849

Document 4
  Japanese Unexamined Patent Publication (Kokai) No. 2005-8835

Document 5
  Japanese Unexamined Patent Publication (Kokai) No. 2005-248134

Thus, an improvement of the phosphazene-type flame retardants is studied so as to enhance reliability of the resin molded article at high temperature (thermal reliability). For example, documents 6 to 10 below disclose phosphazene-type flame retardants having a reactive group such as a hydroxyl group, and epoxy resin and polyimide resin compositions using them. Even if a large amount of these phosphazene-type flame retardants are added to the resin composition, thermal reliability of the resin molded article is less likely to deteriorate. However, phosphazene-type flame retardants are insufficient in a required essential result of effectively enhancing flame retardancy of the resin molded article even if the amount is increased, and also deteriorate mechanical properties (particularly, high glass transition temperature) of the resin molded article.

Document 6
  Japanese Unexamined Patent Publication (Kokai) No. 6-247989

Document 7
  Japanese Unexamined Patent Publication (Kokai) No. 10-259292

Document 8
  Japanese Unexamined Patent Publication (Kokai) No. 2003-302751

Document 9
  Japanese Unexamined Patent Publication (Kokai) No. 2003-342339

Document 10

Japanese Unexamined Patent Publication (Kokai) No. 2004-143465

With recent size reduction and achievement of higher function of electronic equipments, substrate materials, which are thin and lightweight and also capable of achieving higher density wiring, are required for printed circuit boards. As a printed circuit boards, build-up laminated type of small size with an IVH (Interstitial Via Hole) structure, in which only required layers are connected by way of non-through holes, have rapidly been developed. As for an insulating layer of a printed circuit board of the build-up laminated type, a heat-resistant resin having high glass transition temperature (Tg) is required to be used instead of a base material such as a glass fabric.

In computers and information equipment terminals, an increase in frequency of signal is promoted so as to process much data at higher speed. However, there is a problem that transmission loss of electrical signal increases as the frequency increases, and it is strongly required to develop printed circuit boards suitable for higher frequency signal. Dielectric loss determined by dielectric properties of an insulating layer (dielectric) in the vicinity of a wiring exerts a large influence on transmission loss in a high frequency circuit, and it becomes necessary to achieve low dielectric constant and low dissipation factor (tan δ) of a substrate for a printed circuit board (particularly insulating resin). For example, in equipments relating to a mobile communication, a substrate having low dissipation factor is strongly required so as to decrease transmission loss in a quasi-microwave band (1 to 3 GHz) with the increase of frequency of signal.

Furthermore, in electronic information equipments such as computers, a high-speed microprocessor having operating frequency of more than 1 GHz is mounted and there arise a problem such as delay of high-speed pulse signal in a printed circuit board. Since delay time of signal increases in proportion to square root of a relative dielectric constant ∈r of an insulator in the vicinity of a wiring in a printed circuit board, a substrate for a circuit board having low dielectric constant is required in high-speed computers.

Therefore, it is necessary for phosphazene-type flame retardants to scarcely cause deterioration of dielectric properties of the resin molded article, that is, to achieve low dielectric constant and low dissipation factor of the resin molded article.

Thus, an object of the present invention is to realize a phosphazene compound which can effectively enhance flame retardancy without deteriorating mechanical properties of a resin molded article, and is also less likely to deteriorate thermal reliability and dielectric properties of the resin molded article.

DISCLOSURE OF THE INVENTION

The present inventors have intensively studied so as to achieve the above object and found that a molded product made of a resin composition containing a novel phosphazene compound having a cyanato group exhibits excellent mechanical properties and flame retardancy, and also has high reliability at high temperature and is excellent in dielectric properties.

The phosphazene compound of the present invention is a cyanato group-containing cyclic phosphazene compound represented by the following formula (1):

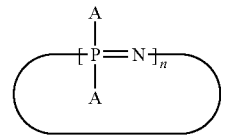

(1)

in the formula (1), n represents an integer of 3 to 15, A represents a group selected from the group consisting of an A1 group, an A2 group and an A3 group shown below and at least one group is an A3 group:

A1 group: an alkoxy group having 1 to 8 carbon atoms which may be substituted with at least one group selected from an alkyl group having 1 to 6 carbon atoms, an alkenyl group and an aryl group;

A2 group: an aryloxy group having 6 to 20 carbon atoms which may be substituted with at least one group selected from an alkyl group having 1 to 6 carbon atoms, an alkenyl group and an aryl group; and A3 group: a group selected from the group consisting of a cyanatophenyloxy group represented by the formula (2) shown below, a cyanatophenyl-substituted phenyloxy group represented by the formula (3) shown below, a cyanatophenyl-substituted phenyloxy group represented by the formula (4) shown below, a cyanatophenyl-substituted indanoxy group represented by the formula (5) shown below and a cyanatoindane-substituted phenyloxy group represented by the formula (6) shown below:

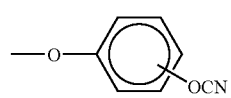

(2)

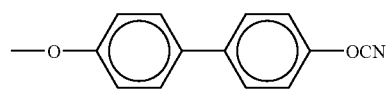

(3)

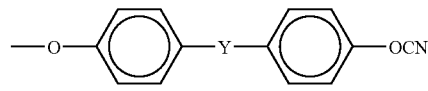

(4)

in the formula (4), Y represents O, S, SO$_2$, CH$_2$, CHCH$_3$, C(CH$_3$)$_2$, C(CF$_3$)$_2$, C(CH$_3$)CH$_2$CH$_3$ or CO,

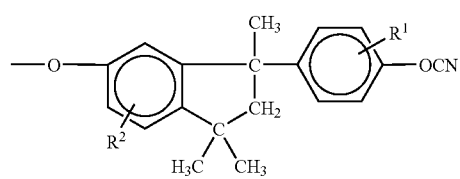

(5)

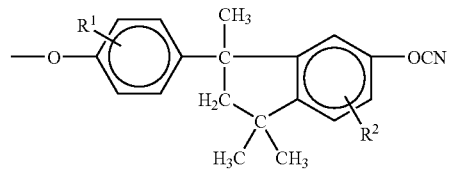

(6)

in the formulas (5) and (6), $R^1$ and $R^2$ represent a hydrogen atom, an alkyl group having 1 to 4 carbon atoms, a cycloalkyl group or a phenyl group.

In the cyanato group-containing cyclic phosphazene compound, for example, n in the formula (1) is 3 or 4. In the cyanato group-containing cyclic phosphazene compound, for example, 2 to (2n−2) A groups of 2n A groups are A3 groups or all 2n A groups are A3 groups in the formula (1). Furthermore, the cyanato group-containing cyclic phosphazene compound includes two or more kinds of cyanato group-containing cyclic phosphazene compounds in which n in the formula (1) is different.

The cyanato group-containing cyclic phosphazene compound of the present invention has a specific structure described above and thus flame retardancy can be effectively enhanced without deteriorating mechanical properties of a resin molded product, and also thermal reliability and dielectric properties of a resin molded product are less likely to deteriorate.

The method for producing a cyanato group-containing cyclic phosphazene compound of the present invention includes the following steps A, B and C:

[Step A]

a step of substituting all halogen atoms of a cyclic phosphonitrile dihalide represented by the formula (7) shown below with a group selected from the group consisting of an E1 group, an E2 group and an E3 group shown below so as to substitute at least one of the halogen atoms with the E3 group shown below to produce a cyclic phosphonitrile-substituted compound;

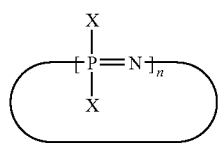
(7)

in the formula (7), n represents an integer of 3 to 15 and X represents a halogen atom, E1 group: an alkoxy group having 1 to 8 carbon atoms which may be substituted with at least one group selected from an alkyl group having 1 to 6 carbon atoms, an alkenyl group and an aryl group;

E2 group: an aryloxy group having 6 to 20 carbon atoms which may be substituted with at least one group selected from an alkyl group having 1 to 6 carbon atoms, an alkenyl group and an aryl group; and E3 group: a group selected from the group consisting of a substituted phenyloxy group represented by the formula (8) shown below, a substituted phenyloxy group represented by the formula (9) shown below, a substituted phenyloxy group represented by the formula (10) shown below, a substituted indanoxy group represent by the formula (11) shown below and a substituted phenyloxy group represent by the formula (12) shown below:

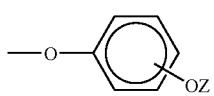
(8)

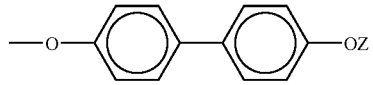
(9)

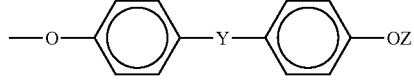
(10)

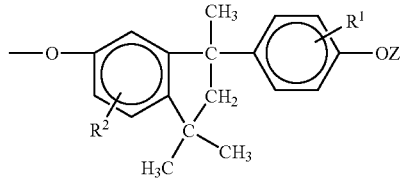
(11)

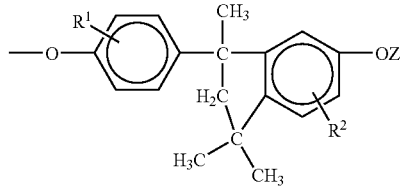
(12)

wherein Z in the formulas (8), (9), (10), (11) and (12) represents a protecting group capable of forming an OH group when eliminated, Z is selected from the group consisting of a methyl group, a methoxyethyl group, a tert-butyl group, an allyl group and a benzyl group, Y in the formula (10) represents O, S, $SO_2$, $CH_2$, $CHCH_3$, $C(CH_3)_2$, $C(CF_3)_2$, $C(CH_3)CH_2CH_3$ or CO, and $R^1$ and $R^2$ in the formulas (11) and (12) represent a hydrogen atom, an alkyl group having 1 to 4 carbon atoms, a cycloalkyl group or a phenyl group;

[Step B]

a step of eliminating the protecting group (Z) from the E3 group of the cyclic phosphonitrile-substituted compound obtained in step A to produce a cyclic phosphonitrile-substituted compound having a hydroxyl group; and

[Step C]

a step of reacting the cyclic phosphonitrile-substituted compound having a hydroxyl group obtained in step B with a cyanogen halide.

Since this method includes the above steps A, B and C, a cyanato group-containing cyclic phosphazene compound having the above specific structure of the present invention can be produced.

The resin composition of the present invention includes a resin component and a cyanato group-containing cyclic phosphazene compound of the present invention. For example, the resin component is selected from the group consisting of a cyanate ester resin, an epoxy resin, a polyimide resin, a bismaleimide resin, a bismaleimide-cyanate ester resin and a modified polyphenylene ether resin.

In one embodiment of the resin composition of the present invention, the resin component is an epoxy resin and the resin composition further contains a curing agent.

Since the resin composition contains the cyanato group-containing cyclic phosphazene compound of the present invention as a flame retardant, it is possible to obtain a resin molded product which exhibits practical mechanical properties and flame retardancy, and also has high thermal reliability and is excellent in dielectric properties.

The polymerizable composition of the present invention contains a cyanato group-containing cyclic phosphazene compound of the present invention. The polymerizable composition further contains, for example, a curing agent.

Since the polymerizable composition contains the cyanato group-containing cyclic phosphazene compound of the present invention, it is possible to obtain a resin molded product which exhibits practical mechanical properties and flame retardancy by the polymerization, and also has high thermal reliability and is excellent in dielectric properties.

The resin molded product of the present invention is made of a resin composition of the present invention, or of the polymer of a polymerizable composition of the present invention, and therefore exhibits practical mechanical properties and flame retardancy, and also has high thermal reliability and is excellent in dielectric properties.

Other objects and results of the present invention will be described in the following detailed description.

BEST MODE FOR CARRYING OUT THE INVENTION

Cyanato Group-Containing Cyclic Phosphazene Compound

The cyanato group-containing cyclic phosphazene compound of the present invention is represented by the following formula (1):

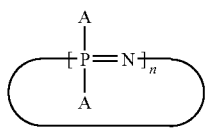

(1)

in the formula (1), n represents an integer of 3 to 15, preferably an integer of 3 to 8, and particularly preferably 3 or 4. That is, a cyanato group-containing cyclotriphosphazene in which n is 3 (trimer) and a cyanato group-containing cyclotetraphosphazene in which n is 4 (tetramer) are particularly preferred as the cyanato group-containing cyclic phosphazene compound. The cyanato group-containing cyclic phosphazene compound of the present invention may be a mixture of two or more kinds of compounds each having different n.

In the formula (1), A represents a group selected from the group consisting of an A1 group, an A2 group and an A3 group shown below, provided that at least one of A groups is an A3 group.

[A1 Group]

An alkoxy group having 1 to 8 carbon atoms, which may be substituted with at least one group selected from the group consisting of an alkyl group having 1 to 6 carbon atoms, an alkenyl group and an aryl group.

Examples of the alkoxy group include a methoxy group, an ethoxy group, a n-propoxy group, an isopropoxy group, a n-butoxy group, a sec-butoxy group, a tert-butoxy group, a n-pentyloxy group, a n-hexyloxy group, a n-heptyloxy group, a n-octyloxy group, an ethenyloxy group, a 1-propenyloxy group, a 2-propenyloxy group, an isopropenyloxy group, a 3-butenyloxy group, a 2-methyl-2-propenyloxy group, a 4-pentenyloxy group, a 2-hexenyloxy group, a 1-propyl-2-butenyloxy group, a 5-octenyloxy group, a benzyloxy group and a 2-phenylethoxy group. Among these groups, a methoxy group, an ethoxy group, a n-propoxy group, a 2-propenyloxy group and a benzyloxy group are preferred, and an ethoxy group and a n-propoxy group are particularly preferred.

[A2 Group]

An aryloxy group having 6 to 20 carbon atoms, which may be substituted with at least one group selected from the group consisting of an alkyl group having 1 to 6 carbon atoms, an alkenyl group and an aryl group.

Examples of the aryloxy group include a phenoxy group, a methylphenoxy group, a dimethylphenoxy group, an ethylphenoxy group, an ethylmethylphenoxy group, a diethylphenoxy group, a n-propylphenoxy group, an isopropylphenoxy group, an isopropylmethylphenoxy group, an isopropylethylphenoxy group, a diisopropylphenoxy group, a n-butylphenoxy group, a sec-butylphenoxy group, a tert-butylphenoxy group, a n-pentylphenoxy group, a n-hexylphenoxy group, an ethenylphenoxy group, a 1-propenylphenoxy group, a 2-propenylphenoxy group, an isopropenylphenoxy group, a 1-butenylphenoxy group, a sec-butenylphenoxy group, a 1-pentenylphenoxy group, a 1-hexenylphenoxy group, a phenylphenoxy group, a naphthyloxy group, an anthryloxy group and a phenanthryloxy group. Among these groups, a phenoxy group, a methylphenoxy group, a dimethylphenoxy group, a diethylphenoxy group, a 2-propenylphenoxy group, a phenylphenoxy group and a naphthyloxy group are preferred, and a phenoxy group, a methylphenoxy group, a dimethylphenoxy group and a naphthyloxy group are particularly preferred.

[A3 Group]

A group selected from the group consisting of a cyanatophenyloxy group represented by the formula (2) shown below, a cyanatophenyl-substituted phenyloxy group represented by the formula (3) shown below, a cyanatophenyl-substituted phenyloxy group represented by the formula (4) shown below, a cyanatophenyl-substituted indanoxy group represented by the formula (5) shown below and a cyanatoindane-substituted phenyloxy group represented by the formula (6) shown below:

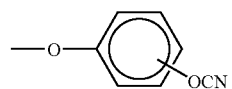

(2)

The cyanatophenyloxy group represented by the formula (2) is, specifically, a 2-cyanatophenyloxy group, a 3-cyanatophenyloxy group or a 4-cyanatophenyloxy group.

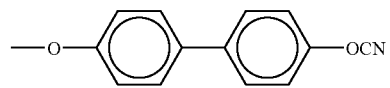

(3)

The cyanatophenyl-substituted phenyloxy group represented by the formula (3) is, specifically, a 4'-cyanatophenyl-4-phenyloxy group.

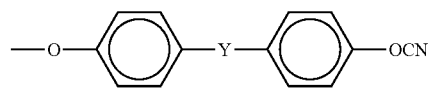

(4)

In the formula (4), Y represents O, S, $SO_2$, $CH_2$, $CHCH_3$, $C(CF_3)_2$, $C(CH_3)CH_2CH_3$ or CO. Therefore, the cyanatophenyl-substituted phenyloxy group represented by the formula (4) is, specifically, a 4'-cyanatophenyloxy-4-phenyloxy group, a 4'-cyanatophenylthio-4-phenyloxy group, a 4'-cyanatophenylsulfonyl-4-phenyloxy group, a 4' cyanatobenzyl-4-phenyloxy group, a 4'-cyanatophenylethylidene-4-phenyloxy group, a 4'-cyanatophenylisopropylidene-4-phenyloxy group, a 4'-cyanatophenylhexafluoroisopropylidene-4-phenyloxy group, a 4'-cyanatophenyl(1'-methylpropylidene)-4-phenyloxy group or a 4'-cyanatobenzoyl-4-phenyloxy group.

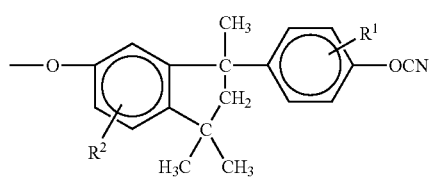

(5)

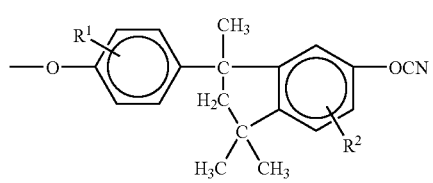

(6)

In the formulas (5) and (6), $R^1$ and $R^2$ represent a hydrogen atom, an alkyl group having 1 to 4 carbon atoms, a cycloalkyl group or a phenyl group. In the case of the alkyl group, the cycloalkyl group or the phenyl group, the same or different kind of each group may be bonded multiply to the corresponding ring structure.

Examples of the cyanatophenyl-substituted indanoxy group represented by the formula (5) and the cyanatoindan-substituted phenyloxy group represented by the formula (6) include those corresponding to a residue in which one hydroxyl group is substituted with a cyanato group and hydrogen is eliminated from the other hydroxyl group in indane compounds having two hydroxyl groups, such as 1,3,3-trimethyl-1-(4-hydroxyphenyl)indan-6-ol, 1,3,3-trimethyl-1-(4-hydroxy-3-methylphenyl)indan-6-ol, 1,3,3-trimethyl-1-(4-hydroxy-3,5-di-tert-butylphenyl)indan-6-ol, 1,3,3-trimethyl-5-tert-butyl-1-(4-hydroxy-3-tert-butylphenyl)indan-6-ol, 1,3,3-trimethyl-5-tert-butyl-1-(4-hydroxy-3,5-di-tert-butylphenyl)indan-6-ol, 1,3,3-trimethyl-5-isopropyl-1-(4-hydroxy-3-iso-propylphenyl)indan-6-ol and 1,3,3-trimethyl-5-phenyl-1-(4-hydroxy-3-phenylphenyl)indan-6-ol. Examples of the cyanatophenyl-substituted indanoxy group represented by the formula (5) include those corresponding to a residue in which a hydroxyl group bonded at the 1-position of indane or a hydroxyl group of a substituted hydroxyphenyl group is substituted with a cyanatophenyl group, and hydrogen is eliminated from a hydroxyl group bonded at the 6-position of indane, in various indane compounds described above. Examples of the hydroxyindane-substituted phenyloxy group represented by the formula (6) include those corresponding to a residue in which a hydroxyl group bonded at the 6-position of indane is substituted with a cyanato group, and hydrogen is eliminated from a phenol group bonded at the 1-position of indane or a hydroxyl group of a substituted phenol group, in various indane compound described above.

Preferred A3 groups described above include a 4-cyanatophenyloxy group, a 4'-cyanatophenyl-4-phenyloxy group, a 4'-cyanatophenyloxy-4-phenyloxy group, a 4'-cyanatophenylthio-4-phenyloxy group, a 4'-cyanatophenylsulfonyl-4-phenyloxy group, a 4'-cyanatophenylisopropylidene-4-phenyloxy group, a 4'-cyanatophenylhexafluoroisopropylidene-4-phenyloxy group, a 4'-cyanatobenzoyl-4-phenyloxy group, and those corresponding to a residue in which one of two hydroxyl groups of 1,3,3-trimethyl-1-(4-hydroxyphenyl)indan-6-ol and 1,3,3-trimethyl-1-(4-hydroxy-3-methylphenyl)indan-6-ol is substituted with a cyanato group and hydrogen is eliminated from the other hydroxyl group. Among these groups, a 4-cyanatophenyloxy group, a 4'-cyanatophenyl-4-phenyloxy group, a 4'-cyanatophenyloxy-4-phenyloxy group, a 4'-cyanatophenylsulfonyl-4-phenyloxy group, a 4'-cyanatophenylisopropylidene-4-phenyloxy group, and a group corresponding to a residue in which one of two hydroxyl groups of 1,3,3-trimethyl-1-(4-hydroxyphenyl)indan-6-ol is substituted with a cyanato group and hydrogen is eliminated from the other hydroxyl group are particularly preferred.

In the formula (1), 2n A groups are contained and at least one of them is an A3 group. Therefore, the cyanato group-containing cyclic phosphazene compound represented by the formula (1) of the present invention can be classified roughly into the following types.

[Type 1]

All 2n A groups are A3 groups. In this case, all A groups may be the same A3 groups, or two or more kinds of A3 groups.

Specific examples of the cyanato group-containing cyclic phosphazene compound of this type include a cyanato group-containing cyclotriphosphazene compound in which n in the formula (1) is 3, a cyanato group-containing cyclotetraphosphazene compound in which n in the formula (1) is 4, a cyanato group-containing cyclopentaphosphazene compound in which n in the formula (1) is 5, and a cyanato group-containing cyclohexaphosphazene compound in which n in the formula (1) is 6, those in which all A groups are one kind of A3 group selected from the group of A3 groups of a 4-cyanatophenyloxy group, a 4'-cyanatophenyl-4-phenyloxy group, 4'-cyanatophenyloxy-4-phenyloxy group, a 4'-cyanatophenylthio-4-phenyloxy group, a 4'-cyanatophenylsulfonyl-4-phenyloxy group, a 4'-cyanatophenylisopropylidene-4-phenyloxy group, a 4'-cyanatobenzoyl-4-phenyloxy group and those corresponding to a residue in which one hydroxyl group of two hydroxyl groups of 1,3,3-trimethyl-1-(4-hydroxyphenyl)indan-6-ol and 1,3,3-trimethyl-1-(4-hydroxy-3-methylphenyl)indan-6-ol is substitute with a cyanato group and hydrogen is eliminated from the other hydroxyl group, and those in which all A groups are two or more kinds of A3 groups selected from the group of the same A3 groups, and any mixture thereof.

[Type 2]

A portion (that is, at least one) of 2n A groups is an A3 group and the other A groups are groups selected from an A1 group and an A2 group. In this case, all A groups other than the A3 group may be the same A1 group or A2 group, or two or more kinds of the A1 group or the A2 group, or one or more kinds of the A1 group along with one or more kinds of the A2 group.

Preferred cyanato group-containing cyclic phosphazene compounds of this type include those in which 2 to (2n−2) A groups of 2n A groups are A3 groups. Particularly preferred cyanato group-containing cyclic phosphazene compounds of this type are a cyanato group-containing cyclotriphosphazene compound in which n in the formula (1) is 3, a cyanato group-containing cyclotetraphosphazene compound in which n in the formula (1) is 4, a cyanato group-containing cyclopentaphosphazene compound in which n in the formula (1) is 5, a cyanato group-containing cyclohexaphosphazene compound in which n in the formula (1) is 6, those in which 2 to (2n−2) A groups of 2n A groups are A3 groups, and any mixture thereof. This kind of a cyanato group-containing cyclic phosphazene compound is advantageous in that it can realize a resin molded product which is more excellent in thermal reliability and mechanical strength (particularly, glass transition temperature) as compared with other cyanato group-containing cyclic phosphazene compounds of the present invention.

It can be confirmed by TOF-MS analysis of a cyanato group-containing cyclic phosphazene compound or an intermediate thereof in the production process whether or not 2 to (2n−2) A groups of 2n A groups are A3 groups.

Specific examples of the cyanato group-containing cyclic phosphazene compound of this type include a cyanato group-containing cyclotriphosphazene compound in which n in the formula (1) is 3, a cyanato group-containing cyclotetraphosphazene compound in which n in the formula (1) is 4, a cyanato group-containing cyclopentaphosphazene compound in which n in the formula (1) is 5, and a cyanato group-containing cyclohexaphosphazene compound in which n in the formula (1) is 6, wherein a group of A is composed of: a combination of a 4-cyanatophenyloxy group as the A3 group and an n-propoxy group as the A1 group; a combination of a 4-cyanatophenyloxy group as the A3 group and a phenoxy group as the A2 group; a combination of a 4-cyanatophenyloxy group as the A3 group and a methylphenoxy group as the A2 group; a combination of a 4'-cyanatophenyl-4-phenyloxy group as the A3 group and an n-propoxy group as the A1 group; a combination of a 4'-cyanatophenyl-4-phenyloxy group as the A3 group and a phenoxy group as the A2 group; a combination of a 4'-cyanatophenyl-4-phenyloxy group as the A3 group and a methylphenoxy group as the A2 group; a combination of a 4'-cyanatophenyl-4-phenyloxy group as the A3 group and a methylphenoxy group as the A2 group; a combination of a 4'-cyanatophenylsulfonyl-4-phenyloxy group as the A3 group and an n-propoxy group as the A2 group; a combination of a 4'-cyanatophenylsulfonyl-4-phenyloxy group as the A3 group and a phenoxy group as the A2 group; a combination of a 4'-cyanatophenylsulfonyl-4-phenyloxy group as the A3 group and a methylphenoxy group as the A2 group; a combination of a 4'-cyanatophenylisopropylidene-4-phenyloxy group as the A3 group and an n-propoxy group as the A1 group; a combination of a 4'-cyanatophenylisopropylidene-4-phenyloxy group as the A3 group and a phenoxy group as the A2 group; a combination of a 4'-cyanatophenylisopropylidene-4-phenyloxy group as the A3 group and a methylphenoxy group as the A2 group; a combination of those corresponding to a residue in which one hydroxyl group of two hydroxyl groups of 1,3,3-trimethyl-1-(4-hydroxyphenyl)indan-6-ol is substituted with a cyanato group and hydrogen is eliminated from the other hydroxyl group, as the A3 group, and an n-propoxy group as the A2 group; a combination of those corresponding to a residue in which one hydroxyl group of two hydroxyl groups of 1,3,3-trimethyl-1-(4-hydroxyphenyl)indan-6-ol is substituted with a cyanato group and hydrogen is eliminated from the other hydroxyl group, as the A3 group, and a phenoxy group as the A2 group; or a combination of those corresponding to a residue in which one hydroxyl group of two hydroxyl groups of 1,3,3-trimethyl-1-(4-hydroxyphenyl)indan-6-ol is substituted with a cyanato group and hydrogen is eliminated from the other hydroxyl group, as the A3 group, and a methylphenoxy group as the A2 group; or composed of any mixture of the combinations.

Among them, preferred cyanato group-containing cyclotriphosphazene compounds are a cyanato group-containing cyclotriphosphazene compound in which n in the formula (1) is 3, a cyanato group-containing cyclotetraphosphazene compound in which n in the formula (1) is 4, a cyanato group-containing cyclopentaphosphazene compound in which n in the formula (1) is 5, a cyanato group-containing cyclohexaphosphazene compound in which n in the formula (1) is 6, wherein a group of A is composed of: a combination of a 4-cyanatophenyloxy group as the A3 group and a phenoxy group as the A2 group; a combination of a 4'-cyanatophenyl-4-phenyloxy group as the A3 group and a phenoxy group as the A2 group; a combination of a 4'-cyanatophenylsulfonyl-4-phenyloxy group as the A3 group and a phenoxy group as the A2 group; a combination of a 4'-cyanatophenylsulfonyl-4-phenyloxy group as the A3 group and a methylphenoxy group as the A2 group; a combination of a 4'-cyanatophenylisopropylidene-4-phenyloxy group as the A3 group and a phenoxy group as the A2 group; a combination of a 4'-cyanatophenylisopropylidene-4-phenyloxy group as the A3 group and a methylphenoxy group as the A2 group, a combination of those corresponding to a residue in which one hydroxyl group of two hydroxyl groups of 1,3,3-trimethyl-1-(4-hydroxyphenyl)indan-6-ol is substituted with a cyanato group and hydrogen is eliminated from the other hydroxyl group, as the A3 group, and a phenoxy group as the A2 group; or a combination of those corresponding to a residue in which one hydroxyl group of two hydroxyl groups of 1,3,3-trimethyl-1-(4-hydroxyphenyl)indan-6-ol is substituted with a cyanato group and hydrogen is eliminated from the other hydroxyl group, as the A3 group, and a methylphenoxy group as the A2 group; or composed of any mixture of the combinations. Particularly preferred cyanato group-containing cyclotriphosphazene compounds are a cyanato group-containing cyclotriphosphazene compound in which n in the formula (1) is 3 or a cyanato group-containing cyclotetraphosphazene compound in which n in the formula (1) is 4, wherein a group of A is composed of: a combination of a 4-cyanatophenyloxy group as the A3 group and a phenoxy group as the A2 group; a combination of a 4'-cyanatophenylsulfonyl-4-phenyloxy group as the A3 group and a phenoxy group as the A2 group; a combination of a 4'-cyanatophenylsulfonyl-4-phenyloxy group as the A3 group and a methylphenoxy group as the A2 group; a combination of a 4'-cyanatophenylisopropylidene-4-phenyloxy group as the A3 group and a phenoxy group as the A2 group; or a combination of those corresponding to a residue in which one hydroxyl group of two hydroxyl groups of 1,3,3-trimethyl-1-(4-hydroxyphenyl)indan-6-ol is substituted with a cyanato group and hydrogen is eliminated from the other hydroxyl group, as the A3 group, and a phenoxy group as the A2 group; or composed of any mixture of the combinations.

The cyanato group-containing cyclic phosphazene compounds of the present invention described above are not crosslinked with each other by using a hydroxyl group of a cyclic phosphonitrile-substituted compound as an intermediate obtained in the production method described hereinafter. That is, the cyanato group-containing cyclic phosphazene compounds of the present invention have no crosslinked structure between the cyclic phosphonitrile-substituted compounds having a hydroxyl group, i.e. the intermediates, in the production process. The cyanato group-containing cyclic phosphazene compound of the present invention is novel in this feature and is different from a conventional cyanato group-containing cyclic phosphazene compound.

Method for Production of Cyanato Group-Containing Cyclic Phosphazene Compound

The cyanato group-containing cyclic phosphazene compound of the present invention can be produced by the following method.

First, a cyclic phosphonitrile-dihalide represented by the formula (7) shown below is prepared.

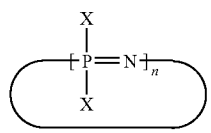

(7)

In the formula (7), n represents an integer of 3 to 15. X represents a halogen atom, and preferably a fluorine atom or a chlorine atom. A cyclic phosphonitrile dihalide prepared herein may be a mixture of several kinds of compounds each having different n.

The method for production of the cyclic phosphonitrile dihalide is described in various documents, for example, documents 11 and 12 below.

Document 11

H. R. ALLCOCK, PHOSPHORUS-NITROGEN COMPOUNDS, ACADEMIC PRESS, (1972).

Document 12

M. GLERIA, R. DE TAEGR, PHOSPHAZENES, A WORLDWIDE INSIGHT, NOVA SCIENCE PUBLISHERS INC., (2004).

As described in these documents, the cyclic phosphonitrile dihalide represented by the formula (7) is usually obtained as a mixture of a cyclic and linear phosphonitrile dihalide having a degree of polymerization of about 3 to 15. Therefore, as described in documents 11 and 12, it is necessary that the cyclic phosphonitrile dihalide represented by the formula (7) is obtained by removing a linear phosphonitrile dihalide from the mixture by utilizing a solubility difference in a solvent, or obtained by separating a cyclic phosphonitrile dihalide from the mixture by distillation or recrystallization.

The cyclic phosphonitrile dihalide used in the method is preferably, for example, hexafluorocyclotriphosphazene (n is 3), octafluorocyclotetraphosphazene (n is 4), decafluorocyclopentaphosphazene (n is 5), dodecafluorocyclohexaphosphazene (n is 6), a mixture of hexafluorocyclotriphosphazene and octafluorocyclotetraphosphazene, a mixture of cyclic phosphonitrile difluorides in which n is from 3 to 15, hexachlorocyclotriphosphazene (n is 3), octachlorocyclotetraphosphazene (n is 4), decachlorocyclopentaphosphazene (n is 5), dodecachlorocyclohexaphosphazene (n is 6), a mixture of hexachlorocyclotriphosphazene and octachlorocyclotetraphosphazene, and a mixture of cyclic phosphonitrile dichlorides in which n is from 3 to 15. Among these cyclic phosphonitrile dihalides, hexachlorocyclotriphosphazene, octachlorocyclotetraphosphazene, a mixture of hexachlorocyclotriphosphazene and octachlorocyclotetraphosphazene, and a mixture of cyclic phosphonitrile dichlorides in which n is from 3 to 15 are more preferred, and hexachlorocyclotriphosphazene, a mixture of hexachlorocyclotriphosphazene and octachlorocyclotetraphosphazene, and a mixture of cyclic phosphonitrile dichlorides in which n is from 3 to 15 are particularly preferred.

Meanwhile, as the compounds used to react with the cyclic phosphonitrile dihalide described above, the following compounds B1, B2 and B3 are prepared.

[Compound B1]

Alcohols having 1 to 8 carbon atoms.

The alcohols may be substituted with at least one group selected from an alkyl group having 1 to 6 carbon atoms, an alkenyl group and an aryl group.

Examples of the alcohols include methanol, ethanol, n-propanol, isopropanol, n-butanol, sec-butanol, tert-butanol, n-pentanol, n-hexanol, n-heptanol, n-octanol, vinyl alcohol, 1-propen-1-ol, 2-propen-1-ol (allyl alcohol), 1-methyl-1-ethen-1-ol, 3-buten-1-ol, 2-methyl-2-propen-1-ol, 4-penten-1-ol, 2-hexen-1-ol, 2-hepten-4-ol, 5-octen-1-ol, benzyl alcohol and phenethyl alcohol. Among these alcohols, methanol, ethanol, n-propanol, allyl alcohol and benzyl alcohol are preferred, and ethanol and n-propanol are particularly preferred.

[Compound B2]

Phenols having 6 to 20 carbon atoms. The phenols may be substituted with at least one group selected from an alkyl group having 1 to 6 carbon atoms, an alkenyl group and an aryl group.

Examples of the phenols include phenol, cresol, dimethylphenol, ethylphenol, ethylmethylphenol, diethylphenol, n-propylphenol, isopropylphenol, isopropylmethylphenol, isopropylethylphenol, diisopropylphenol, n-butylphenol, sec-butylphenol, tert-butylphenol, n-pentylphenol, n-hexylphenol, vinylphenol, 1-propenylphenol, 2-propenylphenol, isopropenylphenol, 1-butenylphenol, sec-butenylphenol, 1-pentenylphenol, 1-hexenylphenol, phenylphenol, naphthol, anthranol and phenanthranol. Among these phenols, phenol, cresol, dimethylphenol, diethylphenol, 2-propenylphenol, phenylphenol and naphthols are preferred, and phenol, cresol, dimethylphenol and naphthols are particularly preferred.

[Compound B3]

Five kinds of the following protected diphenols, B3-1, B3-2, B3-3, B3-4 and B3-5.

Compound B3-1

Protected diphenols represented by the following formula (13) in which one hydroxyl group is substituted with a protecting group.

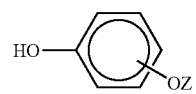

(13)

In the formula (13), Z represents a protecting group capable of forming an OH group when eliminated.

The protected diphenols can be obtained by protecting one hydroxyl group of a diphenol compound represented by the following formula (14), that is, catechol, resorcinol or hydroquinone with the above protecting group.

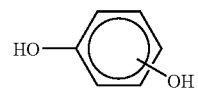

(14)

Compound B3-2

Protected diphenols represented by the following formula (15) in which one hydroxyl group is protected with a protecting group.

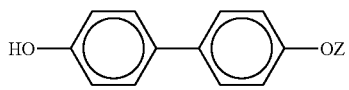

(15)

In the formula (15), Z represents a protecting group capable of forming an OH group when eliminated.

The protected diphenols can be obtained by protecting one hydroxyl group of a diphenol compound represented by the following formula (16), that is, 4,4'-diphenol with a protecting group.

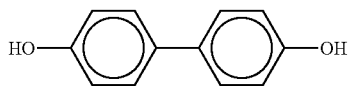

(16)

Compound B3-3

Protected phenols represented by the following formula (17) in which one hydroxyl group is protected with a protecting group.

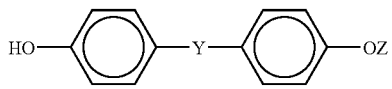

(17)

In the formula (17), Z represents a protecting group capable of forming an OH group when eliminated. Y is the same as that in the formula (18) which will be described below.

The protected diphenols can be obtained by protecting one hydroxyl group of a diphenol compound represented by the following formula (18) with the above protecting group.

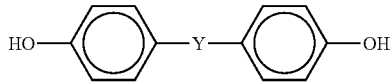

(18)

In the formula (18), Y represents O, S, $SO_2$, $CH_2$, $CHCH_3$, $C(CH_3)_2$, $C(CF_3)_2$, $C(CH_3)CH_2CH_3$, or CO. The diphenols represented by the formula (18) are specifically 4,4'-oxydiphenol, 4,4'-thiodiphenol, 4,4'-sulfonyl diphenol (bisphenol-S), 4,4'-methylenediphenol (bisphenol-F), 4,4'-ethylidenediphenol, 4,4'-isopropylidenediphenol (bisphenol-A), 4,4'-hexafluoroisopropylidenediphenol (bisphenol-AF), 4,4'-(1-methylpropylidene)diphenol (bisphenol-B) and 4,4-dihydroxybenzophenone.

Compound B3-4

Protected diphenols represented by the following formula (19) in which one hydroxyl group, that is, a hydroxyl group of a 4-hydroxyphenyl group at the 1-position of indane is protected with a protecting group.

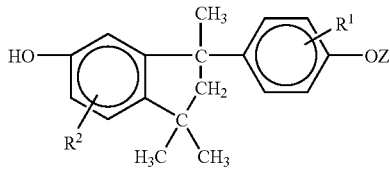

(19)

In the formula (19), Z represents a protecting group capable of forming an OH group when eliminated. $R^1$ and $R^2$ are the same as those in the formula (20) which will be described below.

The protected diphenols can be obtained by protecting a hydroxyl group of a 4-hydroxyphenyl group at the 1-position of indane with the above protecting group in a diphenol compound represented by the following formula (20).

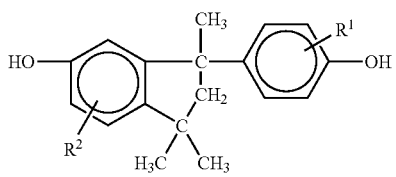

(20)

In the formula (20), $R^1$ and $R^2$ represent a hydrogen atom, an alkyl group having 1 to 4 carbon atoms, a cycloalkyl group or a phenyl group. In the case of the alkyl group, the cycloalkyl group or the phenyl group, the same or different kind of each group may be bonded multiply to the corresponding ring structure. The diphenols represented by the formula (20) are 1,3,3-trimethyl-1-(4-hydroxyphenyl)indan-6-ol or alkyl, cycloalkyl or phenyl derivatives thereof obtained by a cyclization reaction of a linear dimer of p-isopropenylphenol, that is, a mixture of 2,4-di(4-hydroxyphenyl)-4-methyl-pentene-1 and 2,4-di(4-hydroxyphenyl)-4-methyl-pentene-2 in the presence of an acid catalyst. Specific examples thereof include 1,3,3-trimethyl-1-(4-hydroxyphenyl)indan-6-ol, 1,3,3-trimethyl-1-(4-hydroxy-3-methylphenyl)indan-6-ol, 1,3,3-trimethyl-1-(4-hydroxy-3,5-di-tert-butylphenyl)indan-6-ol, 1,3,3-trimethyl-5-tert-butyl-(4-hydroxy-3-tert-butylphenyl)indan-6-ol, 1,3,3-trimethyl-5-tert-butyl-1-(4-hydroxy-3,5-di-tert-butylphenyl)indan-6-ol, 1,3,3-trimethyl-5-iso-propyl-1-(4-hydroxy-3-iso-propylphenyl)indan-6-ol and 1,3,3-trimethyl-5-phenyl-1-(4-hydroxy-3-phenylphenyl)indan-6-ol.

Compound B3-5

Protected diphenols represented by the following formula (21) in which one hydroxyl group, that is, a hydroxyl group at the 6-position of indane is protected with a protecting group.

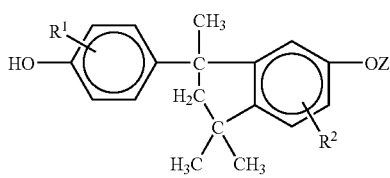

(21)

In the formula (21), Z represents a protecting group capable of forming an OH group when eliminated. $R_1$ and $R_2$ are the same as those in the above formula (20).

The protected diphenols can be obtained by protecting a hydroxyl group at the 6-position of indane with the above protecting group in a diphenol compound represented by the above formula (20).

In five kinds of protected diphenols of the compounds B3-1, B3-2, B3-3, B3-4 and B3-5 described above, that is, protected diphenols represented by the formulas (13), (15), (17), (19) and (21), the kinds of a protecting group represented by Z are described in a lot of known documents such as documents 13 and 14 below. The method of selectively preparing protected diphenols represented by the formulas (13), (15), (17) and (19) or (21) from diphenols represented by the formulas (14), (16), (18) and (20) is also described in documents 13 and 14.

Document 13

T. W. GREEN, P. G. M. WUTS, PROTECTIVE GROUPS IN ORGANIC SYNTHESIS, WILEY-INTERSCIENCE, (1999).

Document 14

J. ROBERTSON, PROTECTING GROUP CHEMISTRY (OXFORD CHEMISTRY PRIMERS), OXFORD UNIVERSITY PRESS, (2000).

Specific examples of the protecting group represented by Z include a methyl group, a methoxymethyl group, a methylthiomethyl group, a 2-methoxyethoxymethyl group, a tetrahydropyranyl group, a tetrahydrothiopyranyl group, a 4-methoxytetrahydropyranyl group, a 4-methoxytetrahydrothiopyranyl group, a tetrahydrofuranyl group, a tetrahydrothiofuranyl group, a 1-ethoxyethyl group, a tert-butyl group, an allyl group, a benzyl group, an o-nitrobenzyl group, a triphenylmethyl group, a trimethylsilyl group, a tert-butyldimethylsilyl group, a tert-butyldiphenylsilyl group, a tribenzylsilyl group and a triisopropylsilyl group. Among these protecting groups, a methyl group, a methoxymethyl group, a tetrahydropyranyl group, a 4-methoxytetrahydropyranyl group, a tert-butyl group, an allyl group, a benzyl group and a tert-butyldimethylsilyl group are preferred, and a methyl group, a methoxymethyl group, a tert-butyl group, an allyl group and a benzyl group are particularly preferred.

Specific examples of the above-described compounds B3-1, B3-2, B3-3, B3-4 and B3-5 are as follows.

[Compound B3-1]

2-methoxyphenol, 2-methoxymethoxyphenol, 2-tert-butyloxyphenol, 2-allyloxyphenol, 2-benzyloxyphenol, 3-methoxyphenol, 3-methoxymethoxyphenol, 3-tert-butyloxyphenol, 3-allyloxyphenol, 3-benzyloxyphenol, 4-methoxyphenol, 4-methoxymethoxyphenol, 4-tert-butyloxyphenol, 4-allyloxyphenol, 4-benzyloxyphenol, etc.

[Compound B3-2]

4'-methoxyphenyl-4-phenol, 4'-methoxymethoxyphenyl-4-phenol, 4'-tert-butyloxyphenyl-4-phenol, 4'-allyloxyphenyl-4-phenol, 4'-benzyloxyphenyl-4-phenol, etc.

[Compound B3-3]

4'-methoxyphenyloxy-4-phenol, 4'-methoxymethoxyphenyloxy-4-phenol, 4'-tert-butyloxyphenyloxy-4-phenol, 4'-allyloxyphenyloxy-4-phenol, 4'-benzyloxyphenyloxy-4-phenol, 4'-methoxyphenylthio-4-phenol, 4'-methoxymethoxyphenylthio-4-phenol, 4'-tert-butyloxyphenylthio-4-phenol, 4'-allyloxyphenylthio-4-phenol, 4'-benzyloxyphenylthio-4-phenol, 4'-methoxyphenylsulfonyl-4-phenol, 4'-methoxymethoxyphenylsulfonyl-4-phenol, 4'-tert-butyloxyphenylsulfonyl-4-phenol, 4'-allyloxyphenylsulfonyl-4-phenol, 4'-benzyloxyphenylsulfonyl-4-phenol, 4'-methoxybenzyl-4-phenol, 4'-methoxymethoxybenzyl-4-phenol, 4'-tert-butyloxybenzyl-4-phenol, 4'-allyloxybenzyl-4-phenol, 4'-benzyloxybenzyl-4-phenol, 4'-methoxyphenylethyl-4-phenol, 4'-methoxymethoxyphenylethyl-4-phenol, 4'-tert-butyloxyphenylethyl-4-phenol, 4'-allyloxyphenylethyl-4-phenol, 4'-benzyloxyphenylethyl-4-phenol, 4'-methoxyphenylisopropylidene-4-phenol, 4'-methoxymethoxyphenylisopropylidene-4-phenol, 4'-tert-butyloxyphenylisopropylidene-4-phenol, 4'-allyloxyphenylisopropylidene-4-phenol, 4'-benzyloxyphenylisopropylidene-4-phenol, 4'-methoxyphenyl(1-methylpropylidene)-4-phenol, 4'-methoxymethoxyphenyl(1-methylpropylidene)-4-phenol, 4'-tert-butyloxyphenyl(1-methylpropylidene)-4-phenol, 4'-allyloxyphenyl(1-methylpropylidene)-4-phenol, 4'-benzyloxyphenyl(1-methylpropylidene)-4-phenol, 4'-methoxybenzoyl-4-phenol, 4'-methoxymethoxybenzoyl-4-phenol, 4'-tert-butyloxybenzoyl-4-phenol, 4'-allyloxybenzoyl-4-phenol, 4'-benzyloxybenzoyl-4-phenol, etc.

[Compound B3-4]

1,3,3-trimethyl-1-(4-methoxyphenyl)indan-6-ol, 1,3,3-trimethyl-1-(4-methoxymethoxyphenyl)indan-6-ol, 1,3,3-trimethyl-1-(4-tert-butyloxyphenyl)indan-6-ol, 1,3,3-trimethyl-1-(4-allyloxyphenyl)indan-6-ol, 1,3,3-trimethyl-1-(4-benzyloxyphenyl)indan-6-ol, etc.

[Compound B3-5]

1,3,3-trimethyl-1-(4-hydroxyphenyl)-6-methoxyindane, 1,3,3-trimethyl-1-(4-hydroxyphenyl)-6-methoxymethoxyindane, 1,3,3-trimethyl-1-(4-hydroxyphenyl)-6-tert-butyloxyindane, 1,3,3-trimethyl-1-(4-hydroxyphenyl)-6-allyloxyindane, 1,3,3-trimethyl-1-(4-hydroxyphenyl)-6-benzyloxyindane, etc.

As the compounds B3-1, B3-2, B3-3, B3-4 and B3-5, commercially available compounds and those produced in accordance with known methods such as methods described in the above documents 13 and 14 can be used.

In the method of producing the cyanato group-containing cyclic phosphazene compound of the present invention, first, by reacting the above-described cyclic phosphonitrile dihalide represented by the formula (7) with the above-described compounds B1 to B3, all halogen atoms of the cyclic phosphonitrile dihalide are substituted with a group selected from the group consisting of the following E1 group, E2 group and E3 group so as to substitute at least one of the halogen atoms with the E3 group, a cyclic phosphonitrile-substituted compound is produced (step A).

[E1 Group]

Alkoxy group having 1 to 8 carbon atoms which may be substituted with at least one group selected from an alkyl group having 1 to 6 carbon atoms, an alkenyl group and an aryl group.

This group is substituted with a halogen atom by a compound B1, and corresponds to the A1 group described above.

[E2 Group]

Aryloxy group having 6 to 20 carbon atoms which may be substituted with at least one group selected from an alkyl group having 1 to 6 carbon atoms, an alkenyl group and an aryl group.

This group is substituted with a halogen atom by a compound B2, and corresponds to the A2 group described above.

[E3 Group]

Group selected from the group consisting of a substituted phenyloxy group represented by the formula (8) shown below, a substituted phenyloxy group represented by the formula (9) shown below, a substituted phenyloxy group represented by the formula (10) shown below, a substituted indanoxy group represent by the formula (11) shown below and a substituted phenyloxy group represent by the formula (12) shown below.

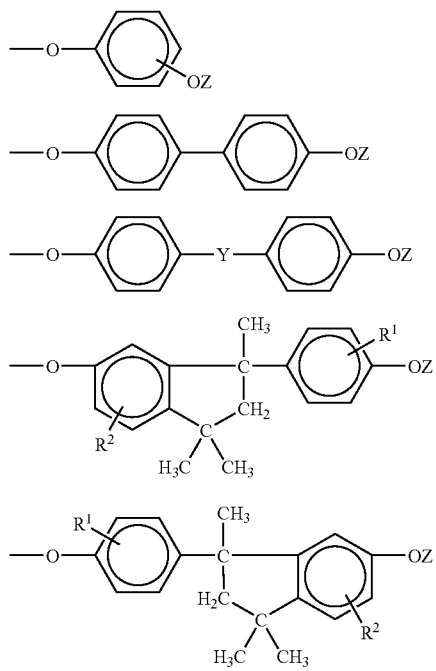

In the formulas (8) to (12), Z represents a protecting group capable of forming an OH group when eliminated, and is specifically the same as those described about five kinds of protected diphenols of the compounds B3-1, B3-2, B3-3, B3-4 and B3-5 described above. In the formula (8), an —OZ group is substituted on the ortho-, meta- or para-position. In the formula (10), Y represents O, S, $SO_2$, $CH_2$, $CHCH_3$, $C(CH_3)_2$, $C(CF_3)_2$, $C(CH_3)CH_2CH_3$ or CO. Furthermore, in the formulas (11) and (12), $R^1$ and $R^2$ represent a hydrogen atom, an alkyl group having 1 to 4 carbon atoms, a cycloalkyl group or a phenyl group.

In the production process, compounds B1 to B3 are appropriately selected due to the kind of the cyanato group-containing cyclic phosphazene compound to be produced. In other words, compounds B1 to B3 are appropriately selected owing to either a production of a cyanato group-containing cyclic phosphazene compound of the above type 1 or a cyanato group-containing cyclic phosphazene compound of the above type 2. Specific description is made as follows.

[Case of Producing Cyanato Group-Containing Cyclic Phosphazene Compound of Type 1]

In this case, a cyclic phosphonitrile dihalide is reacted with a compound B3 to substitute all halogen atoms (hereinafter sometimes referred to as active halogen atoms) of the cyclic phosphonitrile dihalide with an E3 group derived from the compound B3. One or more kinds of five kinds of the above protected diphenol compounds B3-1, B3-2, B3-3, B3-4 and B3-5 are used herein as the compound B3. As the method of reacting the cyclic phosphonitrile dihalide with the compound B3 to substitute all active halogen atoms of the cyclic phosphonitrile dihalide with the E3 group, for example, any of the following methods can be employed.

<Method 1-A>

A cyclic phosphonitrile dihalide is reacted with an alkali metal salt of a compound B3.

According to this method, the amount of the alkali metal salt of the compound B3 to be used is preferably set within a range from 1.0 to 2.0 equivalents, and more preferably from 1.05 to 1.3 equivalents, based on the amount of the active halogen atoms of the cyclic phosphonitrile dihalide. If the amount used is less than 1.0 equivalents, a portion of active halogen atoms may be remained and the objective cyanato group-containing cyclic phosphazene compound may not exhibit the intended result. In contrast, if the amount used is more than 2.0 equivalents, it may become difficult to separate and purify the reaction product, and also the process tends to be uneconomical.

<Method 1-B>

A cyclic phosphonitrile dihalide is reacted with a compound B3 in the presence of a base capable of scavenging a hydrogen halide.

According to this method, the amount of the compound B3 to be used is preferably set within a range from 1.0 to 2.0 equivalents, and more preferably from 1.05 to 1.3 equivalents, based on the amount of the active halogen atoms of the cyclic phosphonitrile dihalide. If the amount used is less than 1.0 equivalents, a portion of active halogen atoms may be remained and the objective cyanato group-containing cyclic phosphazene compound may not exhibit the intended result. In contrast, if the amount used is more than 2.0 equivalents, it may become difficult to separate and purify the reaction product, and also the process tends to be uneconomical. The amount of the base to be used is preferably set within a range from 1.1 to 2.1 equivalents, and more preferably from 1.1 to 1.4 equivalents, based on the amount of the active halogen atoms of the cyclic phosphonitrile dihalide. If the amount used is less than 1.1 equivalents, a portion of active halogen atoms may be remained and the objective cyanato group-containing cyclic phosphazene compound may not exhibit the intended result. In contrast, if the amount used is more than 2.1 equivalents, it may become difficult to separate and purify the reaction product, and also the process tends to be uneconomical.

[Case of Producing Cyanato Group-Containing Cyclic Phosphazene Compound of Type 2]

In this case, a cyclic phosphonitrile dihalide is reacted with at least one of those of a compound B3 along with at least one of compounds of a compound B1 and a compound B2 to substitute a portion of active halogen atoms of the cyclic phosphonitrile dihalide with an E3 group derived from the compound B3 and also substitute all of remaining active halogen atoms with at least one of the groups of an E1 group derived from the compound B1 and an E2 group derived from the compound B2. As the method, any of the following methods can be employed.

<Method 2-A>

A cyclic phosphonitrile dihalide is reacted with a mixture of an alkali metal salt of a compound B3 and an alkali metal salt of at least one of compounds of a compound B1 and a compound B2 to substitute all active halogen atoms. In the mixture, the proportion of the alkali metal salt of the compound B3 can be appropriately set depending on the kind of the cyanato group-containing cyclic phosphazene compound to be produced.

According to this method, the amount of the above mixture to be used is preferably set within a range from 1.0 to 2.0 equivalents, and more preferably from 1.05 to 1.3 equivalents, based on the amount of the active halogen atoms of the cyclic phosphonitrile dihalide. If the amount used is less than 1.0 equivalents, a portion of active halogen atoms may be remained and the objective cyanato group-containing cyclic phosphazene compound may not exhibit the intended result. In contrast, if the amount used is more than 2.0 equivalents, it may become difficult to separate and purify the reaction product, and also the process tends to be uneconomical.

<Method 2-B>

A cyclic phosphonitrile dihalide is reacted with a mixture of a compound B3 and at least one of the compounds of a compound B1 and a compound B2 in the presence of a base capable of scavenging a hydrogen halide to substitute all active halogen atoms. In the mixture, the proportion of the compound B3 can be appropriately set depending on the kind of the cyanato group-containing cyclic phosphazene compound to be produced.

According to this method, the amount of the mixture to be used is preferably set within a range from 1.0 to 2.0 equivalents, and more preferably from 1.05 to 1.3 equivalents, based on the amount of the active halogen atoms of the cyclic phosphonitrile dihalide. If the amount used is less than 1.0 equivalents, a portion of active halogen atoms may be remained and the objective cyanato group-containing cyclic phosphazene compound may not exhibit the intended result. In contrast, if the amount used is more than 2.0 equivalents, it may become difficult to separate and purify the reaction product, and also the process tends to be uneconomical. The amount of the base to be used is preferably set within a range from 1.1 to 2.1 equivalents, and more preferably from 1.1 to 1.4 equivalents, based on the amount of the active halogen atoms of the cyclic phosphonitrile dihalide. If the amount used is less than 1.1 equivalents, a portion of active halogen atoms may be remained and the objective cyanato group-containing cyclic phosphazene compound may not exhibit the intended result. In contrast, if the used amount is more than 2.1 equivalents, it may become difficult to separate and purify the reaction product, and also the process tends to be uneconomical.

<Method 2-C>

First, a cyclic phosphonitrile dihalide is reacted with a compound B3 to obtain a partially substituted compound in which a portion of active halogen atoms of the cyclic phosphonitrile dihalide is substituted with an E3 group derived from the compound B3 (first step). Then, the resultant partially substituted compound is reacted with at least one of the compounds of a compound B1 and a compound B2 to substitute all remaining active halogen atoms with at least one of the groups of an E1 group derived from the compound B1 and an E2 group derived from the compound B2 (second step).

The first step of this method may be carried out by reacting the cyclic phosphonitrile dihalide with an alkali metal salt of the compound B3, or reacting the cyclic phosphonitrile dihalide with the compound B3 in the presence of a base capable of scavenging a hydrogen halide. The second step may be carried out by reacting the partially substituted compound obtained in the first step with an alkali metal salt of at least one of the compounds of a compound B1 and a compound B2, or reacting the partially substituted compound obtained in the first step with at least one of the compounds of a compound B1 and a compound B2 in the presence of a base capable of scavenging a hydrogen halide.

<Method 2-D>

First, a cyclic phosphonitrile dihalide is reacted with at least one of the compounds of a compound B1 and a compound B2 to obtain a partially substituted compound in which a portion of active halogen atoms of the cyclic phosphonitrile dihalide is substituted with at least one of the groups of an E1 group derived from the compound B1 and an E2 group derived from the compound B2 (first step). Then, the resultant partially substituted compound is reacted with a compound B3 to substitute all remaining active halogen atoms with an E3 group derived from the compound B3 (second step).

The first step of this method may be carried out by reacting the cyclic phosphonitrile dihalide with an alkali metal salt of at least one of the compounds of a compound B1 and a compound B2, or reacting the cyclic phosphonitrile dihalide with at least one of the compounds of a compound B1 and a compound B2 in the presence of a base capable of scavenging a hydrogen halide. The second step may be carried out by reacting the partially substituted compound obtained in the first step with an alkali metal salt of the compound B3, or reacting the partially substituted compound obtained in the first step with the compound B3 in the presence of a base capable of scavenging a hydrogen halide.

The alkali metal salt used in each method described above is usually preferably a lithium salt, a sodium salt, a potassium salt or a cesium salt. A sodium salt and a potassium salt are particularly preferred. Such an alkali metal salt can be obtained by the dehydrogenation reaction of the compounds B1 to B3 with metallic lithium, metallic sodium or metallic potassium, or the dehydration reaction from a mixture of the compounds B1 to B3 with an alkali metal hydroxide such as lithium hydroxide, sodium hydroxide and potassium hydroxide.

Examples of the base used preferably in the above respective methods include, but are not limited to, aliphatic or aromatic amines such as trimethylamine, triethylamine, diisopropylethylamine, dimethylaniline, diethylaniline, diisopropylaniline, pyridine, 4-dimethylaminopyridine, 4-diethylaminopyridine and 4-diisopropylaminopyridine; alkali metal carboxylates such as sodium carbonate, potassium carbonate, sodium hydrogen carbonate and potassium hydrogen carbonate; and alkali metal hydroxides such as sodium hydroxide, potassium hydroxide and lithium hydroxide. Among these bases, alkali metal hydroxides such as triethylamine, pyridine and sodium hydroxide are particularly preferred.

The reaction of the cyclic phosphonitrile dihalide with the compounds B1 to B3 can be carried out with or without using a solvent with respect to any method described above. In the case of using the solvent, there is no limitation on kind of the solvent as long as the solvent does not exert an adverse influence on the reaction. It is usually preferable to use ether-type organic solvents such as diethylether, tetrahydrofuran, 1,4-dioxane, 1,2-dimethoxyethane, butylmethylether, diisopropylether, 1,2-diethoxyethane and diphenylether; aromatic hydrocarbon-type organic solvents such as benzene, toluene, chlorobenzene, nitrobenzene, xylene, ethylbenzene and isopropylbenzene; halogenated hydrocarbon-type organic solvents such as chloroform and methylene chloride; aliphatic hydrocarbon-type organic solvents such as pentane, hexane, cyclohexane, heptane, octane, nonane, undecane and dodecane; heterocyclic aromatic hydrocarbon-type organic solvents such as pyridine; and tertiary amine-type and cyanogen compound-type organic solvents. It is particularly preferable to use an ether-type organic solvent which has an ether bond in the molecule and also exhibits high solubility of the compounds B1 to B3 and alkali metal salts thereof, and an aromatic hydrocarbon-based organic solvent which is easily separated from water.

The reaction temperature of the reaction of the above cyclic phosphonitrile dihalide with the compounds B1 to B3 varies depending on any method described above, or can be appropriately set taking account of thermostability of the reaction product. When the reaction is carried out using a solvent, the reaction temperature is preferably set within a range from −20° C. to a boiling point of the solvent. When the reaction is carried out without using the solvent, the reaction temperature is preferably set within a range from 40 to 200° C.

When those according to the above type 2, particularly those in which 2 to (2n−2) A groups of 2n A groups in the formula (1) are A3 groups are produced as the cyanato group-containing cyclic phosphazene compound of the present invention, the above method 2-C or 2-D is preferably employed.

When the method 2-C is employed, first, an ether-type solvent solution or an aromatic hydrocarbon-type solvent solution of a cyclic phosphonitrile dihalide is prepared. Then, to the solvent solution, an ether-type solvent solution or an aromatic hydrocarbon-type solvent solution of an alkali metal salt of a compound B3, or an ether-type solvent solution or an aromatic hydrocarbon-type solvent solution of a compound B3 and a base capable of scavenging a hydrogen halide is usually added at a temperature of −20 to 50° C. over 3 to 24 hours, and the reaction is carried out within the same temperature range for 1 to 24 hours to produce a partially substituted compound in which a portion of active halogen atoms of the cyclic phosphonitrile dihalide is substituted with an E3 group derived from the compound B3. Then, to an ether-type solvent solution or an aromatic hydrocarbon-type solvent solution of the resultant partially substituted compound, an ether-type solvent solution or an aromatic hydrocarbon-type solvent solution of an alkali metal salt of at least one compound selected from a compound B1 and a compound B2, or an ether-type solvent solution or an aromatic hydrocarbon-type solvent solution of at least one compound selected from a compound B1 and a compound B2 and a base capable of scavenging a hydrogen halide is usually added at a temperature of 0 to 50° C. over 3 to 24 hours. Then, the reaction is carried out at a temperature of 0° C. to a boiling point of the solvent to substitute all remaining active halogen atoms with at least one of an E1 group derived from the compound B1 and an E2 group derived from the compound B2.

When the method 2-D is employed, first, an ether-type solvent solution or an aromatic hydrocarbon-type solvent solution of a cyclic phosphonitrile dihalide is prepared. Then, to the solvent solution, an ether-type solvent solution or an aromatic hydrocarbon-type solvent solution of an alkali metal salt of at least one compound selected from a compound B1 and a compound B2, or an ether-type solvent solution or an aromatic hydrocarbon-type solvent solution of at least one compound selected from a compound B1 and a compound B2 and a base capable of scavenging a hydrogen halide is usually added at a temperature of −20 to 50° C. over 3 to 24 hours, and then the reaction is carried out within the same temperature range for 1 to 24 hours to produce a partially substituted compound in which a portion of active halogen atoms of the cyclic phosphonitrile dihalide is substituted with at least one of an E1 group derived from the compound B1 and an E2 group derived from the compound B2. Then, to an ether-type solvent solution or an aromatic hydrocarbon-type solvent solution of the resultant partially substituted compound, an ether-type solvent solution or an aromatic hydrocarbon-type solvent solution of an alkali metal salt of a compound B3, or an ether-type solvent solution or an aromatic hydrocarbon-type solvent solution of a compound B3 and a base capable of scavenging a hydrogen halide is usually added at a temperature of 0 to 50° C. over 3 to 24 hours. Then, the reaction is carried out at a temperature of 0° C. to a boiling point of the solvent to substitute all remaining active halogen atoms with an E3 group derived from the compound B3.

In the method of the present invention, a protecting group (Z) is eliminated from the E3 group of the cyclic phosphonitrile-substituted compound obtained in the above step A, thereby converting an OZ group of the E3 group into an —OH group to produce a cyclic phosphonitrile-substituted compound having a hydroxyl group (step B). The method of eliminating the protecting group is described in a lot of known documents such as aforementioned documents 13 and 14, and it is possible to select from various deprotecting reactions depending on the kind of the protecting group and stability of the protecting group. For example, when the protecting group is a methyl group, the cyclic phosphonitrile-substituted compound is preferably reacted with boron trifluoride, trimethylsilane iodode or pyridine hydrochloride. When the protecting group is a tert-butyl group, the cyclic phosphonitrile-substituted compound is preferably reacted with trifluoroacetic acid, hydrogen bromide or trimethylsilane iodide. Furthermore, when the protecting group is a benzyl group, the cyclic phosphonitrile-substituted compound is preferably reacted with hydrogen/Pd—C, metallic sodium/ammonia, trimethylsilane iodide, lithium aluminum hydride, boron tribromide or boron trifluoride.

The objective cyclic phosphonitrile-substituted compound having a hydroxyl group obtained by eliminating a protecting group can be isolated and purified from the reaction system by a conventional method such as filtration, extraction with solvent, column chromatography or recrystallization.

In the method of the present invention, next, the cyclic phosphonitrile-substituted compound having a hydroxyl group obtained by the above step B with a cyanogen halide, thereby converting —OH group of the E3 group formed in the step B into an —OCN group (step C) and thus the objective cyanato group-containing cyclic phosphazene compound is obtained.

The method for converting an —OH group of the E3 group into an —OCN group, namely, the method for production of a cyanate ester is described, for example, in documents 15 and 16 below.

Document 15

I. HAMERTON, CHEMISTRY AND TECHNOLOGY OF CYANATEESTER RESINS, BLACKIE ACADEMIC & PROFESSIONAL, (1994).

Document 16

S. PATAT (Ed.), THE CHEMISTRY OF FUNCTIONAL GROUPS, THE CHEMISTRY OF CYANATES AND THIO DERIVATIVES, JOHN WILEY & SONS, (1977).

As described in these documents, as the method of producing a cyanate ester, for example, (1) a method of reacting a cyanogen halide and phenols in the presence of a tertiary amine and (2) a method of reacting an alkali metal salt of an alcohol-based or phenol-based compound with a cyanogen halide are known. Examples of the usable cyanogen halide include a cyanogen chloride and a cyanogen bromide. The method of producing these cyanate esters can be selected depending on the kind and stability of the cyclic phosphonitrile-substituted compound having a hydroxyl group.

The objective cyanato group-containing cyclic phosphazene compound obtained by reacting the cyclic phosphonitrile-substituted compound having a hydroxyl group with the cyanogen halide can be isolated and purified from the reaction system by a usual method such as filtration, extraction with solvent, column chromatography or recrystallization.

In the method of the present invention, since all or a portion of active halogen atoms of the cyclic phosphonitrile dihalide is/are substituted with an E3 group in the step A and a protecting group of the E3 group is eliminated in the following step B, the resultant cyanato group-containing cyclic phosphazene compound is a novel one which does not have any crosslinked structure between cyclic phosphonitrile-substituted compounds having a hydroxyl group as intermediates as described above.

Resin Composition

The resin composition of the present invention contains a cyanato group-containing cyclic phosphazene compound of the present invention and a resin component.

In the resin composition of the present invention, the cyanato group-containing cyclic phosphazene compounds of the present invention may be used alone, or two or more kinds of them may be used in combination. As the resin component, various thermoplastic resins or thermosetting resins can be used. These resin component may be a natural or synthetic resin component.

Specific examples of the thermoplastic resin usable herein include polyethylene, polyisoprene, polybutadiene, chlorinated polyethylene, polyvinyl chloride, a styrene resin, an impact-resistant polystyrene, an acrylonitrile-styrene resin (AS resin), an acrylonitrile-butadiene-styrene resin (ABS resin), a methyl methacrylate-butadiene-styrene resin (MBS resin), a methyl methacrylate-acrylonitrile-butadiene-styrene resin (MABS resin), an acrylonitrile-acryl rubber-styrene resin (AAS resin), polymethyl acrylate, polymethyl methacrylate, polycarbonate, polyphenylene ether, modified polyphenylene ether, aliphatic-type polyamide, aromatic-type polyamide, a polyester resin such as polyethylene terephthalate, polypropylene terephthalate, polytrimethylene terephthalate, polybutylene terephthalate and polyethylene naphthalate, polyphenylene sulfide, polyether ether ketone, polysulfone, polyarylate, polyether ketone, polyether nitrile, polythioether sulfone, polyether sulfone and a liquid crystal polymer. It is possible to use, as the modified polyphenylene ether, those obtained by introducing a reactive functional group such as a carboxyl group, an epoxy group, an amino group, a hydroxyl group or an anhydrous dicarboxyl group into a portion or all of polyphenylene ether through any method such as graft reaction or copolymerization. When the resin composition of the present invention is used as materials for electronic equipments, particularly casings and components for office automation equipments, audio and visual equipments, communication equipments and household electrical appliances, a polyester resin, an ABS resin, polycarbonate, modified polyphenyleneether or polyamide is preferably used as a thermoplastic resin.

Specific examples of the thermosetting resin usable herein include polyurethane, a phenol resin, a melamine resin, a urea resin, an unsaturated polyester resin, a diallylphthalate resin, a silicone resin, a maleimide resin, a cyanate ester resin, a maleimide-cyanate ester resin, a benzooxazine resin, polybenzimidazole, polyimide, polyamideimide, polyetherimide, polyesterimide, polycarbodiimide and an epoxy resin. The polyimide-type resin such as polyimide, polyamideimide, polyetherimide, polyesterimide, polycarbodiimide, a maleimide resin or a maleimide-cyanate ester resin may be provided with thermoplasticity and solvent solubility so as to improve handling-processability and adhesion. When the resin composition of the present invention is used in applications of electronic components, particularly encapsulant of various IC elements, substrate materials of wiring boards, insulating materials such as interlayer insulation materials and insulating adhesive materials, or insulating materials, conductive materials and surface protecting materials of Si substrates or SiC substrate, polyurethane, a phenol resin, a bismaleimide resin, a cyanate ester resin, a bismaleimide-cyanate ester resin, a polyimide-type resin or an epoxy resin is preferably used as a thermosetting resin.

Various resin components described above may be used alone, however, two or more kinds of them may be used in combination according to need.

In the resin composition of the present invention, the amount of the cyanato group-containing cyclic phosphazene compound to be used can be appropriately set depending on various conditions such as the resin component type and applications of the resin composition, and is preferably set within a range from 0.1 to 200 parts by weight, more preferably from 0.5 to 100 parts by weight, and still more preferably from 1 to 50 parts by weight, with respect to 100 parts by weight of the solid content of the resin component. If the amount of the cyanato group-containing cyclic phosphazene compound used is less than 0.1 parts by weight, there is a possibility that the resin molded product made of the resin composition does not exhibit sufficient flame retardancy. In contrast, if the amount used is more than 200 parts by weight, original characteristics of the resin component become impaired and thus it may become impossible to obtain a resin molded product having the characteristics.

The resin composition of the present invention can contain various additives depending on the kind of the resin component and applications of the resin composition as long as the objective physical properties are not impaired. Examples of the usable additive include inorganic fillers such as natural silica, calcined silica, synthetic silica, amorphous silica, white carbon, alumina, aluminum hydroxide, magnesium hydroxide, calcium silicate, calcium carbonate, zinc borate, zinc sttanate, titanium oxide, zinc oxide, molybdenum oxide, zinc molybdate, natural mica, synthetic mica, aerosil, kaolin, clay, talc, calcined kaolin, calcined clay, calcined talc, wollastonite, short glass fiber, fine glass powder, hollow glass and potassium titanate fiber; surface treating agents of fillers, such as silane coupling agent; release agent such as waxes, fatty acid and metal salts thereof, acid amides and paraffin; flame retardants, for example, phosphorous-type flame retardants such as phosphate, condensed phosphate, phosphoric amide, phosphoramidate, ammonium phosphate and red phosphorus, chlorine-type flame retardants such as chlorinated paraffin, nitrogen-type flame retardants such as melamine, melamine cyanurate, melam, melem, melon and succinoguanamine, silicone-type flame retardants and bromine-type flame retardants; flame-retardant aids such as antimony trioxide; dripping inhibitors such as polytetrafluoroethylene (PTFE); ultraviolet absorbers such as benzotriazole; antioxidants such as hindered phenol and styrenated phenol; photopolymerization initiators such as thioxanthone-type photopolymerization initiators; fluorescent whitening agents such as stilbene derivatives; curing agents; dyes; pigments; colorants; photostabilizers; photosensitizers; thickeners; lubricants; defoamers; leveling agents; brightening agents; polymerization inhibitors; thixotropic agents; plasticizers and antistatic agents.

Furthermore, the resin composition of the present invention can contain thermosetting resin curing agents and curing accelerators, if necessary. There is no limitation on the curing agents and curing accelerators used here as long as they are usually used, and examples thereof include an amine compound, a phenol compound, an acid anhydride, imidazoles and an organic metal salt. Two or more kinds of them can be used in combination.

When the resin composition of the present invention is used as materials for electronic and electric fields, for example, sealing agents and substrates of electronic components such as LSI, the resin component is preferably a cyanate ester resin, an epoxy resin, a polyimide resin, a bismaleimide resin, a bismaleimide-cyanate ester resin or a modified polyphenylene ether resin.

There is no limitation on the cyanate ester resin which can be used in the resin composition of the present invention as long as it has two or more cyanato groups in one molecule. Examples of the cyanate ester resin include a cyanate ester compound, and a prepolymer of 500 to 5,000 weight average molecular weight, which has a triazine ring formed by trimerization of a cyanato group of a cyanate ester compound.

Examples of the cyanate ester compound usable herein include 1,3-dicyanatobenzene, 1,4-dicyanatobenzene, 1,3,5-tricyanatobenzene, 1,3-dicyanatonaphthalene, 1,4-dicyanatonaphthalene, 1,6-dicyanatonaphthalene, 1,8-dicyanatonaphthalene, 2,6-dicyanatonaphthalene, 2,7-dicyanatonaphthalene, 1,3,6-tricyanatonaphthalene, 4,4'-dicyanatobiphenyl, 3,3',5,5'-tetramethyl-4,4'-dicyanatobiphenyl, bis(4-cyanatophenyl)methane, bis(4-cyanato-3-methylphenyl)methane, bis(4-cyanato-3-tert-butylphenyl)methane, bis(4-cyanato-3-iso-propylphenyl)methane, bis(4-cyanato-3,5-dimethylphenyl)methane, bis(2-cyanato-3-tert-1-butyl-5-methylphenyl)methane, bis(4-cyanatophenyl)ethane, bis(4-cyanato-3-methylphenyl)ethane, bis(4-cyanato-3-tert-butylphenyl)ethane, bis(4-cyanato-3-iso-propylphenyl)ethane, bis(4-cyanato-3,5-dimethylphenyl)ethane, bis(2-cyanato-3-tert-butyl-5-methylphenyl)ethane, 2,2-bis(4-cyanatophenyl)propane, 2,2-bis(4-cyanato-3-methylphenyl)propane, 2,2-bis(4-cyanato-3-tert-butylphenyl)propane, 2,2-bis(4-cyanato-3-iso-propylphenyl)propane, 2,2-bis(4-cyanato-3,5-dimethylphenyl)propane, 2,2-bis(2-cyanato-3-tert-butyl-5-methylphenyl)propane, 2,2-bis(4-cyanato-3-tert-butyl-6-methylphenyl)propane, 2,2-bis(3-allyl-4-cyanatophenyl)propane, 2,2-bis(4-cyanatophenyl)hexafluoropropane, 1,1-bis(4-cyanatophenyl)butane, 1,1-bis(4-cyanato-3-methylphenyl)butane, 1,1-bis(4-cyanato-3-tert-butylphenyl)butane, 1,1-bis(4-cyanato-3-iso-propylphenyl)butane, 1,1-bis(4-cyanato-3,5-dimethylphenyl)butane, 1,1-bis(2-cyanato-3-tert-butyl-5-methylphenyl)butane, 1,1-bis(4-cyanato-3-tert-butyl-6-methylphenyl)butane, 1,1-bis(3-allyl-4-cyanatophenyl)butane, bis(4-cyanatophenyl)ether, bis(4-cyanato-3-methylphenyl)ether, bis(4-cyanato-3-tert-butylphenyl)ether, bis(4-cyanato-3-iso-propylphenyl)ether, bis(4-cyanato-3,5-dimethylphenyl)ether, bis(2-cyanato-3-tert-butyl-5-methylphenyl)ether, bis(4-cyanatophenyl)sulfide, bis(4-cyanato-3-methylphenyl)sulfide, bis(4-cyanato-3-tert-butylphenyl)sulfide, bis(4-cyanato-3-iso-propylphenyl)sulfide, bis(4-cyanato-3,5-dimethylphenyl)sulfide, bis(2-cyanato-3-tert-butyl-5-methylphenyl)sulfide, bis(4-cyanatophenyl)sulfone, bis(4-cyanato-3-methylphenyl)sulfone, bis(4-cyanato-3-tert-butylphenyl)sulfone, bis(4-cyanato-3-iso-propylphenyl)sulfone, bis(4-cyanato-3,5-dimethylphenyl)sulfone, bis(2-cyanato-3-tert-butyl-5-methylphenyl)sulfone, bis(4-cyanatophenyl)carbonyl, bis(4-cyanato-3-methylphenyl)carbonyl, bis(4-cyanato-3-tert-butylphenyl)carbonyl, bis(4-cyanato-3-iso-propylphenyl)carbonyl, bis(4-cyanato-3,5-dimethylphenyl)carbonyl, bis(2-cyanato-3-tert-butyl-5-methylphenyl)carbonyl, 1,1-bis(4-cyanatophenyl)cyclohexane, 1,1-bis(4-cyanato-3-methylphenyl)cyclohexane, tris(4-cyanatophenyl)phosphite and tris(4-cyanatophenyl)phosphate.

The method of producing the above prepolymer include a method in which a cyanate ester compound is polymerized using, as catalysts, acids such as mineral acid and Lewis acid, salts such as sodium alcoholates and tertiary amines, and salts such as sodium carbonate. In this process, to the polymerization reaction system, an oligomer of a novolak resin or a hydroxyl group-containing thermoplastic resin (for example, hydroxypolyphenylene ether, hydroxypolystyrene, etc.), and a cyanogen halide may be added.

As the cyanate ester resin, cyanate ester resins obtained by the reaction of 2,2-bis(4-cyanatophenyl)propane, 1,1-bis(4-cyanatophenyl)butane, a novolak resin and a cyanogen halide are preferred. Two or more kinds of cyanate ester resins may be used in combination.

When a cyanate ester resin is used as the resin component, a curing catalyst and other resins are preferably added to the resin composition of the present invention so as to improve thermosetting property. Since the resin composition of the present invention using the cyanate ester resin (hereinafter also referred to as a "cyanate ester resin composition") can exhibit excellent dielectric properties in the case of high degree of curing, it is necessary to sufficiently cure the cyanate ester resin. The curing reaction of the cyanate ester resin may require 2 or more hours at high temperature of 200° C. or higher, and thus a curing catalyst is preferably used so as to promote the curing reaction of the cyanate ester resin.

There is no limitation on the curing catalyst usable herein as long as it is a compound capable of promoting the curing reaction of the cyanate ester resin. Examples thereof include chelate compounds of an acetylacetonate and metal, such as copper(II) acetylacetonate, cobalt(II) acetylacetonate, cobalt(III) acetylacetonate, zinc(II) acetylacetonate and manganese(II) acetylacetonate; carboxylic acid metal salt catalysts such as copper octylate, cobalt octylate, zinc octylate, copper naphthenate, cobalt naphthenate and zinc naphthenate; alkylphenols such as N-(4-hydroxyphenyl)maleimide, p-tert-butylphenol, p-tert-amylphenol, p-tert-octylphenol, 4-cumylphenol and nonylphenol; a phenol resin; and a compound containing active hydrogen, such as low-volatile alcohols. These curing catalysts can be used alone, or appropriately used in combination. The curing catalyst is preferably a chelate compound of acetylacetonate and metal, particularly a chelate compound of copper(II) acetylacetonate or zinc(II) acetylacetonate and metal in view of the fact that the curing reaction is significantly promoted.

The amount of the curing catalyst to be used can be set depending on the kind of the curing catalyst and the degree of promoting the curing reaction. For example, when the curing catalyst is a chelate compound of acetylacetonate and metal, the amount of the curing catalyst used is preferably within a range from 0.001 to 0.1 parts by weight, based on 100 parts by weight of the cyanate ester resin composition. When the curing catalyst is the other compound, the amount of the curing catalyst to be used is preferably within a range from 0.1 to 20 parts by weight based on 100 parts by weight of the cyanate ester resin composition. If the amount of the curing catalyst used is less than the above range, the effect of promoting the curing reaction may become insufficient. In contrast, if the used amount is more than the above range, the resultant cyanate ester resin composition may be insufficient in storage stability.

When a proper amount of a monovalence phenol compound is reacted with the cyanato group-containing cyclic phosphazene compound of the present invention, cyanato groups of the cyanate ester resin composition can be imide-carbonated and thus cyanato groups remaining after curing can be decreased. By decreasing high polar cyanato groups after curing, a dielectric constant and a dissipation factor of the entire cured product can be decreased to the value of a cured product made only of the cyanate ester resin. It is preferable that the monovalence phenol compound used for this purpose has high reactivity with the cyanato group and is monofunctional, as well as has comparatively low molecular weight and also has good compatibility with the cyanate ester compound. Examples of the monovalence phenol compound include p-tert-butylphenol, p-tert-amylphenol, p-tert-octylphenol, 4-cumylphenol and nonylphenol which are used as the curing catalyst.

There is no limitation on the usable epoxy resin in the resin composition of the present invention as long as it is a compound having two or more epoxy groups in one molecule. Specific examples thereof include novolac-type epoxy resins obtained by the reaction of phenols with aldehydes, such as a phenol novolac-type epoxy resin, a brominated phenol novolac-type epoxy resin, an ortho-cresol novolac-type epoxy resin, a biphenyl novolac-type epoxy resin, a bisphenol-A novolac-type epoxy resin and a naphthol novolac-type epoxy resin; phenol type epoxy resins obtained by reacting phenols with epichlorohydrin, such as a bisphenol-A type epoxy resin, a brominated bisphenol-A type epoxy resin, a bisphenol-F type epoxy resin, a bisphenol-AD type epoxy resin, a bisphenol-S type epoxy resin, a biphenol type epoxy resin, a naphthalene type epoxy resin, a cyclopentadiene type epoxy resin, an alkyl-substituted biphenol type epoxy resin, a polyfunctional phenol type epoxy resin and tris(hydroxyphenyl)methane; aliphatic epoxy resins obtained by reacting alcohols with epichlorohydrin, such as trimethylolpropane, oligopropylene glycol and hydrogenated bisphenol-A; glycidyl ester-type epoxy resins obtained by reacting hexahydrophthalic acid, tetrahydrophthalic acid or phthalic acid with epichlorohydrin or 2-methyl epichlorohydrin; glycidylamine-type epoxy resins obtained by reacting an amine such as diaminodiphenylmethane or aminophenol with epichlorohydrin; heterocyclic epoxy resins obtained by reacting a polyamine such as isocyanuric acid with epichlorohydrin; and phosphazene compounds having a glycidyl group, epoxy-modified phosphazene resins, isocyanate-modified epoxy resins, cyclic aliphatic epoxy resins and urethane-modified epoxy resins. Among these epoxy resins, a phenol novolac-type epoxy resin, an ortho-cresol novolac-type epoxy resin, a bisphenol-A type epoxy resin, a biphenyl type epoxy resin, a biphenyl novolac-type epoxy resin, a naphthalene type epoxy resin, a polyfunctional phenol type epoxy resin, and a phenol type epoxy resin obtained by reacting tris(hydroxyphenyl)methane with epichlorohydrin. These epoxy resins may be used alone, or two or more kinds of them may be used in combination.

When the above epoxy resin is used as the resin component (hereinafter such a resin composition sometimes referred to as an "epoxy resin composition"), the cyanato group-containing cyclic phosphazene compound of the present invention is reacted with an epoxy group to form an oxazolidone ring and thus it can function as a curing agent of the epoxy resin. The epoxy resin composition may contain other curing agent together with the cyanato group-containing cyclic phosphazene compound of the present invention. When the cyanato group-containing cyclic phosphazene compound of the present invention and the other curing agent are used in combination as the curing agent in the epoxy resin composition, the proportion of the cyanato group-containing cyclic phosphazene compound of the present invention is preferably from 0.1 to 99% by weight, and more preferably from 0.5 to 90% by weight, based on the total amount of the curing agent (that is, the total amount of the cyanato group-containing cyclic phosphazene compound of the present invention and the other curing agent). If the proportion of the cyanato group-containing cyclic phosphazene compound is less than 0.1% by weight, there is a possibility that a resin molded product made of the resin composition does not exhibit sufficient flame retardancy.

There is no limitation on the other curing agent to be used in combination with the cyanato group-containing cyclic phosphazene compound in the epoxy resin composition. Examples thereof include polyamine-type curing agents such as aliphatic polyamine, aromatic polyamine and polyamide-polyamine; acid anhydride-type curing agents such as hexahydrophthalic anhydride and methyltetrahydrophthalic anhydride; phenol-type curing agents such as phenol novolak and cresol novolak; phosphazene compounds having a hydroxyl group; and Lewis acids such as boron trifluoride, as well as salts thereof and dicyandiamides. These curing agents may be used alone, or two or more kinds of them may be used in combination.

In the epoxy resin composition, the amount of the curing agent (that is, the cyanato group-containing cyclic phosphazene compound of the present invention or a combination of the cyanato group-containing cyclic phosphazene compound of the present invention and the other curing agent) to be used is preferably set within a range from 0.5 to 1.5 equivalents, and more preferably from 0.6 to 1.2 equivalents, based on 1 equivalent of the epoxy group of the epoxy resin.

The epoxy resin composition may contain a curing accelerator. There is no limitation on the usable curing accelerator. Examples thereof include imidazole-type compounds such as 2-methylimidazole and 2-ethylimidazole; tertiary amine-type compounds such as 2-(dimethylaminomethyl)phenol; and triphenylphosphine compounds. When the curing accelerator is used, the amount to be used is preferably set within a range from 0.01 to 15 parts by weight, and more preferably from 0.1 to 10 parts by weight, based on 100 parts by weight of the epoxy resin.

The epoxy resin composition may contain known reactive diluents and additives according to need. Examples of the usable reactive diluent include, but are not limited to, aliphatic alkyl glycidyl ethers such as butyl glycidyl ether, 2-ethyl hexyl glycidyl ether and allyl glycidyl ether; alkyl glycidyl esters such as glycidyl methacrylate and tertiary carboxylic acid glycidyl ester; and aromatic alkyl glycidyl ethers such as styrene oxide and phenyl glycidyl ether, credyl glycidyl ether, p-s-butyl phenyl glycidyl ether and nonyl phenyl glycidyl ether. These reactive diluents may be used alone, or two or more kinds of them may be used in combination. As the additives, those previously-mentioned can be used.

The resin compositions of the present invention such as the cyanate ester resin composition and the epoxy resin composition can be obtained by uniformly mixing the components. When the resin composition is allowed to stand at a temperature within a range from about 100 to 250° C. for 1 to 36 hours depending on the kind of resin component, the curing reaction sufficiently proceeds to form a cured product. For example, when the epoxy resin composition is allowed to stand at a temperature within a range from about 150 to 250° C. for 2 to 15 hours, the curing reaction sufficiently proceeds to form a cured product. In such a curing process, since the cyanato group of the cyanato group-containing cyclic phosphazene compound of the present invention is reacted with the resin component and is stably maintained in the cured product, thermal reliability of the cured product scarcely deteriorates. The cyanato group-containing cyclic phosphazene compound of the present invention can enhance flame retardancy without impairing mechanical properties (particularly, glass transition temperature) of the cured product. Therefore, the resin composition of the present invention can be widely used as materials for production of various resin molded products, and used in applications such as coating materials, adhesives and the like.

Since orientational polarization of dipoles in molecules used exerts a large influence on dielectric properties of a polymer material, the dielectric constant can be decreased by decreasing polar groups in the molecules and also the dissipation factor can be decreased by suppressing motion of the polar groups. The cyanato group-containing cyclic phosphazene compound contained in the resin composition of the present invention has a cyanato group of high polarity, however can form a rigid triazine structure having symmetry upon curing the composition. The cyanato group-containing cyclic phosphazene can hardly enhance the dielectric constant and the dissipation factor accordingly, and thus a cured product having low dielectric constant and low dissipation factor is obtained by the resin composition of the present invention. Therefore, the resin composition of the present invention is particularly suitable for encapsulant of semiconductors, and is also particularly suitable for use as materials for producing electric and electronic components used for formation of circuit boards (particularly, a metal clad laminate board, a substrate for a printed circuit board, an adhesive for a printed circuit board, an adhesive sheet for a printed circuit board, a circuit protective insulation film for a printed circuit board, a conductive paste for a printed circuit board, a sealing agent for a multilayered printed circuit board, a circuit protective agent, a cover lay film, and a cover ink).

Polymerizable Composition

The polymerizable composition of the present invention contains a cyanato group-containing cyclic phosphazene compound of the present invention. Two or more kinds of cyanato group-containing cyclic phosphazene compounds may be used. The polymerizable composition can contain various additives depending on the purposes as long as the objective physical properties are not impaired. Usable additives are same as those mentioned in relation to the above resin composition.

The polymerizable composition may contain a curing catalyst so as to improve thermosetting property. Usable curing catalysts are same as those mentioned in relation to the above resin composition, that is, chelate compounds of acetylacetonate and metal, carboxylic acid metal salt catalysts, alkylphenols, phenol resins, and compounds containing active hydrogen, such as low-volatile alcohols.

Furthermore, the polymerizable composition may contain a monovalence phenol compound for the purpose of imidecarbonating a cyanato group thereby decreasing a cyanato group remaining after curing and decreasing the dielectric constant and the dissipation factor of a polymer (cured product) similar to the case of the above resin composition. Monovalence phenol compounds are same as those listed in relation to the above resin composition.

The polymerizable composition of the present invention is obtained by uniformly mixing necessary components. When the polymerizable composition is heated, polymerization proceeds between cyanato group-containing cyclic phosphazene compounds to form a polymer, and thus a cured product (resin molded product) is formed. The cured product is substantially made of the polymer of the cyanato group-containing cyclic phosphazene of the present invention and is therefore excellent in flame retardancy and thermal reliability. Also, the cured product has high glass transition temperature and is therefore excellent in mechanical properties. Therefore, the polymerizable composition of the present invention can be widely used as materials for production of resin molded products used in various fields.

The cyanato group-containing cyclic phosphazene compound contained in the polymerizable composition of the present invention has a cyanato group of high polarity, however, it can form a rigid triazine structure having symmetry upon curing the composition. The cyanato group-containing cyclic phosphazene can hardly enhance a dielectric constant and a dissipation factor of a cured product accordingly, and thus a cured product having a low dielectric constant and a low dissipation factor is obtained by the polymerizable composition of the present invention. Therefore, the polymerizable composition of the present invention is particularly suitable for encapsulant of semiconductors, and is also particularly suitable for use as materials for producing electric and electronic components used for formation of circuit boards (particularly, a metal clad laminate board, a substrate for a printed circuit board, an adhesive for a printed circuit board, an adhesive sheet for a printed circuit board, a circuit protective insulation film for a printed circuit board, a conductive paste for a printed circuit board, a sealing agent for a multilayered printed circuit board, a circuit protective agent, a cover lay film, and a cover ink).

EXAMPLES

The present invention will be described in detail below by way of examples, but the present invention is not limited thereto.

In the following examples, "unit" of "unit mol" means a minimum constituent unit of a cyclic phosphazene compound, for example, (PNA$_2$) for the general formula (1), and (PNX$_2$) for the general formula (7). When X is chlorine, one unit mol is 115.87 g.

In the following examples, percentages and parts are by weight unless otherwise specified.

The phosphazene compounds obtained by examples were identified based on the results of measurement of $^1$H-NMR spectrum and $^{31}$P-NMR spectrum, CHN elemental analysis, measurement of IR spectrum, analysis of a chlorine element (residual chlorine) by a potentiometric titration method using silver nitrate after decomposition with fused alkali, analysis of a phosphorus element by ICP-AES after wet decomposition with microwave and TOF-MS analysis. A hydroxyl equivalent was measured in accordance with a neutralization titration method of hydroxyl value measuring methods provided in JIS K 0070-1992 "Test methods for acid value, saponification value, ester value, iodine value, hydroxyl value and unsaponifiable matter of chemical products", and then a hydroxyl value mgKOH/g was converted into a hydroxyl equivalent g/eq.

Example 1

Production of Cyanato Group-Containing Cyclic Phosphazene Compound of Type 2

[Step 1: Production of Cyclic Phosphonitrile-Substituted Compound According to the Above Method 2-C]

In a 2 liter flask equipped with a stirrer, a thermometer, a reflux condenser, a separated-water receiver and a nitrogen introducing tube, 41.7 g (0.50 mol) of 48% NaOH aqueous solution, 1,000 ml of toluene and 100.1 g of (0.50 mol) of 4'-methoxyphenyl-4-phenol were charged. Water in the flask was removed (recovered water: about 30 ml) by azeotropic dehydration while heating with stirring under a nitrogen atmosphere to prepare a sodium salt of 4'-methoxyphenyl-4-phenol. The resultant slurry solution was cooled to 20° C., and 500 ml of tetrahydrofuran (THF) was added thereto to obtain a uniform solution.

Next, in a 3 liter flask equipped with a stirrer, a thermometer, a reflux condenser and a nitrogen introducing tube, a THF solution of hexachlorocyclotriphosphazene [hexachlorocyclotriphosphazene: 58.0 g (0.50 unit mol), THF: 500 ml] was charged and, after the sodium salt solution of 4'-methoxyphenyl-4-phenol prepared above was added dropwise under stirring at 5° C. over 6 hours, a reaction was conducted with stirring under reflux (85° C.) for 12 hours. After the completion of the reaction, the reaction solution was concentrated to about 700 ml, and the reaction product was dissolved by adding 300 ml of toluene and 500 ml of water, and then the organic layer was separated by a separatory funnel. The organic layer was washed for three times with water and water-toluene was azeotropically dehydrated to obtain a toluene solution of an anhydrous 4'-methoxyphenyl-4-phenoxy partially substituted compound.

Next, in a 3 liter flask equipped with a stirrer, a thermometer, a reflux condenser and a nitrogen introducing tube, the toluene solution of the anhydrous 4'-methoxyphenyl-4-phenoxy partially substituted compound, 39.1 g (0.65 mol) of n-propanol, 111.3 ml (0.80 mol) of triethylamine (TEA) and 0.6 g (5 mmol) of dimethylaminopyridine were charged and then a reaction was conducted with stirring at a reflux temperature (103° C.) for 10 hours. After the completion of the reaction, the reaction solution was concentrated to about 700 ml and the content in the flask was dissolved by adding 300 ml of toluene and 500 ml of water, and then the organic layer was separated by a separatory funnel. The organic layer was washed twice with 2% hydrochloric acid and was further washed three times with water, and then toluene was distilled off to obtain 122.7 g (yield: 84%) of a product as a viscous pale bistered liquid. The analytical results of the product are as follows:

$^1$H-NMR spectrum (in deuterated acetone, δ, ppm):
—CH$_3$ 0.9 (3H), —CH$_2$— 1.6 (2H), —CH$_2$— 3.6 (2H), —CH$_3$ 3.7 (3H), phenyl C—H 6.5 to 7.8(8H)

$^{31}$P-NMR spectrum (in deuterated acetone, δ, ppm):
Trimer (P=N)$_3$ 12.3

CHNP elemental analysis:
Calc. C: 62.5%, H: 6.1%, N: 4.8%, P: 10.6%.
Found. C: 62.3%, H: 6.2%, N: 4.9%, P: 10.4%.

Analysis of residual chlorine:
<0.01%

TOF-MS (m/z):
771, 911, 1051

The above analytical results revealed that the product obtained in this step was a mixture of [N$_3$=P$_3$ (OC$_6$H$_4$—C$_6$H$_4$OCH$_3$)$_2$(OCH$_2$CH$_2$CH$_3$)$_4$], [N$_3$=P$_3$(OC$_6$H$_4$—C$_6$H$_4$OCH$_3$)$_3$(OCH$_2$CH$_2$CH$_3$)$_3$] and [N$_3$=P$_3$(OC$_6$H$_4$—C$_6$H$_4$OCH$_3$)$_4$(OCH$_2$CH$_2$CH$_3$)$_2$] and had an average composition of [N=P(OC$_6$H$_4$—C$_6$H$_4$OCH$_3$)$_{0.92}$(OCH$_2$CH$_2$CH$_3$)$_{1.08}$]$_3$.

[Step 2: Deprotection]

In a 1 liter flask equipped with a stirrer, a thermometer, a reflux condenser and a nitrogen introducing tube, 87.6 g (0.30 unit mol) of the product obtained in step 1 and 650 ml of toluene were charged. Under a nitrogen atmosphere, 75.5 ml (0.28 mol) of 47% boron trifluoride ethyl ether was added dropwise at a temperature of 5 to 10° C. over one hour, followed by aging with stirring at the same temperature for 2 hours. After the completion of the reaction, the reaction solution was added to 400 ml of water and the organic layer was separated by a separatory funnel. The organic layer was washed three times with water and then toluene was distilled off to obtain 76.2 g (yield: 91%) of a product as a viscous pale bistered liquid. The analytical results of the product were as follows:

$^1$H-NMR spectrum (in deuterated acetone, δ, ppm):
—CH$_3$ 0.9(3H), —CH$_2$— 1.6(2H), —CH$_2$— 3.3(2H), phenyl C—H 6.5 to 7.9(8H)

$^{31}$P-NMR spectrum (in deuterated acetone, δ, ppm):
Trimer (P=N)$_3$ 9.8

CHNP elemental analysis:
Calc. C: 61.6%, H: 5.4%, N: 5.0%, P: 11.1%.
Found. C: 61.4%, H: 5.7%, N: 4.9%, P: 10.9%.

Hydroxyl equivalent:
276 g/eq. (Calc. 279 g/eq.)

The above analytical results revealed that the product obtained in this step was [N=P(OC$_6$H$_4$—C$_6$H$_4$OH)$_{0.92}$(OCH$_2$CH$_2$CH$_3$)$_{1.08}$]$_3$.

[Step 3: Conversion into Cyanato Compound]

In a 1 liter flask equipped with a stirrer, a thermometer and a nitrogen introducing tube, 41.9 g (0.15 unit mol) of the product obtained in step 2, 14.0 g (0.35 mol) of NaOH and 500 g of water were charged, and they were dissolved uniformly with stirring to prepare a phenolate solution, and then the solution was cooled to 5° C. Next, in a 1 liter flask equipped with a stirrer, a thermometer, a reflux condenser and a dropping funnel, 100 g of water was charged and then cooled to a temperature of 0 to 5° C. In the flask, 6.1 g (0.10 mol) of cyanogen chloride was charged and the above phenolate solution and 19.1 g (0.31 mol) of cyanogen chloride were simultaneously added dropwise over one hour while maintaining at a temperature of 0 to 10° C., followed by stirring at the same temperature for one hour. After the completion of the reaction, 200 g of methyl isobutyl ketone (MIBK) was introduced and the organic layer was separated by a separatory funnel. The organic layer was washed twice with water and MIBK was distilled off to obtain 35.8 g (yield: 79%) of a viscous pale bistered liquid. The analytical results of the product were as follows:

$^1$H-NMR spectrum (in deuterated acetone, δ, ppm):
—CH$_3$ 0.9(3H), —CH$_2$— 1.6(2H), —CH$_2$— 3.4(2H), phenyl C—H 6.5 to 7.8 (8H)

$^{31}$P-NMR spectrum (in deuterated acetone, δ, ppm):
Trimer (P=N)$_3$ 9.4

IR spectrum (KBr, cm$^{-1}$):
—OCN 2270, 2235

CHNP elemental analysis:
Calc. C: 60.4%, H: 5.0%, N: 8.9%, P: 10.2%.
Found. C: 60.2%, H: 5.1%, N: 8.7%, P: 10.0%.

The above analytical results revealed that the product obtained in this step was [N=P(OC$_6$H$_4$—C$_6$H$_4$OCN)$_{0.92}$(OCH$_2$CH$_2$CH$_3$)$_{1.08}$]$_3$.

Example 2

Production of Cyanato Group-Containing Cyclic Phosphazene Compound of Type 2

[Step 1: Production of Cyclic Phosphonitrile-Substituted Compound by the Above Method 2-C]

In a 500 milliliter flask equipped with a stirrer, a thermometer, a reflux condenser, a separated-water receiver and a nitrogen introducing tube, 58.4 g (0.50 mol) of 48% KOH aqueous solution, 200 ml of chlorobenzene and 146.2 g (0.50 mol) of 4'-isopropyloxyphenylsulfonyl-4-phenol were charged. Water in the flask was removed (recovered water: about 39 ml) by azeotropic dehydration while heating with stirring under a nitrogen atmosphere to prepare a potassium salt of 4'-isopropyloxyphenylsulfonyl-4-phenol. The resultant slurry solution was cooled to 20° C., and 200 ml of THF was added thereto to obtain a uniform solution.

Separately, in a 1 liter flask equipped with a stirrer, a thermometer, a reflux condenser, a separated-water receiver and a nitrogen introducing tube, 87.7 g (0.75 mol) of 48% KOH aqueous solution, 500 ml of chlorobenzene and 70.6 g (0.75 mol) of phenol were charged. Water in the flask was removed (recovered water: about 59 ml) by azeotropic dehydration while heating with stirring under a nitrogen atmosphere to prepare a potassium salt of phenol. The resultant slurry solution was cooled to 20° C., and 300 ml of THF was added thereto to obtain a uniform solution.

Next, in a 2 liter flask equipped with a stirrer, a thermometer, a reflux condenser and a nitrogen introducing tube, a THF solution of hexachlorocyclotriphosphazene [hexachlorocyclotriphosphazene: 58.0 g (0.50 unit mol), THF: 250 ml] was charged and the potassium salt solution of 4'-isopropyloxyphenylsulfonyl-4-phenol prepared above was added dropwise under stirring at 5° C. over 6 hours, and then a reaction was conducted with stirring at the same temperature for 4 hours. Subsequently, the potassium salt solution of phenol prepared above was added dropwise to the reaction solution under stirring at 45° C. or lower over 0.5 hours, and then a reaction was conducted with stirring under reflux (85° C.) for 5 hours. After the completion of the reaction, the reaction solution was concentrated to about 700 ml and the content in the flask was dissolved by adding 300 ml of chlorobenzene and 500 ml of water, and then the organic layer was separated by a separatory funnel. The organic layer was washed twice with 5% NaOH aqueous solution, neutralized with 2% sulfuric acid and further washed three times with water, and then chlorobenzene was distilled off to obtain 184.3 g (yield: 90%) of the product as a pale yellow solid. The product had a melting point (peak temperature of melting) of 68° C. The analytical results of the product were as follows:

$^1$H-NMR spectrum (in deuterated acetone, δ, ppm):
—CH$_3$ 1.4(6H), —CH< 4.8(1H), phenyl C—H 6.7 to 7.3 (9H), 7.8 to 8.0(4H)
$^{31}$P-NMR spectrum (in deuterated acetone, δ, ppm):
Trimer (P=N)$_3$ 9.6
CHNP elemental analysis:
Calc. C: 58.9%, H: 4.7%, N: 3.4%, P: 7.6%.
Found. C: 58.8%, H: 4.9%, N: 3.4%, P: 7.3%.
Analysis of residual chlorine:
<0.01%
TOF-MS (m/z):
1091, 1289, 1488

The above analytical results revealed that the product obtained in this step was a mixture of [N$_3$=P$_3$(OC$_6$H$_4$—SO$_2$—C$_6$H$_4$OCH(CH$_3$)$_2$)$_2$(OC$_6$H$_5$)$_4$], [N$_3$=P$_3$(OC$_6$H$_4$—SO$_2$—C$_6$H$_4$OCH(CH$_3$)$_2$)$_3$(OC$_6$H$_5$)$_3$], [N$_3$=P$_3$(OC$_6$H$_4$—SO$_2$—C$_6$H$_4$OCH(CH$_3$)$_2$)$_4$(OC$_6$H$_5$)$_2$] and had an average composition of [N=P(OC$_6$H$_4$—SO$_2$—C$_6$H$_4$OCH(CH$_3$)$_2$)$_{0.90}$(OC$_6$H$_5$)$_{1.10}$]$_3$.

[Step 2: Deprotection]

In a 1 liter flask equipped with a stirrer, a thermometer, a reflux condenser and a nitrogen introducing tube, 122.9 g (0.30 unit mol) of the product obtained in step 1 and 450 ml of acetic acid were charged. In the flask, 218.5 g (0.81 mol) of 30% hydrobromic acid/acetic acid solution was added dropwise under a nitrogen atmosphere at a temperature of 5 to 10° C. over one hour, followed by aging with stirring at 50° C. for 16 hours. After the completion of the reaction, the reaction solution was concentrated, and excess hydrobromic acid and acetic acid were distilled off. After dissolving the residue by adding 300 ml of MIBK and 200 ml of water, the organic layer was separated by a separatory funnel. The organic layer was washed three times with water and MIBK was distilled off to obtain 102.6 g (yield: 92%) of a product as a pale brown solid. The product was a glassy solid and therefore it did not show a definite melting point. The analytical results of the product were as follows:

$^1$H-NMR spectrum (in deuterated acetone, δ, ppm):
phenyl C—H 6.8 to 7.3(9H), 7.7 to 7.9(4H)
$^{31}$P-NMR spectrum (in deuterated acetone, δ, ppm):
Trimer (P=N)$_3$ 9.6
CHNP elemental analysis:
Calc. C: 56.2%, H: 3.7%, N: 3.8%, P: 8.3%.
Found. C: 56.0%, H: 3.9%, N: 3.8%, P: 8.1%.
Hydroxyl equivalent:
375 g/eq. (Calc. 372 g/eq.)

The above analytical results revealed that the product obtained in this step was [N=P(OC$_6$H$_4$—SO$_2$—C$_6$H$_4$OH)$_{0.90}$(OC$_6$H$_5$)$_{1.10}$]$_3$.

[Step 3: Conversion into Cyanato Compound]

In a 1 liter flask equipped with a stirrer, a thermometer and a nitrogen introducing tube, 55.8 g (0.15 unit mol) of the product obtained in step 2 and 500 ml of acetone were charged. In the flask, 8.7 g (0.14 mol) of cyanogen chloride was added dropwise at a temperature of 0 to 5° C. with stirring and then 13.7 g (0.14 mol) of TEA was added dropwise at 10° C. or lower with vigorous stirring. A reaction was conducted with stirring at a temperature of 5 to 10° C. for 30 minutes. After the completion of the reaction, the precipitated TEA hydrochloride was removed by filtration and acetone was distilled off under reduced pressure. After the content in the flask was dissolved by adding 300 ml of chloroform and 300 ml of water, the organic layer was separated by a separatory funnel. The organic layer was washed twice with water and dehydrated over anhydrous magnesium sulfate, and then chloroform was distilled off to obtain 54.4 g (yield: 92%) of a pale yellow solid. The product was a glassy solid and therefore it did not show a definite melting point. The analytical results of the product were as follows:

$^1$H-NMR spectrum (in deuterated chloroform, δ, ppm):
phenyl C—H 6.8 to 7.5(9H), 7.7 to 8.2(4H)
$^{31}$P-NMR spectrum (in deuterated chloroform, δ, ppm):
Trimer (P=N)$_3$ 9.2
IR spectrum (KBr, cm$^{-1}$):
—OCN 2285, 2258
CHNP elemental analysis:
Calc. C: 55.8%, H: 3.2%, N: 6.8%, P: 7.9%.
Found. C: 55.7%, H: 3.5%, N: 6.7%, P: 7.8%.

The above analytical results revealed that the product obtained in this step was [N=P(OC$_6$H$_4$—SO$_2$—C$_6$H$_4$OCN)$_{0.90}$(OC$_6$H$_5$)$_{1.10}$]$_3$.

Example 3

Production of Cyanato Group-Containing Cyclic Phosphazene Compound of Type 1

[Step 1: Production of Cyclic Phosphonitrile-Substituted Compound by the Above Method 1-A]

In a 5 liter flask equipped with a stirrer, a thermometer, a reflux condenser, a separated-water receiver and a nitrogen introducing tube, 50.0 g (0.60 mol) of an aqueous 48% NaOH solution, 70.1 g (0.60 mol) of 48% KOH aqueous solution, 3,000 ml of toluene and 348.4 g (1.20 mol) of 4'-allyloxyphenylsulfonyl-4-phenol were charged. Water in the flask was removed (recovered water: about 84 ml) by azeotropic dehydration while heating with stirring under a nitrogen atmosphere to prepare a sodium/potassium salt of 4'-allyloxyphenylsulfonyl-4-phenol. In the flask, a toluene solution of hexachlorocyclotriphosphazene (hexachlorocyclotriphosphazene: 58.0 g (0.50 unit mol), toluene: 300 ml) was added dropwise under stirring at a temperature of 20 to 25° C. over one hour, and then a reaction was conducted under reflux (108° C.) for 8 hours. After the completion of the reaction, the content in the flask was dissolved by adding 1,000 ml of water to the reaction solution and the organic layer was separated by a separatory funnel. The organic layer was washed twice with 5% NaOH aqueous solution, neutralized with 2% nitric acid and further washed three times with water, and then toluene was distilled off to obtain 286.1 g (yield: 92%) of a product as a white solid. The product showed a melting point (peak temperature of melting) of 164° C. The analytical results of the product were as follows:

$^1$H-NMR spectrum (in deuterated acetone, δ, ppm):
—CH$_2$— 4.6(4H), =CH$_2$ 5.3 to 5.4(4H), —CH= 6.0 (2H), phenyl C—H 6.8 to 7.1(8H), 7.8 to 8.0(8H)
$^{31}$P-NMR spectrum (in deuterated acetone, δ, ppm):
Trimer (P=N)$_3$ 8.5
CHNP elemental analysis:
Calc. C: 57.8%, H: 4.2%, N: 2.2%, P: 5.0%.
Found. C: 57.9%, H: 4.4%, N: 2.1%, P: 4.9%.
Analysis of residual chlorine:
<0.01%

The above analytical results revealed that the product obtained in this step was [N=P(OC$_6$H$_4$—SO$_2$—C$_6$H$_4$OCH$_2$CH=CH$_2$)$_2$]$_3$.

[Step 2: Deprotection]

In a 2 liter flask equipped with a stirrer, a thermometer, a reflux condenser and a nitrogen introducing tube, 187.1 g (0.30 unit mol) of the product obtained in step 1 and 1,000 ml of acetic acid were charged and 323.6 g (1.20 mol) of 30% hydrobromic acid/acetic acid solution was added dropwise under a nitrogen atmosphere at a temperature of 5 to 10° C. over 2 hours, followed by aging with stirring at 50° C. for 8 hours. After the completion of the reaction, the reaction solution was concentrated, and excess hydrobromic acid and acetic acid were distilled off. The residue was dissolved by adding 500 ml of MIBK and 500 ml of water and then the organic layer was separated by a separatory funnel. The organic layer was washed three times with water and MIBK was distilled off to obtain 141.9 g (yield: 87%) of a product as a white solid. The product was a glassy solid and therefore it did not show a definite melting point. The analytical results of the product were as follows:

$^1$H-NMR spectrum (in deuterated acetone, δ, ppm):
phenyl C—H 7.0 to 7.2(8H), 7.8 to 8.0(8H), —OH 9.5(2H)
$^{31}$P-NMR spectrum (in deuterated acetone, δ, ppm):
Trimer (P=N)$_3$ 8.5
CHNP elemental analysis:
Calc. C: 53.0%, H: 3.3%, N: 2.6%, P: 5.7%.
Found. C: 52.8%, H: 3.6%, N: 2.5%, P: 5.6%.
Hydroxyl equivalent:
270 g/eq. (Calc. 272 g/eq.)

The above analytical results revealed that the product obtained in this step was [N=P(OC$_6$H$_4$—SO$_2$—C$_6$H$_4$OH)$_2$]$_3$.

[Step 3: Conversion into Cyanato Compound]

In a 1 liter flask equipped with a stirrer, a thermometer and a nitrogen introducing tube, 81.5 g (0.15 unit mol) of the product obtained in step 2, 42.5 g (0.42 mol) of TEA and 500 ml of MIBK were charged. In the flask, 25.8 g (0.42 mol) of cyanogen chloride was added dropwise at 3° C. or lower over one hour and a reaction was conducted with stirring at the same temperature for 30 minutes. After the completion of the reaction, the content in the flask was dissolved by adding 300 ml of water and the organic layer was separated by a separatory funnel. The organic layer was washed twice with water and dehydrated over anhydrous magnesium sulfate, and then MIBK was distilled off to obtain 79.2 g (yield: 89%) of a pale yellow solid. The product was a glassy solid and therefore it did not show a definite melting point. The analytical results of the product were as follows:

$^1$H-NMR spectrum (in deuterated chloroform, δ, ppm):
phenyl C—H 6.8 to 7.4(8H), 7.7 to 8.2(8H)
$^{31}$P-NMR spectrum (in deuterated chloroform, δ, ppm):
Trimer (P=N)$_3$ 9.0
IR spectrum (KBr, cm$^{-1}$):
—OCN 2285, 2258
CHNP elemental analysis:
Calc. C: 52.6%, H: 2.7%, N: 7.1%, P: 5.2%.
Found. C: 52.4%, H: 2.8%, N: 7.0%, P: 5.2%.

The above analytical results revealed that the product obtained in this step was [N=P(OC$_6$H$_4$—SO$_2$—C$_6$H$_4$OCN)$_2$]$_3$.

Example 4

Production of Cyanato Group-Containing Cyclic Phosphazene Compound of Type 2

[Step 1: Production of cyclic phosphonitrile-substituted Compound by the Above Method 2-D]

In a 1 liter flask equipped with a stirrer, a thermometer, a reflux condenser, a separated-water receiver and a nitrogen introducing tube, 58.4 g (0.50 mol) of 48% KOH aqueous solution, 450 ml of chlorobenzene and 47.1 g (0.50 mol) of phenol were charged. Water in the flask was removed (recovered water: about 39 ml) by azeotropic dehydration while heating with stirring under a nitrogen atmosphere to prepare a potassium salt of phenol. The resultant slurry solution was cooled to 20° C. and 200 ml of THF was charged to obtain a uniform solution.

Separately, in a 2 liter flask equipped with a stirrer, a thermometer, a reflux condenser, a separated-water receiver and a nitrogen introducing tube, 76.0 g (0.65 mol) of 48% KOH aqueous solution, 800 ml of chlorobenzene and 188.8 g (0.65 mol) of 4'-allyloxyphenylsulfonyl-4-phenol were charged. Water in the flask was removed (recovered water: about 51 ml) by azeotropic dehydration while heating with stirring under a nitrogen atmosphere to prepare a potassium salt of 4'-allyloxyphenylsulfonyl-4-phenol. The slurry solution was cooled to 20° C. and 300 ml of THF was charged to obtain a uniform solution.

Next, in a 3 liter flask equipped with a stirrer, a thermometer, a reflux condenser and a nitrogen introducing tube, a THF solution of hexachlorocyclotriphosphazene [hexachlorocyclotriphosphazene: 58.0 g (0.50 unit mol), THF: 200 ml] was charged and the potassium salt solution of the phenol prepared above was added dropwise under stirring at 5° C. over 10 hours, and then a reaction was conducted with stirring at 25° C. for 5 hours. Subsequently, to the reaction solution, the potassium salt solution of 4'-allyloxyphenylsulfonyl-4-phenol prepared above was added under stirring at 25° C. over one hour, and then a reaction was conducted with stirring under reflux (86° C.) for 10 hours. After the completion of the reaction, the reaction solution was concentrated to about 1,000 ml and the content in the flask was dissolved by adding 600 ml of chlorobenzene and 600 ml of water, and then the organic layer was separated by a separatory funnel. The organic layer was washed twice with 5% NaOH aqueous solution, neutralized with 2% sulfuric acid and further washed three times with water, and then chlorobenzene was distilled off to obtain 207.1 g (yield: 96%) of a product as a pale yellow solid. The product was a glassy solid and therefore it did not show a definite melting point. The analytical results of the product were as follows:

$^1$H-NMR spectrum (in deuterated chloroform, δ, ppm):
—CH$_2$— 4.6(2H), =CH$_2$ 5.3 to 5.4(2H), —CH= 6.0 (1H), phenyl C—H 6.8 to 7.2(9H), 7.8 to 8.0(4H)

$^{31}$P-NMR spectrum (in deuterated chloroform, δ, ppm):
Trimer (P=N)$_3$ 8.5

CHNP elemental analysis:
Calc. C: 58.9%, H: 4.2%, N: 3.2%, P: 7.2%.
Found. C: 58.7%, H: 4.4%, N: 3.1%, P: 7.0%.
Analysis of residual chlorine:
<0.01%
TOF-MS (m/z):
1087, 1283, 1480

The above analytical results revealed that the product obtained in this step was a mixture of [N$_3$=P$_3$(OC$_6$H$_4$—SO$_2$—C$_6$H$_4$OCH$_2$CH=CH$_2$)$_2$(OC$_6$H$_5$)$_4$], [N$_3$=P$_3$(OC$_6$H$_4$—SO$_2$—C$_6$H$_4$OCH$_2$CH=CH$_2$)$_3$(OC$_6$H$_5$)$_3$] and [N$_3$=P$_3$(OC$_6$H$_4$—SO$_2$—C$_6$H$_4$OCH$_2$CH=CH$_2$)$_4$(OC$_6$H$_5$)$_2$] and had an average composition of [N=P(OC$_6$H$_4$—SO$_2$—C$_6$H$_4$OCH$_2$CH=CH$_2$)$_{1.02}$(OC$_6$H$_5$)$_{0.98}$]$_3$.

[Step 2: Deprotection]

In a 1 liter flask equipped with a stirrer, a thermometer, a reflux condenser and a nitrogen introducing tube, 129.4 g (0.30 unit mol) of the product obtained in step 1 and 500 ml of acetic acid were charged and 161.8 g (0.60 mol) of 30% hydrobromic acid/acetic acid solution was added dropwise under a nitrogen atmosphere at a temperature of 5 to 10° C. over 2 hours, followed by aging with stirring at 50° C. for 8 hours. After the completion of the reaction, the reaction solution was concentrated, and excess hydrobromic acid and acetic acid were distilled off. After the residue was dissolved by adding 400 ml of MIBK and 400 ml of water, the organic layer was separated by a separatory funnel. The organic layer was washed three times with water and then MIBK was distilled off to obtain 99.6 g (yield: 85%) of a product as a yellowish bistered solid. The product was a glassy solid and therefore it did not show a definite melting point. The analytical results of the resultant product were as follows:

$^1$H-NMR spectrum (in deuterated acetone, δ, ppm)
phenyl C—H 6.8 to 7.2(9H), 7.2 to 7.8(4H), —OH 9.5(1H)

$^{31}$P-NMR spectrum (in deuterated chloroform, δ, ppm):
Trimer (P=N)$_3$ 9.5

CHNP elemental analysis:
Calc. C: 55.7%, H: 3.6%, N: 3.6%, P: 7.9%.
Found. C: 55.5%, H: 3.7%, N: 3.5%, P: 7.7%.
Hydroxyl equivalent:
394 g/eq. (Calc. 391 g/eq.)

The above analytical results revealed that the product obtained in the step was [N=P(OC$_6$H$_4$—SO$_2$—C$_6$H$_4$OH)$_{1.02}$(OC$_6$H$_5$)$_{0.98}$]$_3$.

[Step 3: Conversion into Cyanato Compound]

The operation was conducted in the same manner as in step 3 of Example 3 except for using 58.6 g (0.15 unit mol) of the product obtained in step 2, 13.2 g (0.21 mol) of cyanogen chloride and 21.7 g (0.21 mol) of TEA to obtain a yellowish bistered solid of 56.8 g (yield: 91%). The product was a glassy solid and therefore it did not show a definite melting point. The analytical results of the product were as follows:

$^1$H-NMR spectrum (in deuterated chloroform, δ, ppm)
phenyl C—H 6.9 to 7.5(9H), 7.7 to 8.2(4H)

$^{31}$P-NMR spectrum (in deuterated chloroform, δ, ppm):
Trimer (P=N)$_3$ 9.2

IR spectrum (KBr, cm$^{-1}$):
—OCN 2285, 2258

CHNP elemental analysis:
Calc. C: 55.3%, H: 3.2%, N: 6.8%, P: 7.4%.
Found. C: 55.4%, H: 3.2%, N: 6.7%, P: 7.2%.

The above analytical results revealed that the product obtained in this step was [N=P(OC$_6$H$_4$—SO$_2$—C$_6$H$_4$OCN)$_{1.02}$(OC$_6$H$_5$)$_{0.98}$]$_3$.

Example 5

Production of Cyanato Group-Containing Cyclic Phosphazene Compound of Type 1

[Step 1: Production of Cyclic Phosphonitrile-Substituted Compound by the Above Method 1-A]

In a 3 liter flask equipped with a stirrer, a thermometer, a reflux condenser, a separated-water receiver and a nitrogen introducing tube, 152.0 g (1.30 mol) of 48% KOH aqueous solution, 2,000 ml of toluene and 442.5 g (1.30 mol) of 4'-benzyloxyphenylsulfonyl-4-phenol were charged. Water in the flask was removed (recovered water: about 102 ml) by azeotropic dehydration while heating with stirring under a nitrogen atmosphere to prepare a potassium salt of 4'-benzyloxyphenylsulfonyl-4-phenol. The resultant slurry solution was cooled to 20° C. and 400 ml of THF was charged to obtain a uniform solution.

Next, in a 5 liter flask equipped with a stirrer, a thermometer, a reflux condenser and a nitrogen introducing tube, a THF solution of chlorophosphazene [hexachlorocyclotriphosphazene: 52.2 g (0.45 unit mol), and octachlorocyclotetraphosphazene: 5.8 g (0.05 unit mol), THF: 300 ml] were charged and the potassium salt solution of 4'-benzyloxyphenylsulfonyl-4-phenol prepared above was added dropwise under stirring at 25° C. over one hour, and then a reaction was conducted by stirring under reflux (86° C.) for 8 hours. After the completion of the reaction, the reaction solution was concentrated to about 1,500 ml and the content in the flask was dissolved by adding 500 ml of toluene and 1,000 ml of water, and then the organic layer was separated by a separatory funnel. The organic layer was washed twice with 5% NaOH aqueous solution, neutralized with 2% sulfuric acid and further washed three times with water, and then toluene was distilled off to obtain 314.8 g (yield: 87%) of a product as a white solid. The product had a melting point (peak temperature of melting) of 149° C. The analytical results of the product were as follows:

$^1$H-NMR spectrum (in deuterated acetone, δ, ppm):
—CH$_2$— 5.0(4H), phenyl C—H 6.8 to 7.9(26H)

$^{31}$P-NMR spectrum (in deuterated acetone, δ, ppm):
Trimer (P=N)$_3$ 9.5, tetramer(P=N)$_4$ −12.4

CHNP elemental analysis:
Calc. C: 63.1%, H: 4.2%, N: 1.9%, P: 4.3%.
Found. C: 62.8%, H: 4.4%, N: 2.1%, P: 4.2%.
Analysis of residual chlorine:
<0.01%

The above analytical results revealed that the product obtained in this step was [N=P(OC$_6$H$_4$—SO$_2$—C$_6$H$_4$OCH$_2$C$_6$H$_5$)$_2$]$_3$ and [N=P(OC$_6$H$_4$—SO$_2$—C$_6$H$_4$OCH$_2$C$_6$H$_5$)$_2$]$_4$.

[Step 2: Deprotection]

In a 2 liter flask equipped with a stirrer, a thermometer, a reflux condenser and a nitrogen introducing tube, 217.1 g (0.30 unit mol) of the product obtained in step 1 and 800 ml of acetic acid were charged and 323.6 g (1.20 mol) of 30% hydrobromic acid/acetic acid solution was added dropwise under a nitrogen atmosphere at a temperature of 5 to 10° C. over 2 hours, followed by aging with stirring at 50° C. for 8 hours. After the completion of the reaction, the reaction solution was concentrated, and excess hydrobromic acid and acetic acid were distilled off. After the residue was dissolved by adding 700 ml of MIBK and 600 ml of water, the organic layer was separated by a separatory funnel. The organic layer was washed three times with water and then MIBK was distilled off to obtain 145.1 g (yield: 89%) of a product as a white solid. The product was a glassy solid and therefore it did not show a definite melting point. The analytical results of the product were as follows:

$^1$H-NMR spectrum (in deuterated acetone, δ, ppm)

phenyl C—H 6.8 to 7.9(16H), —OH 9.5(2H)

$^{31}$P-NMR spectrum (in deuterated acetone, δ, ppm): Trimer (P=N)$_3$ 9.5, tetramer (P=N)$_{4-12.4}$ CHNP elemental analysis:

Calc. C: 53.0%, H: 3.3%, N: 2.6%, P: 5.7%.

Found. C: 52.8%, H: 3.6%, N: 2.5%, P: 5.6%.

Hydroxyl equivalent:

274 g/eq. (Calc. 272 g/eq.)

The above analytical results revealed that the product obtained in this step was [N=P(OC$_6$H$_4$—SO$_2$—C$_6$H$_4$OH)$_2$]$_3$ and [N=P(OC$_6$H$_4$—SO$_2$—C$_6$H$_4$OH)$_2$]$_4$.

[Step 3: Conversion into Cyanato Compound]

In a 1 liter flask equipped with a stirrer, a thermometer and a nitrogen introducing tube, 81.5 g (0.15 unit mol) of the product obtained in step 2, 18.6 g (0.18 mol) of cyanogen bromide and 500 ml of acetone were charged. While stirring vigorously, 17.5 g (0.17 mol) of TEA was added dropwise at 10° C. or lower, followed by stirring at a temperature of 5 to 10° C. for 2 hours. After the completion of the reaction, the precipitated triethylamine hydrochloride was removed by filtration and acetone was distilled off under reduced pressure. After the content in the flask was dissolved by adding 300 ml of chloroform and 300 ml of water, the organic layer was separated by a separatory funnel. The organic layer was washed twice with water and dehydrated over anhydrous magnesium sulfate, and then chloroform was distilled off to obtain 83.7 g (yield: 94%) of a pale yellow solid. The product was a glassy solid and therefore it did not show a definite melting point. The analytical results of the product were as follows:

$^1$H-NMR spectrum (in deuterated chloroform, δ, ppm):

phenyl C—H 6.6 to 7.5(8H), 7.7 to 8.6(8H)

$^{31}$P-NMR spectrum (in deuterated chloroform, δ, ppm):

Trimer (P=N)$_3$ 9.0, -11.4

IR spectrum (KBr, cm$^{-1}$):

—OCN 2285, 2258

CHNP elemental analysis:

Calc. C: 52.6%, H: 2.7%, N: 7.1%, P: 5.2%.

Found. C: 52.3%, H: 2.8%, N: 6.9%, P: 5.2%.

The above analytical results revealed that the product obtained in this step was [N=P(OC$_6$H$_4$—SO$_2$—C$_6$H$_4$OCN)$_2$]$_3$ and [N=P(OC$_6$H$_4$—SO$_2$—C$_6$H$_4$OCN)$_2$]$_4$.

Example 6

Production of Cyanato Group-Containing Cyclic Phosphazene Compound of Type 2

[Step 1: Production of Cyclic Phosphonitrile-Substituted Compound by the Above Method 2-C]

In a 3 liter flask equipped with a stirrer, a thermometer, a reflux condenser, a separated-water receiver and a nitrogen introducing tube, 41.7 g (0.50 mol) of 48% KOH aqueous solution, 1,200 ml of toluene and 170.2 g (0.50 mol) of 4'-benzyloxyphenylsulfonyl-4-phenol were charged. Water in the flask was removed (recovered water: about 30 ml) by azeotropic dehydration while heating with stirring under a nitrogen atmosphere to prepare a sodium salt of 4'-benzyloxyphenylsulfonyl-4-phenol. The resultant slurry solution was cooled to 20° C. and 600 ml of THF was charged to obtain a uniform solution.

Separately, in a 1 liter flask equipped with a stirrer, a thermometer, a reflux condenser, a separated-water receiver and a nitrogen introducing tube, 87.7 g (0.75 mol) of 48% KOH aqueous solution, 550 ml of toluene and 70.6 g (0.75 mol) of phenol were charged. Water in the flask was removed (recovered water: about 58 ml) by azeotropic dehydration while heating with stirring under a nitrogen atmosphere to prepare a potassium salt of phenol. The resultant slurry solution was cooled to 20° C. and 200 ml of THF was charged to obtain a uniform solution.

Next, in a 5 liter flask equipped with a stirrer, a thermometer, a reflux condenser and a nitrogen introducing tube, a THF solution of hexachlorocyclotriphosphazene [hexachlorocyclotriphosphazene: 58.0 g (0.50 unit mol), THF: 300 ml] was charged and the sodium salt solution of 4'-benzyloxyphenylsulfonyl-4-phenol prepared above was added dropwise under stirring at 5° C. over 6 hours, and then a reaction was conducted with stirring at 25° C. for 4 hours. Subsequently, to the reaction solution, the potassium salt solution of phenol prepared above was added dropwise under stirring at 25° C. over one hour, and then a reaction was conducted with stirring under reflux (103° C.) for 2 hours. After the completion of the reaction, the reaction solution was concentrated to about 1,000 ml and the content in the flask was dissolved by adding 200 ml of toluene and 400 ml of water, and then the organic layer was separated by a separatory funnel. The organic layer was washed twice with 5% NaOH aqueous solution, neutralized with 2% sulfuric acid and further washed three times with water, and then toluene was distilled off to obtain 201.1 g (yield: 87%) of a product as a pale yellow solid. The product was a glassy solid and therefore it did not show a definite melting point. The analytical results of the product were as follows:

$^1$H-NMR spectrum (in deuterated chloroform, δ, ppm):

—CH$_2$— 5.1(2H), phenyl C—H 6.7 to 7.0(4H), 7.0 to 7.2(5H), 7.3 to 7.4(5H), 7.6 to 7.9(4H)

$^{31}$P-NMR spectrum (in deuterated chloroform, δ, ppm):

Trimer (P=N)$_3$ 9.3

CHNP elemental analysis:

Calc. C: 62.9%, H: 4.2%, N: 3.0%, P: 6.7%.

Found. C: 62.9%, H: 4.2%, N: 3.1%, P: 6.9%.

Analysis of residual chlorine:

<0.01%

TOF-MS (m/z):
1187, 1434, 1680

The above analytical results revealed that the product obtained in this step was a mixture of [N$_3$=P$_3$(OC$_6$H$_4$—SO$_2$—C$_6$H$_4$OCH$_2$C$_6$H$_5$)$_2$(OC$_6$H$_5$)], [N$_3$=P$_3$(OC$_6$H$_4$—SO$_2$—C$_6$H$_4$OCH$_2$C$_6$H$_5$)$_3$(OC$_6$H$_5$)$_3$] and [N$_3$=P$_3$(OC$_6$H$_4$—SO$_2$—C$_6$H$_4$OCH$_2$C$_6$H$_5$)$_4$(OC$_6$H$_5$)$_2$] and had an average composition of [N=P(OC$_6$H$_4$—SO$_2$—C$_6$H$_4$OCH$_2$C$_6$H$_5$)$_{0.95}$(OC$_6$H$_5$)$_{1.05}$]$_3$.

[Step 2: Deprotection]

In a 2 liter flask equipped with a stirrer, a thermometer, a reflux condenser and a nitrogen introducing tube, 139.5 g (0.30 unit mol) of the product obtained in step 1 and 800 ml of toluene were charged and 26.9 ml (0.29 mol) of boron tribromide was added dropwise under a nitrogen atmosphere at a temperature of 5 to 10° C. over 4 hours, followed by aging with stirring at a temperature of 25 to 30° C. for 12 hours. After the completion of the reaction, the reaction solution was added to 800 ml of water and the organic layer was separated by a separatory funnel. The organic layer was washed three times with water and then toluene was distilled off to obtain 105.9 g (yield: 93%) of a product as a brown solid. The product was a glassy solid and therefore it did not show a definite melting point. The analytical results of the product were as follows:

$^1$H-NMR spectrum (in deuterated acetone, δ, ppm)
phenyl C—H 6.8 to 7.3(9H), 7.7 to 7.9(4H), —OH 9.5(1H)
$^{31}$P-NMR spectrum (in deuterated acetone, δ, ppm):
Trimer (P=N)$_3$ 9.6
CHNP elemental analysis:
Calc. C: 56.0%, H: 3.4%, N: 3.7%, P: 8.2%.
Found. C: 55.7%, H: 3.7%, N: 3.8%, P: 8.4%.
Hydroxyl equivalent:
378 g/eq. (Calc. 380 g/eq.)

The above analytical results revealed that the product obtained in this step was [N=P(OC$_6$H$_4$—SO$_2$—C$_6$H$_4$OH)$_{0.95}$(OC$_6$H$_5$)$_{1.05}$]$_3$.

[Step 3: Conversion into Cyanato Compound]

In a 1 liter flask equipped with a stirrer, a thermometer and a nitrogen introducing tube, 18.1 g (0.17 mol) of cyanogen bromide and 300 ml of acetone were charged, followed by cooling to −30° C. Separately, in a 1 liter flask, 56.9 g (0.15 unit mol) of the product obtained in step 2, 17.3 g (0.17 mol) of TEA and 300 ml of acetone were charged and mixed, and the resultant solution was added dropwise in the cyanogen bromide solution prepared previously at a temperature of −20 to −30° C., followed by stirring at the same temperature for one hour. After the completion of the reaction, the precipitated triethylamine hydrochloride was removed by filtration and acetone was distilled off under reduced pressure. After the content in the flask was dissolved by adding 300 ml of chloroform and 300 ml of water, the organic layer was separated by a separatory funnel. The organic layer was washed twice with water and dehydrated over anhydrous magnesium sulfate, and then chloroform was distilled off to obtain 56.3 g (yield: 93%) of a pale brown solid. The product was a glassy solid and therefore it did not show a definite melting point. The analytical results of the product were as follows:

$^1$H-NMR spectrum (in deuterated chloroform, δ, ppm):
phenyl C—H 6.9 to 7.4(9H), 7.7 to 8.2(4H)
$^{31}$P-NMR spectrum (in deuterated chloroform, δ, ppm):
Trimer (P=N)$_3$ 9.2
IR spectrum (KBr, cm$^{-1}$):
—OCN 2285, 2258
CHNP elemental analysis:
Calc. C: 55.5%, H: 3.2%, N: 6.8%, P: 7.7%.
Found. C: 55.3%, H: 3.2%, N: 6.7%, P: 7.6%.

The above analytical results revealed that the product obtained in this step was [N=P(OC$_6$H$_4$—SO$_2$—C$_6$H$_4$OCN)$_{0.95}$(OC$_6$H$_5$)$_{1.05}$]$_3$.

Example 7

Production of Cyanato Group-Containing Cyclic Phosphazene Compound of Type 2

[Step 1: Production of Cyclic Phosphonitrile-Substituted Compound by the Above Method 2-D]

In a 1 liter flask equipped with a stirrer, a thermometer, a reflux condenser, a separated-water receiver and a nitrogen introducing tube, 41.7 g (0.50 mol) of 48% KOH aqueous solution, 250 ml of toluene and 47.1 g (0.50 mol) of phenol were charged. Water in the flask was removed (recovered water: about 29 ml) by azeotropic dehydration while heating with stirring under a nitrogen atmosphere to prepare a sodium salt of phenol. The resultant slurry solution was cooled to 20° C. and 200 ml of THF was charged to obtain a uniform solution.

Separately, in a 3 liter flask equipped with a stirrer, a thermometer, a reflux condenser, a separated-water receiver and a nitrogen introducing tube, 87.7 g (0.75 mol) of 48% KOH aqueous solution, 1,500 ml of toluene and 238.8 g (0.75 mol) of 4'-benzyloxyphenylisopropylidene-4-phenol were charged. Water in the flask was removed (recovered water: about 59 ml) by azeotropic dehydration while heating with stirring under a nitrogen atmosphere to prepare a potassium salt of 4'-benzyloxyphenylisopropylidene-4-phenol. The resultant slurry solution was cooled to 20° C. and 500 ml of THF was charged to obtain a uniform solution.

Next, in a 5 liter flask equipped with a stirrer, a thermometer, a reflux condenser and a nitrogen introducing tube, a THF solution of hexachlorocyclotriphosphazene [hexachlorocyclotriphosphazene: 58.0 g (0.50 unit mol), THF: 500 ml] was charged and the sodium salt solution of phenol prepared above was added dropwise under stirring at 5° C. over 6 hours, and then a reaction was conducted with stirring at 25° C. for 2 hours. Subsequently, to the reaction solution, the potassium salt solution of 4'-benzyloxyphenylisopropylidene-4-phenol prepared above was added dropwise under stirring at 25° C. over one hour, and then a reaction was conducted with stirring under reflux (85° C.) for 14 hours. After the completion of the reaction, the reaction solution was concentrated to about 1,000 ml and the content in the flask was dissolved by adding 500 ml of toluene and 1,000 ml of water, and then the organic layer was separated by a separatory funnel. The organic layer was washed twice with 5% NaOH aqueous solution, neutralized with 2% sulfuric acid and further washed three times with water, and then toluene was distilled off to obtain 221.9 g (yield: 96%) of a product as a brown solid. The product was a glassy solid and therefore it did not show a definite melting point. The analytical results of the product were as follows:

$^1$H-NMR spectrum (in deuterated chloroform, δ, ppm):
—CH$_3$ 1.6(6H), —CH$_2$— 5.0(2H), phenyl C—H 6.8 to 6.9(5H), 7.0 to 7.1(8H), 7.2 to 7.4(5H)
$^{31}$P-NMR spectrum (in deuterated chloroform, δ, ppm):
Trimer (P=N)$_3$ 9.9
CHNP elemental analysis:
Calc. C: 74.0%, H: 5.8%, N: 3.0%, P: 6.7%.
Found. C: 74.2%, H: 5.8%, N: 2.9%, P: 6.6%.
Analysis of residual chlorine:
<0.01%

TOF-MS (m/z):

1143, 1368, 1592

The above analytical results revealed that the product obtained in this step was a mixture of [$N_3$=$P_3$($OC_6H_4$—C($CH_3$)$_2$—$C_6H_4OCH_2C_6H_5$)$_2$($OC_6H_5$)$_4$], [$N_3$=$P_3$($OC_6H_4$—C($CH_3$)$_2$—$C_6H_4OCH_2C_6H_5$)$_3$($OC_6H_5$)$_3$] and [$N_3$=$P_3$($OC_6H_4$—C($CH_3$)$_2$—$C_6H_4OCH_2C_6H_5$)$_4$($OC_6H_5$)$_2$] and had an average composition of [N=P($OC_6H_4$—C($CH_3$)$_2$—$C_6H_4OCH_2C_6H_5$)$_{1.03}$($OC_6H_5$)$_{0.97}$]$_3$.

[Step 2: Deprotection]

In a 3 liter flask equipped with a stirrer, a thermometer, a reflux condenser and a nitrogen introducing tube, 138.7 g (0.30 unit mol) of the product obtained in step 1, 3.8 g of Pd/C ("E 101 NE/W": 10% Pd, manufactured by Degussa) and 2,500 ml of methanol were charged and then a reaction was conducted with stirring under a hydrogen atmosphere at a temperature of 50° C. for 5 hours. After the completion of the reaction, the reaction solution was filtered to remove Pd/C and the filtrate was concentrated to distill methanol off. The residue was dissolved by adding 1,000 ml of MIBK and 700 ml of water and the organic layer was separated by a separatory funnel. The organic layer was washed three times with water and MIBK was distilled off to obtain 96.4 g (yield: 87%) of a product as a brown solid. The product was a glassy solid and therefore it did not show a definite melting point. The analytical results of the product were as follows:

$^1$H-NMR spectrum (in deuterated acetone, δ, ppm)

—$CH_3$ 1.7(6H), phenyl C—H 6.8 to 6.9(4H), 6.9 to 7.2 (5H), 7.2 to 7.3(4H)

$^{31}$P-NMR spectrum (in deuterated acetone, δ, ppm):

Trimer (P=N)$_3$ 10.0

CHNP elemental analysis:

Calc. C: 69.2%, H: 5.5%, N: 3.8%, P: 8.4%.

Found. C: 69.3%, H: 5.3%, N: 3.8%, P: 8.3%.

Hydroxyl equivalent:

371 g/eq. (Calc. 369 g/eq.)

The above analytical results revealed that the product obtained in this step was [N=P($OC_6H_4$—C($CH_3$)$_2$—$C_6H_4OH$)$_{1.03}$($OC_6H_5$)$_{0.97}$]$_3$.

[Step 3: Conversion into Cyanato Compound]

The operation was conducted in the same manner as in step 3 of Example 6, except for using 55.4 g (0.15 unit mol) of the product obtained in step 2, 19.6 g (0.19 mol) of cyanogen chloride and 18.8 g (0.19 mol) of TEA, and thus 52.8 g (yield: 89%) of a yellowish brown solid was obtained. The product was a glassy solid and therefore it did not show a definite melting point. The analytical results of the product were as follows:

$^1$H-NMR spectrum (in deuterated chloroform, δ, ppm)

—$CH_3$ 1.6(6H), phenyl C—H 6.8 to 7.3(13H)

$^{31}$P-NMR spectrum (in deuterated chloroform, δ, ppm):

Trimer (P=N)$_3$ 9.8

IR spectrum (KBr, cm$^{-1}$):

—OCN 2269, 2237

CHNP elemental analysis:

Calc. C: 67.8%, H: 4.9%, N: 7.2%, P: 7.8%.

Found. C: 67.6%, H: 5.0%, N: 7.1%, P: 7.8%.

The above analytical results revealed that the product obtained in this step was [N=P($OC_6H_4$—C($CH_3$)$_2$—$C_6H_4OCN$)$_{1.03}$($OC_6H_5$)$_{0.97}$]$_3$.

Example 8

Production of Cyanato Group-Containing Cyclic Phosphazene Compound of Type 2

[Step 1: Production of Cyclic Phosphonitrile-Substituted Compound by the Above Method 2-A]

In a 3 liter flask equipped with a stirrer, a thermometer, a reflux condenser and a nitrogen introducing tube, 500 ml of 1,2-dimethoxyethane (DME) and 44.0 g (1.10 mol) of 60% NaH in oil were charged under a nitrogen atmosphere. In the flask, a DME solution of a mixture of p-cresol and 1,3,3-trimethyl-1-(4-benzyloxyphenyl)indan-6-ol (45%) and 1,3,3-trimethyl-1-(4-hydroxyphenyl)-6-benzyloxyindane (55%) [p-cresol: 54.1 g (0.50 mol), 1,3,3-trimethyl-1-(4-benzyloxyphenyl)indan-6-ol: 96.7 g (0.27 mol), 1,3,3-trimethyl-1-(4-hydroxyphenyl)-6-benzyloxyindan: 118.8 g (0.33 mol), DME: 1,000 ml] was added dropwise at 5° C. or lower over 2 hours, followed by stirring at 50° C. for 2 hours to prepare a sodium salt of p-cresol and a sodium salt of indane derivative.

Next, in a 3 liter flask equipped with a stirrer, a thermometer, a reflux condenser and a nitrogen introducing tube, a DME solution of cyclophosphazene [hexachlorocyclotriphosphazene: 46.4 g (0.40 unit mol), octachlorocyclotetraphosphazene: 5.8 g (0.05 unit mol), decachlorocyclopentaphosphazene: 2.9 g (0.025 unit mol), dodecachlorocyclohexaphosphazene: 1.7 g (0.015 unit mol), a oligocylicompound such as one which is larger than tetradecachlorocycloheptaphosphazene: 1.2 g (0.01 unit mol), DME: 500 ml) was charged and a solution of the sodium salt of p-cresol prepared above and the sodium salt of indane derivative prepared above was added dropwise under stirring at 25° C. over one hour, and then a reaction was conducted with stirring under reflux (75° C.) for 8 hours. After the completion of the reaction, the reaction solution was concentrated to about 1,000 ml and the content in the flask was dissolved by adding 500 ml of toluene and 500 ml of water, and then the organic layer was separated by a separatory funnel. The organic layer was washed twice with 5% NaOH aqueous solution, neutralized with 2% sulfuric acid, and further washed three times with water, and then DME and toluene were distilled off to obtain 228.4 g (yield: 89%) of a product as a yellow solid. The product was a glassy solid and therefore it did not show a definite melting point. The analytical results of the product were as follows:

$^1$H-NMR spectrum (in deuterated acetone, δ, ppm):

—$CH_3$ 1.0 to 1.6(12H), —$CH_2$— 2.1 to 2.4(2H), —$CH_2$— 5.0(2H), phenyl C—H 6.8 to 7.9(16H)

$^{31}$P-NMR spectrum (in deuterated acetone, δ, ppm):

Trimer (P=N)$_3$ 9.5, tetramer (P=N)$_4$ −12.4, pentamer and hexamer (P=N)$_{5,6}$ −17.0, heptamer or higher multimer (P=N)$_{\geq 7}$ −18.0 to −23.0

CHNP elemental analysis:

Calc. C: 75.5%, H: 6.4%, N: 2.7%, P: 6.0%.

Found. C: 75.2%, H: 6.6%, N: 2.7%, P: 5.8%.

Analysis of residual chlorine:

<0.01%

The above analytical results revealed that the product obtained in this step was a mixture of [N=P($OC_6H_4$-Indane-$OCH_2C_6H_5$)$_{1.05}$($OC_6H_4$—$CH_3$)$_{0.95}$]$_n$ and [N=P(O-Indane-$C_6H_4OCH_2C_6H_5$)$_{0.98}$($OC_6H_4$—$CH_3$)$_{1.02}$]$_n$

[Step 2: Deprotection]

In a 3 liter flask equipped with a stirrer, a thermometer, a reflux condenser and a nitrogen introducing tube, 154.0 g (0.30 unit mol) of the product obtained in step 1 and 1,000 ml of toluene were charged. Under a nitrogen atmosphere, 120.1 g (0.60 mol) of trimethylsilyl iodide was added dropwise to the content of the flask at a temperature of 5 to 10° C. over 10 hours and a reaction was conducted with stirring at a temperature of 25 to 30° C. for 12 hours. After the completion of the reaction, the reaction solution was introduced into 1,000 ml of water and the organic layer was separated by a separatory funnel. The organic layer was washed three times with water and then toluene was distilled off to obtain 113.9 g (yield: 90%) of a product as a yellow solid. The product was a glassy solid and therefore it did not show a definite melting point. The analytical results of the product were as follows:

$^1$H-NMR spectrum (in deuterated acetone, δ, ppm):
—$CH_3$ 1.0 to 1.6(12H), —$CH_2$— 2.1 to 2.4(2H), phenyl C—H 6.8 to 7.9(11H)

$^{31}$P-NMR spectrum (in deuterated acetone, δ, ppm):
Trimer (P=N)$_3$ 9.5, tetramer (P=N)$_4$ –12.4, pentamer and hexamer (P=N)$_{5,6}$ –17.0, heptamer or higher oligomer (P=N)$_7$ —18.0 to –23.0

CHNP elemental analysis:
Calc. C: 71.6%, H: 6.3%, N: 3.3%, P: 7.3%.
Found. C: 70.2%, H: 6.2%, N: 3.3%, P: 7.1%.

Hydroxyl equivalent:
418 g/eq. (Calc. 422 g/eq.)

The above analytical results revealed that the product obtained in this step was a mixture of [N=P($OC_6H_4$-Indane-OH)$_{1.05}$($OC_6H_4$—$CH_3$)$_{0.95}$]$_n$ and [N=P(O-Indane-$C_6H_4$OH)$_{0.98}$($OC_6H_4$—$CH_3$)$_{1.02}$]$_n$

[Step 3: Conversion into Cyanato Compound]

The operation was conducted in the same manner as in step 3 of Example 6, except for using 63.3-g (0.15 unit mol) of the product obtained in step 2, 19.4 g (0.18 mol) of cyanogen bromide and 18.5 g (0.18 mol) of TEA to obtain 58.4 g (yield: 87%) of a pale brown solid. The product was a glassy solid and therefore it did not show a definite melting point. The analytical results of the product were as follows:

$^1$H-NMR spectrum (in deuterated chloroform, δ, ppm):
—$CH_3$ 1.0 to 1.6(12H), —$CH_2$— 2.1 to 2.4(2H), phenyl C—H 6.8 to 8.0(11H)

$^{31}$P-NMR spectrum (in deuterated chloroform, δ, ppm):
Trimer (P=N)$_3$ –9.3, tetramer (P=N)$_4$ –12.5, pentamer and hexamer (P=N)$_{5,6}$ –17.0, heptamer or higher multimer (P=N)$_{\geq 7}$ –18.0 to –23.0

IR spectrum (KBr, cm$^{-1}$):
—OCN 2268, 2236

CHNP elemental analysis:
Calc. C: 70.3%, H: 5.7%, N: 6.3%, P: 6.9%.
Found. C: 70.0%, H: 5.8%, N: 6.2%, P: 6.8%.

The above analytical results revealed that the product obtained in this step was a mixture of [N=P($OC_6H_4$-Indane-OCN)$_{1.05}$($OC_6H_4$—$CH_3$)$_{0.95}$]$_n$ and [N=P(O-Indane-$C_6H_4$OCN)$_{0.98}$($OC_6H_4$—$CH_3$)$_{1.02}$]$_n$.

Example 9

Production of Cyanato Group-Containing Cyclic Phosphazene Compound of Type 1

[Step 1: Production of Cyclic Phosphonitrile-Substituted Compound by the Above Method 1-A]

In a 2 liter flask equipped with a stirrer, a thermometer, a reflux condenser and a nitrogen introducing tube, 161.4 g (1.30 mol) of 4-methoxyphenol and 700 ml of tetrahydrofuran (THF) were charged and then dissolved with stirring under a nitrogen atmosphere. After the solution was cooled to 10° C. or lower, 28.8 g (1.25 mol) of metallic sodium was added at the same temperature or lower, followed by stirring with heating at 60° C. for 2 hours to prepare a sodium salt of 4-methoxyphenol. To the solution, a THF solution of hexachlorocyclotriphosphazene [hexachlorocyclotriphosphazene 58.0 g (0.50 unit mol), THF: 300 ml] was added dropwise at a temperature of 20 to 25° C. over one hour, followed by stirring under reflux (68° C.) for 8 hours. After the completion of the reaction, the reaction solution was concentrated and THF was distilled off. Then, the content in the flask was dissolved by adding 500 ml of toluene and 500 ml of water and the organic layer was separated by a separatory funnel. The organic layer was washed twice with 2% NaOH aqueous solution, neutralized with 2% nitric acid and further washed twice with water, and then toluene was distilled off to obtain 141.3 g (yield: 97%) of a product as a white solid. The product had a melting point (peak temperature of melting) of 103° C. (the reference value indicated in the above document 11: 103 to 104° C.). The analytical results of the product were as follows:

1H-NMR spectrum (in deuterated chloroform, δ, ppm)
—$CH_3$ 3.7(6H), phenyl C—H 6.6 to 6.9(8H)

$^{31}$P-NMR spectrum (in deuterated chloroform, δ, ppm)
Trimer (P=N)$_3$ 11.1

Analysis of residual chlorine:
<0.01%

The above analytical results revealed that the product obtained in this step was [N=P($OC_6H_4OCH_3$)$_2$]$_3$.

[Step 2: Deprotection]

In a 3 liter flask equipped with a stirrer, a thermometer, a reflux condenser and a nitrogen introducing tube, 116.5 g (0.4 unit mol) of the product obtained in step 1 and 900 ml of methylene dichloride (MDC) were added, followed by stirring while a nitrogen gas is allowed to flow until a uniform mixture is obtained. While a nitrogen gas was allowed to flow, a MDC solution of boron tribromide (BBr$_3$) [BBr$_3$: 250.5 g (1.0 mol), MDC: 1,000 ml] was added dropwise at a temperature of 25 to 30° C. over 2 hours, followed by stirring at the same temperature range for 10 hours. To the reaction solution, 1,000 ml of water was added dropwise at 10° C. or lower and the reaction solution was concentrated under reduced pressure, and then MDC was distilled off. The residue was dissolved again by adding 1,000 ml of MIBK and 700 ml of water and the organic layer was separated by a separatory funnel. The organic layer was washed three times with 500 ml of water, neutralized with 5% sodium hydrogen carbonate aqueous solution and further washed twice with 500 ml of water, and then MIBK was distilled off to obtain 103.2 g (yield: 98%) of a product as a pale yellow solid. The product had a melting point (peak temperature of melting) of 242° C. (the reference value indicated in the following document 17: 241 to 243° C.). The analytical results of the product were as follows:

Document 17

Alessandro Medici et al., Macromolecules, 1992, 25(10), 2569-2574

$^1$H-NMR spectrum (in deuterated acetone, δ, ppm)
phenyl C—H 6.7(8H), —OH 8.3(2H)

$^{31}$P-NMR spectrum (in deuterated acetone, δ, ppm)
Trimer (P=N)$_3$ 11.4

Hydroxyl equivalent:
131 g/eq. (Calc. 132 g/eq.)

The above analytical results revealed that the product obtained in this step was $[N=P(OC_6H_4OH)_2]_3$.

[Step 3: Conversion into Cyanato Compound]

In a 2 liter flask equipped with a stirrer, a thermometer and a nitrogen introducing tube, 92.1 g (0.35 unit mol) of the product obtained in step 2, 86.0 g (0.85 mol) of TEA and 700 ml of MIBK were charged. In the flask, a MIBK solution of cyanogen bromide (cyanogen bromide: 90.0 g (0.85 mol), MIBK: 300 ml) was added dropwise at 3° C. or lower over one hour and then a reaction was conducted with stirring at the same temperature for one hour. After the completion of the reaction, the content in the flask was dissolved by adding 500 ml of water and the organic layer was separated by a separatory funnel. The organic layer was washed twice with water and dehydrated over anhydrous magnesium sulfate, and then MIBK was distilled off to obtain 105.2 g (yield: 96%) of a pale yellow solid. The product had a melting point (peak temperature of melting) of 143° C. The analytical results of the product were as follows:

$^1$H-NMR spectrum (in deuterated acetone, δ, ppm)
phenyl C—H 7.2 to 7.5(8H)
$^{31}$P-NMR spectrum (in deuterated acetone, δ, ppm)
Trimer (P=N)$_3$ 10.0
IR spectrum (KBr, cm$^{-1}$)
—OCN 2271, 2236
CHNP elemental analysis:
Calc. C: 53.7%, H: 2.6%, N: 13.4%, P: 9.9%.
Found. C: 53.4%, H: 2.9%, N: 13.2%, P: 9.8%.

The above analytical results revealed that the product obtained in this step was $[N=P(OC_6H_4OCN)_2]_3$.

Example 10

Production of Cyanato Group-Containing Cyclic Phosphazene Compound of Type 2

[Step 1: Production of Cyclic Phosphonitrile-Substituted Compound by the Above Method 2-C]

In a 500 milliliter flask equipped with a stirrer, a thermometer, a reflux condenser, a separated-water receiver and a nitrogen introducing tube, 58.4 g (0.50 mol) of 48% KOH aqueous solution, 200 ml of chlorobenzene and 62.1 g (0.50 mol) of 4-methoxyphenol were charged. Water in the flask was removed (recovered water: about 39 ml) by azeotropic dehydration while heating with stirring under a nitrogen atmosphere to prepare a potassium salt of 4-methoxyphenol. The resultant slurry solution was cooled to 20° C. and 200 ml of THF was charged to obtain a uniform solution.

Separately, in a 1 liter flask equipped with a stirrer, a thermometer, a reflux condenser, a separated-water receiver and a nitrogen introducing tube, 87.7 g (0.75 mol) of 48% KOH aqueous solution, 500 ml of chlorobenzene and 70.6 g (0.75 mol) of phenol were charged. Water in the flask was removed (recovered water: about 59 ml) by azeotropic dehydration while heating with stirring under a nitrogen atmosphere to prepare a potassium salt of phenol. The resultant slurry solution was cooled to 20° C. and 300 ml of THF was charged to obtain a uniform solution.

Next, in a 2 liter flask equipped with a stirrer, a thermometer, a reflux condenser and a nitrogen introducing tube, a THF solution of hexachlorocyclotriphosphazene [hexachlorocyclotriphosphazene: 58.0 g (0.50 unit mol), THF: 250 ml) were charged and the potassium salt solution of 4-methoxyphenol prepared above was added dropwise under stirring at 5° C. over 6 hours, and then a reaction was conducted with stirring at the same temperature for 5 hours. Subsequently, to the reaction solution, the potassium salt solution of phenol prepared above was added dropwise under stirring at 40° C. or lower over 0.5 hour, and then a reaction was conducted with stirring under reflux (85° C.) for 5 hours. After the completion of the reaction, the reaction solution was concentrated to about 700 ml and the content in the flask was dissolved by adding 500 ml of toluene and 500 ml of water, and then the organic layer was separated by a separatory funnel. The organic layer was washed twice with 5% NaOH aqueous solution, neutralized with 2% sulfuric acid and further washed three times with water, and then toluene was distilled off to obtain 122.5 g (yield: 94%) of a product as a pale yellow liquid. The analytical results of the product were as follows:

$^1$H-NMR spectrum (in deuterated chloroform, δ, ppm)
—CH$_3$ 3.8(3H), phenyl C—H 6.6 to 7.2(9H)
$^{31}$P-NMR spectrum (in deuterated chloroform, δ, ppm):
Trimer (P=N)$_3$ 10.5
CHNP elemental analysis:
Calc. C: 59.8%, H: 4.6%, N: 5.4%, P: 11.9%.
Found. C: 59.6%, H: 4.9%, N: 5.3%, P: 11.8%.
Analysis of residual chlorine:
<0.01%
TOF-MS (m/z)
753, 784, 814

The above analytical results revealed that the product obtained in the step was $[N=P(OC_6H_4OCH_3)_{0.98}(OC_6H_5)_{1.02}]_3$.

[Step 2: Deprotection]

In a 3 liter flask equipped with a stirrer, a thermometer, a reflux condenser and a nitrogen introducing tube, 104.2 g (0.4 unit mol) of the product obtained in step 1 and 800 ml of methylene dichloride (MDC) were added, followed by stirring while a nitrogen gas was allowed to flow until a uniform mixture was obtained. While a nitrogen gas was allowed to flow, a MDC solution of boron tribromide (BBr$_3$) [BBr$_3$: 125.3 g (0.5 mol), MDC: 500 ml) was added dropwise at a temperature of 25 to 30° C. over 1.5 hours, followed by stirring at the same temperature range for 10 hours. To the reaction solution, 800 ml of water was added dropwise at 10° C. or lower and the reaction solution was concentrated under reduced pressure, and then MDC was distilled off. The residue was dissolved again by adding 800 ml of MIBK and 600 ml of water and the organic layer was separated by a separatory funnel. The organic layer was washed three times with 400 ml of water, neutralized with 5% sodium hydrogen carbonate aqueous solution and further washed twice with 400 ml of water, and then MIBK was distilled off to obtain 96.8 g (yield: 98%) of a product as a pale yellow solid. The product was a glassy solid and therefore it did not show a definite melting point. The analytical results of the product were as follows:

$^1$H-NMR spectrum (in deuterated acetone, δ, ppm)
phenyl C—H 6.6 to 7.4(9H), —OH 8.4(1H)
$^{31}$P-NMR spectrum (in deuterated acetone, δ, ppm)
Trimer (P=N)$_3$ 10.7
CHNP elemental analysis:
Calc. C: 58.4%, H: 4.1%, N: 5.7%, P: 12.6%.
Found. C: 58.1%, H: 4.3%, N: 5.6%, P: 12.5%.
Hydroxyl equivalent:
248 g/eq. (Calc. 247 g/eq.)

The above analytical results revealed that the product obtained in this step was $[N=P(OC_6H_4OH)_{0.98}(OC_6H_5)_{1.02}]_3$.

[Step 3: Conversion into Cyanato Compound]

In a 1 liter flask equipped with a stirrer, a thermometer and a nitrogen introducing tube, 74.1 g (0.30 unit mol) of the product obtained in step 2 and 500 ml of acetone were charged. In the flask, 19.1 g (0.31 mol) of cyanogen chloride was added dropwise at a temperature of 0 to 5° C. with stirring and 31.4 g (0.31 mol) of TEA was added dropwise at 10° C. or lower with stirring vigorously, and then a reaction was conducted with stirring at a temperature of 5 to 10° C. for 30 minutes. After the completion of the reaction, the precipitated TEA hydrochloride was removed by filtration and acetone was distilled off under reduced pressure. After the content in the flask was dissolved by adding 500 ml of chloroform and 500 ml of water, the organic layer was separated by a separatory funnel. The organic layer was washed twice with water and dehydrated over anhydrous magnesium sulfate, and then chloroform was distilled off to obtain 74.9 g (yield: 92%) of a pale yellow solid. The product was a glassy solid and therefore it did not show a definite melting point. The analytical results of the product were as follows:

$^1$H-NMR spectrum (in deuterated chloroform, δ, ppm):

phenyl C—H 6.8 to 7.3(9H)

$^{31}$P-NMR spectrum (in deuterated chloroform, δ, ppm):

Trimer $(P=N)_3$ 10.1

IR spectrum (KBr, cm$^{-1}$):

—OCN 2270, 2235

CHNP elemental analysis:

Calc. C: 57.5%, H: 3.4%, N: 10.2%, P: 11.4%.

Found. C: 57.4%, H: 3.6%, N: 10.1%, P: 11.3%.

The above analytical results revealed that the product obtained in this step was $[N=P(OC_6H_4OCN)_{0.98}(OC_6H_5)_{1.02}]_3$.

Comparative Example 1

Production of Cyclic Phosphazene Compound

In accordance with the method described in H. R. ALLCOCK (1972). PHOSPHORUS-NITROGEN COMPOUNDS. ACADEMIC PRESS, pp. 151, a mixture of $[N=P(OC_6H_5)_2]_3$ and $[N=P(OC_6H_5)_2]_4$ (white solid/melting point: 65 to 112° C.) was obtained using a cyclophosphazene mixture of 81% of hexachlorocyclotriphosphazene and 19% of octachlorocyclotetraphosphazene.

Examples 11 to 13

Production of Resin Molded Product

A polymerizable composition comprising the cyanato group-containing cyclic phosphazene compound synthesized in Examples 2, 7 or 9 was heated at 170° C. for one hour thereby partially trimerizing to prepare a prepolymer. The prepolymer was poured into a PTFE mold and cured with heating at 200° C. for 2 hours, then at 230° C. for 3 hours to obtain two kinds of sheet-like cured products (resin molded products) each having a thickness of 1/16 inch and 5 mm. IR spectrum revealed that adsorption of a cyanato group (OCN) completely disappeared in the cured product.

With respect to the resultant sheet-like cured products, flammability, heat resistance, dielectric properties in a gigahertz band, and glass transition temperature were examined. Flammability and heat resistance were evaluated using a 1/16 inch thick sheet-like cured product. Dielectric properties and glass transition temperature were evaluated using a 5 mm thick sheet-like cured product. Evaluation methods of the respective items were as follows. The results are shown in Table 1.

(Flammability)

Based on a vertical combustion test in accordance with UL-94 Standard of Underwriter's Laboratories Inc., flammability of each sample was classified into four ratings such as V-0, V-1, V-2 and below standard by the total flame maintenance time for 10 flame contacts and the presence or absence of the samples showing drip igniting cotton during flaming. The evaluation criteria were shown below. Level of flammability decreases as follows: V-0>V-1>V-2>below standard.

V-0: Samples would Satisfy all Conditions Described Below:
(A) the total flame extinguishing time for 5 samples (two times each) following flame contact (10 flame contacts) was within 50 seconds;
(B) the flame extinguishing time for 5 samples (two times each) following flame contact was within 5 seconds;
(C) none of samples showed any drip igniting cotton located 300 mm below samples;
(D) none of samples displayed glowing combustion which persists beyond 30 seconds after second flame contact; and
(E) none of samples showed any flaming until clamping.

V-1: Samples would Satisfy all Conditions Described Below:
(A) the total flame extinguishing time for 5 samples (two times each) following flame contact (10 flame contacts) was within 250 seconds;
(B) the flame extinguishing time for 5 samples (two times each) following flame contact was within 30 seconds;
(C) none of samples showed any drip igniting cotton located 300 mm below samples;
(D) none of samples displayed glowing combustion which persists beyond 60 seconds after second flame contact; and
(E) none of samples showed any flaming until clamping.

V-2: Samples would Satisfy all Conditions Described Below:
(A) the total flame extinguishing time for 5 samples (two times each) following flame contact (10 flame contacts) was within 250 seconds;
(B) the flame extinguishing time for 5 samples (two times each) following flame contact was within 30 seconds;
(C) at least one of five samples showed drip igniting cotton located 300 mm below samples;
(D) none of samples displayed glowing combustion which persists beyond 60 seconds after second flame contact; and
(E) none of samples showed any flaming until clamping.

(Heat Resistance)

Samples were treated at 288° C. for 20 minutes and a change in appearance was visually observed. In Table 1, "Yes" meaned that there arose no change in appearance due to bleed out of a cyclic phosphazene compound. In contrast, "No" meaned that there arose a change in appearance due to bleed out of a cyclic phosphazene compound.

(Dielectric Properties)

Using a complex dielectric constant measurement apparatus with a cavity resonance perturbation method (Kudo-kyoshinki Setsudo Fukuso-Yudenritsu Hyoka Souchi: trade name of Kantoh Electronics Application and Development Inc.), a sheet-like cured product was allowed to stand under the following conditions for 24 hours, and then a dielectric constant and a dissipation factor were measured under the following conditions.

Measuring temperature: 22 to 24° C.

Measuring humidity: 45 to 55%

Measuring frequency: 5 GHz (Glass Transition Temperature)

Using DMS-200 (trade name) manufactured by Seiko Electronic Industries Co., Ltd., a storage elastic modulus (E') of a sheet-like cured product was measured at a measuring length (distance between measuring jigs) of 20 mm under the conditions described below, and then an inflection point of the storage elastic modulus (∈') was referred to as a glass transition temperature (° C.).
Measuring atmosphere: dry air atmosphere
Measuring temperature: within a range from 20 to 400° C.
Measuring sample: cured resin sheet slit by 9 mm in width and 40 mm in length

TABLE 1

| | Cyanato group-containing cyclic phosphazene compound | Flammability UL-94 | Heat resistance | Dielectric properties (Dielectric constant/Dissipation factor) | Glass transition temperature (° C.) |
|---|---|---|---|---|---|
| Example 11 | Example 2 | V-0 | Yes | 2.8/0.002 | 231 |
| Example 12 | Example 7 | V-0 | Yes | 2.7/0.001 | 228 |
| Example 13 | Example 9 | V-0 | Yes | 2.7/0.002 | 235 |

As seen from the results shown in Table 1, the sheet-like cured products of Examples 11 to 13 showed low dielectric constant and excellent dissipation factor in a frequency of a gigahertz band, and also showed high glass transition temperature.

For comparison, a sheet-like cured product was intended to make using the cyclic phosphazene compound synthesized in Comparative Example 1. Here, the cyclic phosphazene compound synthesized in Comparative Example 1 was heated at 170° C. for one hour, and poured into a PTFE mold followed by heating at 200° C. for 2 hours and at 230° C. for 3 hours. As a result, appearance of the cyclic phosphazene compound turned from a white solid into a brown solid. The heated solid was added to toluene, and was completely dissolved therein. Therefore, it was found that no curing on the solid arise. That is, no sheet-like cured product was obtained and the same evaluation as in Examples 11 to 13 could not be conducted.

Synthesis Example 1

Synthesis of Soluble Polyimide Resin

In a 3 liter glass flask equipped with a stirrer, a thermometer, a reflux condenser and a nitrogen introducing tube, 277.7 g (0.95 mol) of 1,3-bis(3-aminophenoxy)benzene, 10.7 g (0.05 mol) of 3,3'-dihydroxy-4,4'-diaminobiphenyl and 700 ml of N,N-dimethylformamide (DMF) were charged and then dissolved with stirring under a nitrogen atmosphere. The solution in the flask was stirred under a nitrogen atmosphere and a DMF solution of 4,4'-(4,4'-isopropylidenediphenoxy) bisphthalic anhydride (IPBP) [IPBP: 520.5 g (1.00 mol), DMF: 1,100 ml] was added dropwise at a temperature of 5 to 10° C. over 2 hours, followed by stirring at room temperature for 3 hours to obtain a polyamic acid solution. 2,500 g of the resultant polyamic acid solution was transferred to a tray coated with a fluorocarbon resin (PTFE) and then heated under reduced pressure (conditions: at 200° C. under 5.7 hPa or less for 6 hours) in a vacuum oven to obtain 750 g of a soluble polyimide resin.

Synthesis Example 2

Synthesis of Difunctional PPE Oligomer

In a 2 liter glass flask equipped with a stirrer, a thermometer, a reflux condenser and an air introducing tube, 11.3 g (0.012 mol) of CuCl, 70.7 g (0.55 mol) of di-n-butylamine and 500 ml of methyl ethyl ketone were charged, followed by stirring at a reaction temperature of 40° C. A solution prepared by preliminarily dissolving 45.4 g (0.16 mol) of 4,4'-(1-methylethylidene)bis(2,6-dimethylphenol) and 58.6 g (0.48 mol) of 2,6-dimethylphenol in 1,000 ml of methyl ethyl ketone was added dropwise over 2 hours while bubbling the air at 2 liter/min, followed by stirring for one hour while continuously bubbling the air at 2 liter/min. The reaction was terminated by adding a disodium dihydrogen ethylenediaminetetraacetate aqueous solution. The reaction solution was washed three times with 3% hydrochloric acid aqueous solution and further washed with ion-exchanged water. The resultant solution was concentrated and further vacuum-dried to obtain 101.3 g of a difunctional PPE oligomer having a hydroxyl group at each end. The oligomer had a number average molecular weight of 860, a weight average molecular weight of 1,150 and a hydroxyl equivalent of 455 g/eq.

Examples 14 to 20

Preparation of Resin Composition 50 g of the soluble polyimide resin obtained in Synthesis Example 1, 25.0 g of 2,2'-bis(4-cyanatophenyl)propane (manufactured by Lonza under the trade name of "BADCy") as a bisphenol A-type cyanate ester compound and a cyanato group-containing cyclic phosphazene compound shown in Table 2 were dissolved in dioxolane to obtain a resin solution (resin composition).

The resin solution was cast on the surface of a 125 µm thick PET film (manufactured by TOYO METALLIZING CO., LTD. under the trade name of "Cerapeel HP"). Then, the coated PET film was dried with heating in a hot air oven at each temperature of 60° C., 80° C., 100° C., 120° C. and 140° C. for 3 minutes to obtain a two-layered resin sheet comprising the PET film as a substrate. The PET film was removed from the two-layered resin sheet to obtain a single-layered resin sheet (thickness before heat curing: 50 µm). The resultant resin sheet was interposed between 18 µm thick rolled copper foils (manufactured by JAPAN ENERGY CORPORATION under the trade name of "BHY-22B-T") so as to contact the surface of the resin with the roughened surface of the copper foil, followed by pressing with heating under the conditions of a temperature of 230° C. and a pressure of 3 MPa for one hour to obtain a copper foil laminate (in which the single-layered resin sheet was interposed between the rolled copper foils).

With respect to the resultant copper foil laminate having a copper foil layer formed on each surface, soldering heat resistance was evaluated. The copper foil of the resultant copper foil laminate was removed by etching to obtain a cured sheet. With respect to the cured sheet, dielectric properties, flammability and glass transition temperature (Tg) were measured. Evaluation method of soldering heat resistance was as follows. Dielectric properties, flammability and glass transition temperature were measured by the same methods and conditions as those in Examples 11 to 13. The results are shown in Table 2.

(Soldering Heat Resistance)

Samples with 30 mm in length and 15 mm in width were cut from the copper foil laminate and these samples were allowed to stand under an atmosphere at a temperature of 22.5 to 23.5° C. and humidity of 39.5 to 40.5% for 24 hours. Samples were dipped in a molten solder at 288° C. for one minute and only a copper foil at one side was etched. When no abnormality such as foaming or blister was recognized on the resin portion of sample through visual observation, the sample was acceptable. The number of rejections in this regard in 20 samples was investigated.

Comparative Example 2

Preparation of Resin Composition

In the same manner as in Example 14, except that 25.0 g of the cyclic phosphazene compound produced in Comparative Example 1 was used in place of the cyanato group-containing cyclic phosphazene compound produced in Example 2, a resin composition was obtained. Using this resin composition, a copper foil laminate and a cured sheet were obtained by the same processes and conditions as those in Examples 14 to 20, and then soldering heat resistance, dielectric properties, flammability and glass transition temperature were evaluated. The results are shown in Table 2.

group-containing cyclic phosphazene compound shown in Table 3 and 50.0 g of 2,2'-bis(4-cyanatophenyl)propane (manufactured by Lonza under the trade name of "BADCy") were dissolved in dioxolane to obtain a resin solution (resin composition).

The resin solution was cast on the surface of a 125 µm thick PET film (manufactured by TOYO METALLIZING CO., LTD. under the trade name of "Cerapeel HP"). Then, the coated PET film was dried with heating in a hot air oven at each temperature of 60° C., 80° C., 100° C., 120° C. and 140° C. for 3 minutes to obtain a two-layered resin sheet comprising the PET film as a substrate. The PET film was removed from the two-layered resin sheet to obtain a single-layered resin sheet (thickness before heat curing: 50 µm). The resultant resin sheet was interposed between 18 µm thick rolled copper foils (manufactured by JAPAN ENERGY CORPORATION under the trade name of "BHY-22B-T") so as to contact that surface of the resin with the roughened surface of the copper foil, followed by pressing with heating under the conditions of a temperature of 230° C. and a pressure of 3 MPa for one hour to obtain a copper foil laminate (in which the single-layered resin sheet was interposed between the rolled copper foils). With respect to the copper foil laminate, soldering heat resistance was evaluated by the same methods as in Examples 14 to 20. With respect to the cured sheet obtained by removing the copper foil of the copper foil laminate through etching, dielectric properties, flammability and

TABLE 2

| | Cyanato group-containing cyclic phosphazene compound | | Dielectric properties (Dielectric constant/Dissipation factor) | Flammability UL-94 | Tg (° C.) | Soldering heat resistance (Number of rejections/ Number of samples) |
|---|---|---|---|---|---|---|
| | Examples | Amounts (g) | | | | |
| Example 14 | 2 | 25.0 | 2.8/0.06 | V-0 | 220 | 0/20 |
| Example 15 | 2 | 35.0 | 2.7/0.05 | V-0 | 218 | 0/20 |
| Example 16 | 3 | 25.0 | 2.8/0.07 | V-0 | 223 | 0/20 |
| Example 17 | 7 | 25.0 | 2.8/0.07 | V-0 | 217 | 0/20 |
| Example 18 | 8 | 25.0 | 2.8/0.06 | V-0 | 215 | 0/20 |
| Example 19 | 9 | 25.0 | 2.7/0.06 | V-0 | 222 | 0/20 |
| Example 20 | 10 | 25.0 | 2.8/0.07 | V-0 | 220 | 0/20 |
| Comparative Example 2 | Comparative Example 1 | 25.0 | 3.0/0.12 | V-0 | 172 | 3/20 |

As seen from the results shown in Table 2, cured articles made of the resin compositions of Examples 14 to 20 showed low dielectric constant and excellent dissipation factor in a frequency of a gigahertz band as compared with Comparative Example 2, and also showed high glass transition temperature and excellent soldering heat resistance.

Examples 21 to 26

Preparation of Resin Composition 20.0 g of the difunctional PPE oligomer (hydroxyl equivalent: 455 g/eq) obtained in Synthesis Example 2, the cyanato glass transition temperature were measured by the same methods as in Examples 14 to 20. The results are shown in Table 3.

Comparative Example 3

Production of Resin Composition

In the same manner as in Example 21, except that 30.0 g of the cyclic phosphazene compound produced in Comparative Example 1 was used in place of the cyanato group-containing cyclic phosphazene compound produced in Example 2, a resin composition was obtained. Using the resin composition, a copper foil laminate and a cured sheet were obtained by the same processes and conditions as those in Examples 21 to 26, and then soldering heat resistance, dielectric properties, flammability and glass transition temperature were evaluated. The results are shown in Table 3.

TABLE 3

| | Cyanato group-containing cyclic phosphazene compound | | Dielectric properties (Dielectric constant/Dissipation factor) | Flammability UL-94 | Tg (° C.) | Soldering heat resistance (Number of rejections/Number of samples) |
|---|---|---|---|---|---|---|
| | Examples | Amounts (g) | | | | |
| Example 21 | 2 | 30.0 | 2.8/0.07 | V-0 | 265 | 0/20 |
| Example 22 | 3 | 30.0 | 2.7/0.06 | V-0 | 268 | 0/20 |
| Example 23 | 7 | 30.0 | 2.8/0.07 | V-0 | 260 | 0/20 |
| Example 24 | 8 | 30.0 | 2.7/0.07 | V-0 | 263 | 0/20 |
| Example 25 | 9 | 30.0 | 2.6/0.05 | V-0 | 271 | 0/20 |
| Example 26 | 10 | 30.0 | 2.7/0.05 | V-0 | 265 | 0/20 |
| Comparative Example 3 | Comparative Example 1 | 30.0 | 3.0/0.09 | V-0 | 168 | 6/20 |

As seen from the results shown in Table 3, cured articles made of resin compositions of Examples 21 to 26 showed low dielectric constant and excellent dissipation factor in a frequency of a gigahertz band as compared with Comparative Example 3, and also showed high glass transition temperature and excellent soldering heat resistance.

The invention may be embodied in other various forms without departing from the spirit or essential properties thereof. The above embodiments or examples are therefore to be considered in all respects as illustrative and not restrictive. The scope of the invention is indicated by the claims and not restricted by no means by the foregoing description. Furthermore, all changes and modifications which come within the range of equivalency of the claims are therefore intended to be embraced in the present invention.

The invention claimed is:

1. A cyanato group-containing cyclic phosphazene compound represented by the following formula (1):

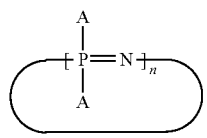

(1)

in the formula (1), n represents an integer of 3 to 15, A represents a group selected from the group consisting of an A1 group, an A2 group and an A3 group shown below, and at least one group is an A3 group:

A1 group: an alkoxy group having 1 to 8 carbon atoms which may be substituted with at least one group selected from an alkyl group having 1 to 6 carbon atoms, an alkenyl group and an aryl group, A2 group: an aryloxy group having 6 to 20 carbon atoms which may be substituted with at least one group selected from an alkyl group having 1 to 6 carbon atoms, an alkenyl group and an aryl group, and A3 group: a group selected from the group consisting of a cyanatophenyloxy group represented by the formula (2) shown below, a cyanatophenyl-substituted phenyloxy group represented by the formula (3) shown below, a cyanatophenyl-substituted phenyloxy group represented by the formula (4) shown below, a cyanatophenyl-substituted indanoxy group represented by the formula (5) shown below and a cyanatoindane-substituted phenyloxy group represented by the formula (6) shown below:

(2)

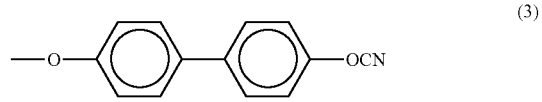

(3)

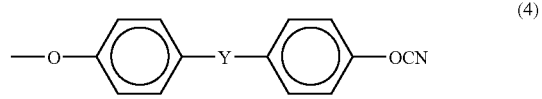

(4)

in the formula (4), Y represents O, S, SO$_2$, CH$_2$, CHCH$_3$, C(CH$_3$)$_2$, C(CF$_3$)$_2$, C(CH$_3$)CH$_2$CH$_3$ or CO,

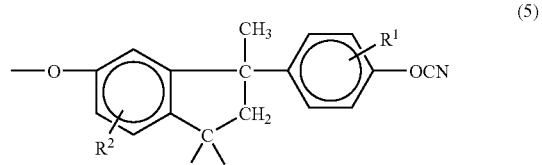

(5)

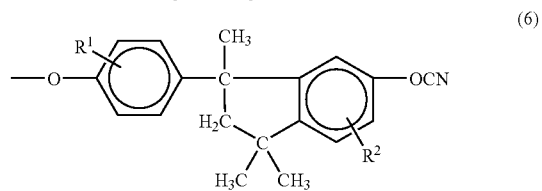

(6)

in the formulas (5) and (6), $R^1$ and $R^2$ represent a hydrogen atom, an alkyl group having 1 to 4 carbon atoms, a cycloalkyl group or a phenyl group.

2. The cyanato group-containing cyclic phosphazene compound according to claim 1, wherein n in the formula (1) is 3 or 4.

3. The cyanato group-containing cyclic phosphazene compound according to claim 2, wherein 2 to (2n−2) A groups of 2n A groups are A3 groups in the formula (1).

4. The cyanato group-containing cyclic phosphazene compound according to claim 2, wherein all 2n A(s) are A3 groups in the formula (1).

5. The cyanato group-containing cyclic phosphazene compound according to claim 1, which comprises two or more kinds of cyanato group-containing cyclic phosphazene compounds each having different n in the formula (1).

6. A method for producing a cyanato group-containing cyclic phosphazene compound, which comprises the steps of:
    substituting all halogen atoms of a cyclic phosphonitrile dihalide represented by the formula (7) shown below with a group selected from the group consisting of an E1 group, an E2 group and an E3 group shown below so as to substitute at least one of the halogen atoms with the E3 group shown below to produce a cyclic phosphonitrile-substituted compound;

(7)

in the formula (7), n represents an integer of 3 to 15 and X represents a halogen atom, E1 group: an alkoxy group having 1 to 8 carbon atoms which may be substituted with at least one group selected from an alkyl group having 1 to 6 carbon atoms, an alkenyl group and an aryl group, E2 group: an aryloxy group having 6 to 20 carbon atoms which may be substituted with at least one group selected from an alkyl group having 1 to 6 carbon atoms, an alkenyl group and an aryl group, and E3 group: a group selected from the group consisting of a substituted phenyloxy group represented by the formula (8) shown below, a substituted phenyloxy group represented by the formula (9) shown below, a substituted phenyloxy group represented by the formula (10) shown below, a substituted indanoxy group represented by the formula (11) shown below and a substituted phenyloxy group represented by the formula (12) shown below:

(8)

(9)

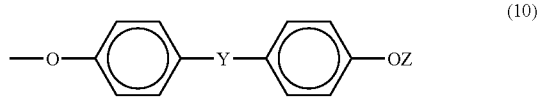

(10)

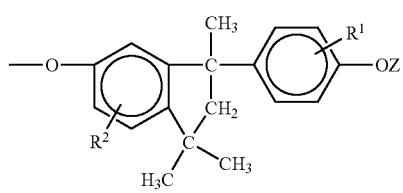

(11)

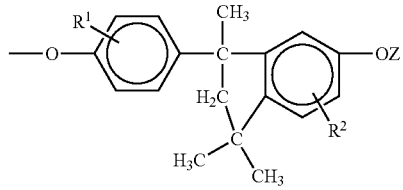

(12)

wherein Z in the formulas (8), (9), (10), (11) and (12) represents a protecting group capable of forming an OH group when eliminated, Y in the formula (10) represents O, S, $SO_2$, $CH_2$, $CHCH_3$, $C(CH_3)_2$, $C(CF_3)_2$, $C(CH_3)CH_2CH_3$ or CO, and $R^1$ and $R^2$ in the formulas (11) and (12) represent a hydrogen atom, an alkyl group having 1 to 4 carbon atoms, a cycloalkyl group or a phenyl group;

eliminating the protecting group from the E3 group of the cyclic phosphonitrile-substituted compound to produce a cyclic phosphonitrile-substituted compound having a hydroxyl group; and
    reacting the cyclic phosphonitrile-substituted compound having a hydroxyl group with a cyanogen halide.

7. The method for producing a cyanato group-containing cyclic phosphazene compound according to claim 6, wherein Z in the formulas (8), (9), (10), (11) and (12) is selected from the group consisting of a methyl group, a methoxymethyl group, a tert-butyl group, an allyl group and a benzyl group.

8. A resin composition comprising:
    a resin component, and
    a cyanato group-containing cyclic phosphazene compound represented by the following formula (1):

(1)

in the formula (1), n represents an integer of 3 to 15, A represents a group selected from the group consisting of an A1 group, an A2 group and an A3 group shown below, and at least one group is an A3 group:

A1 group: an alkoxy group having 1 to 8 carbon atoms which may be substituted with at least one group selected from an alkyl group having 1 to 6 carbon atoms, an alkenyl group and an aryl group, A2 group: an aryloxy group having 6 to 20 carbon atoms which may be substituted with at least one group selected from an alkyl group having 1 to 6 carbon atoms, an alkenyl group and an aryl group, and A3 group: a group selected from the group consisting of a cyanatophenyloxy group represented by the formula (2) shown below, a cyanatophenyl-substituted phenyloxy group represented by the formula (3) shown below, a cyanatophenyl-substituted phenyloxy group represented by the formula (4) shown below, a cyanatophenyl-substituted indanoxy group represented by the formula (5) shown below and a cyanatoindane-substituted phenyloxy group represented by the formula (6) shown below:

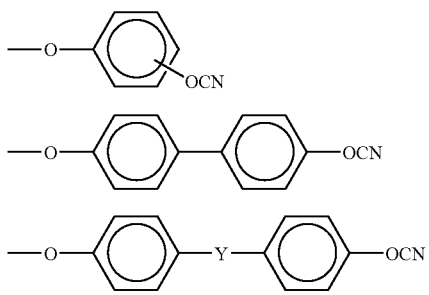

in the formula (4), Y represents O, S, SO$_2$, CH$_2$, CHCH$_3$, C(CH$_3$)$_2$, C(CF$_3$)$_2$, C(CH$_3$)CH$_2$CH$_3$ or CO,

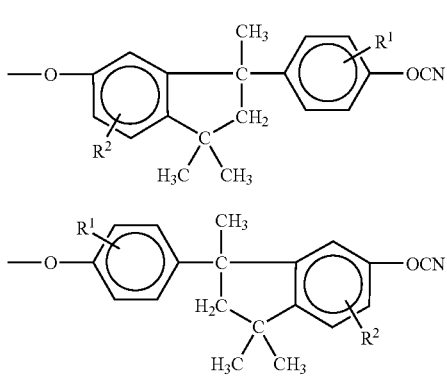

in the formulas (5) and (6), R$^1$ and R$^2$ represent a hydrogen atom, an alkyl group having 1 to 4 carbon atoms, a cycloalkyl group or a phenyl group.

9. The resin composition according to claim 8, wherein the resin component is selected from the group consisting of a cyanate ester resin, an epoxy resin, a polyimide resin, a bismaleimide resin, a bismaleimide-cyanate ester resin and a modified polyphenylene ether resin.

10. The resin composition according to claim 8, wherein the resin component is an epoxy resin and a curing agent is further contained.

11. A resin molded product made of a resin composition comprising a resin component and a cyanato group-containing cyclic phosphazene compound represented by the following formula (1):

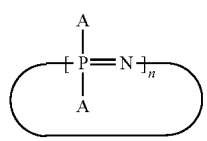

in the formula (1), n represents an integer of 3 to 15, A represents a group selected from the group consisting of an A1 group, an A2 group and an A3 group shown below, and at least one group is an A3 group:

A1 group: an alkoxy group having 1 to 8 carbon atoms which may be substituted with at least one group selected from an alkyl group having 1 to 6 carbon atoms, an alkenyl group and an aryl group, A2 group: an aryloxy group having 6 to 20 carbon atoms which may be substituted with at least one group selected from an alkyl group having 1 to 6 carbon atoms, an alkenyl group and an aryl group, and A3 group: a group selected from the group consisting of a cyanatophenyloxy group represented by the formula (2) shown below, a cyanatophenyl-substituted phenyloxy group represented by the formula (3) shown below, a cyanatophenyl-substituted phenyloxy group represented by the formula (4) shown below, a cyanatophenyl-substituted indanoxy group represented by the formula (5) shown below and a cyanatoindane-substituted phenyloxy group represented by the formula (6) shown below:

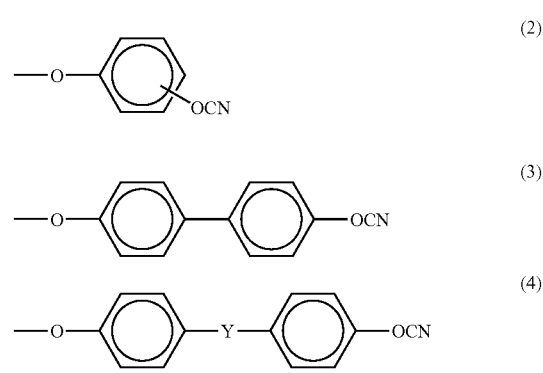

in the formula (4), Y represents O, S, SO$_2$, CH$_2$, CHCH$_3$, C(CH$_3$)$_2$, C(CF$_3$)$_2$, C(CH$_3$)CH$_2$CH$_3$ or CO,

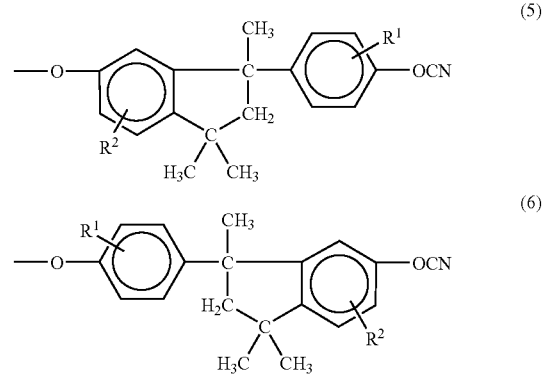

in the formulas (5) and (6), R$^1$ and R$^2$ represent a hydrogen atom, an alkyl group having 1 to 4 carbon atoms, a cycloalkyl group or a phenyl group.

12. A polymerizable composition comprising a cyanato group-containing cyclic phosphazene compound represented by the following formula (1):

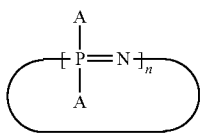

in the formula (1), n represents an integer of 3 to 15, A represents a group selected from the group consisting of an A1 group, an A2 group and an A3 group shown below, and at least one group is an A3 group:

A1 group: an alkoxy group having 1 to 8 carbon atoms which may be substituted with at least one group selected from an alkyl group having 1 to 6 carbon atoms, an alkenyl group and an aryl group, A2 group: an aryloxy group having 6 to 20 carbon atoms which may be substituted with at least one group selected from an alkyl group having 1 to 6 carbon atoms, an alkenyl group and an aryl group, and A3 group: a group selected from the group consisting of a cyanatophenyloxy group represented by the formula (2) shown below, a cyanatophenyl-substituted phenyloxy group represented by the formula (3) shown below, a cyanatophenyl-substituted phenyloxy group represented by the formula (4) shown below, a cyanatophenyl-substituted indanoxy group represented by the formula (5) shown below and a cyanatoindane-substituted phenyloxy group represented by the formula (6) shown below:

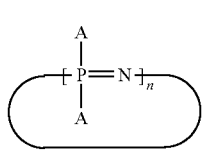

in the formula (4), Y represents O, S, SO$_2$, CH$_2$, CHCH$_3$, C(CH$_3$)$_2$, C(CF$_3$)$_2$, C(CH$_3$) CH$_2$CH$_3$ or CO,

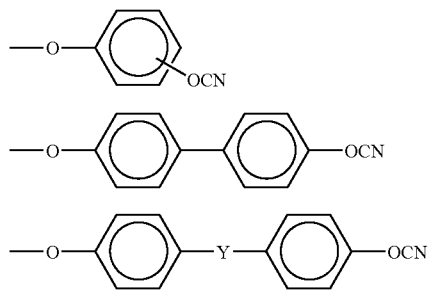

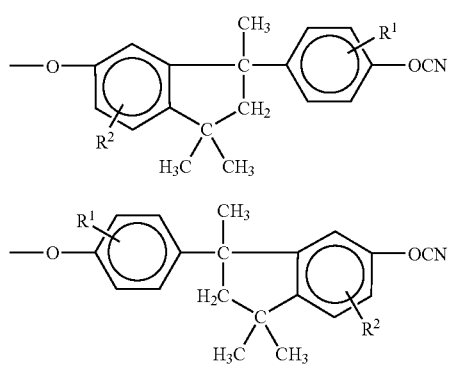

in the formulas (5) and (6), R$^1$ and R$^2$ represent a hydrogen atom, an alkyl group having 1 to 4 carbon atoms, a cycloalkyl group or a phenyl group.

13. The polymerizable composition according to claim 12, further comprising a curing agent.

14. A resin molded product made of a polymer of a polymerizable composition comprising a cyanato group-containing cyclic phosphazene compound represented by the following formula (1):

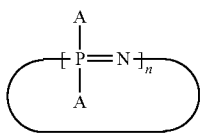

in the formula (1), n represents an integer of 3 to 15, A represents a group selected from the group consisting of an A1 group, an A2 group and an A3 group shown below, and at least one group is an A3 group:

A1 group: an alkoxy group having 1 to 8 carbon atoms which may be substituted with at least one group selected from an alkyl group having 1 to 6 carbon atoms, an alkenyl group and an aryl group, A2 group: an aryloxy group having 6 to 20 carbon atoms which may be substituted with at least one group selected from an alkyl group having 1 to 6 carbon atoms, an alkenyl group and an aryl group, and A3 group: a group selected from the group consisting of a cyanatophenyloxy group represented by the formula (2) shown below, a cyanatophenyl-substituted phenyloxy group represented by the formula (3) shown below, a cyanatophenyl-substituted phenyloxy group represented by the formula (4) shown below, a cyanatophenyl-substituted indanoxy group represented by the formula (5) shown below and a cyanatoindane-substituted phenyloxy group represented by the formula (6) shown below:

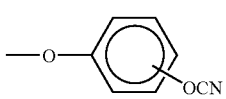

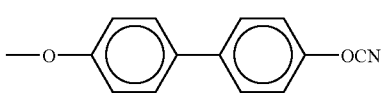

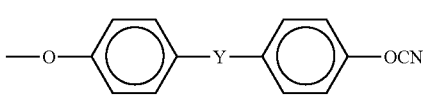

in the formula (4), Y represents O, S, SO$_2$, CH$_2$, CHCH$_3$, C(CH$_3$)$_2$, C(CF$_3$)$_2$, C(CH$_3$)CH$_2$CH$_3$ or CO,
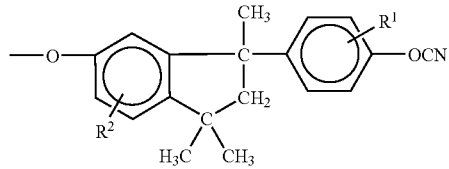
(5)
-continued
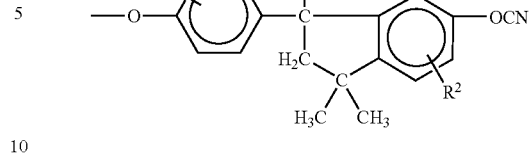
(6)
in the formulas (5) and (6), R$^1$ and R$^2$ represent a hydrogen atom, an alkyl group having 1 to 4 carbon atoms, a cycloalkyl group or a phenyl group.
* * * * *